US007342111B2

(12) United States Patent
Lewin et al.

(10) Patent No.: US 7,342,111 B2
(45) Date of Patent: Mar. 11, 2008

(54) ADENO-ASSOCIATED VIRUS-DELIVERED RIBOZYME COMPOSITIONS AND METHODS OF USE

(75) Inventors: Alfred S. Lewin, Gainesville, FL (US); William Hauswirth, Gainesville, FL (US); Xiaoping Qi, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 32 days.

(21) Appl. No.: 11/256,607

(22) Filed: Oct. 21, 2005

(65) Prior Publication Data

US 2006/0248604 A1 Nov. 2, 2006

Related U.S. Application Data

(62) Division of application No. 09/561,498, filed on Apr. 28, 2000, now abandoned.

(60) Provisional application No. 60/131,942, filed on Apr. 30, 1999.

(51) Int. Cl.
*A61K 48/00* (2006.01)
*C12N 15/63* (2006.01)
*C07H 21/02* (2006.01)
*C07H 21/04* (2006.01)

(52) U.S. Cl. ............... 536/24.5; 435/320.1; 536/23.1; 514/44

(58) Field of Classification Search .............. None
See application file for complete search history.

(56) References Cited

U.S. PATENT DOCUMENTS

| | | | |
|---|---|---|---|
| 4,683,195 A | 7/1987 | Mullis et al. |
| 4,683,202 A | 7/1987 | Mullis |
| 4,800,159 A | 1/1989 | Mullis et al. |
| 4,883,750 A | 11/1989 | Whiteley et al. |
| 4,987,071 A | 1/1991 | Cech et al. |
| 5,037,746 A | 8/1991 | Cech et al. |
| 5,093,246 A | 3/1992 | Cech et al. |
| 5,116,742 A | 5/1992 | Cech et al. |
| 5,297,721 A | 3/1994 | Schneider et al. |
| 5,334,711 A | 8/1994 | Sproat et al. |
| 5,354,855 A | 10/1994 | Cech et al. |
| 5,455,166 A | 10/1995 | Walker |
| 5,498,539 A | 3/1996 | Harrison et al. |
| 5,631,359 A | 5/1997 | Chowrira et al. |
| 5,639,655 A | 6/1997 | Thompson et al. |
| 5,646,020 A | 7/1997 | Swiggen et al. |
| 5,646,031 A | 7/1997 | DeYoung |
| 5,648,211 A | 7/1997 | Fraiser et al. |
| 5,712,124 A | 1/1998 | Walker |
| 5,744,311 A | 4/1998 | Fraiser et al. |
| 6,225,291 B1 | 5/2001 | Lewin et al. |
| 6,943,153 B1 | 9/2005 | Manning, Jr. et al. |

| | | | |
|---|---|---|---|
| 2001/0034054 A1 | 10/2001 | Dwarki et al. |
| 2001/0051611 A1 | 12/2001 | Srivastava et al. |
| 2002/0132336 A1 | 9/2002 | Dwarki et al. |
| 2002/0194630 A1 | 12/2002 | Manning, Jr. et al. |
| 2003/0166284 A1 | 9/2003 | Srivastava et al. |

FOREIGN PATENT DOCUMENTS

| | | |
|---|---|---|
| EP | 0360257 | 3/1990 |
| EP | 0320308 | 11/1993 |
| EP | 0329822 | 6/1994 |
| GB | 2202328 | 9/1988 |
| WO | WO87/06270 | 10/1987 |
| WO | WO88/10315 | 12/1988 |
| WO | WO89/06700 | 7/1989 |
| WO | WO89/09284 | 10/1989 |
| WO | WO90/07641 | 7/1990 |
| WO | WO91/03162 | 3/1991 |
| WO | WO92/07065 | 4/1992 |
| WO | WO93/15187 | 8/1993 |
| WO | WO93/23569 | 11/1993 |
| WO | WO94/02595 | 2/1994 |
| WO | WO94/13688 | 6/1994 |
| WO | WO95/04142 | 2/1995 |
| WO | WO97/11169 | 3/1997 |
| WO | WO97/32024 | 9/1997 |
| WO | WO98/48009 | 10/1998 |
| WO | WO98/48027 | 10/1998 |
| WO | WO 00/54813 A2 | 9/2000 |

(Continued)

OTHER PUBLICATIONS

Afzal et al., "Reduction on Preretinal Neovascularization by Ribozymes that Cleave the $A_{2B}$ Adrenosine Receptor mRNA," *Circulation Research*, Sep. 23, 2003.

(Continued)

*Primary Examiner*—J. Douglas Schultz
*Assistant Examiner*—Amy H. Bowman
(74) *Attorney, Agent, or Firm*—Haynes and Boone, LLP; Mark D. Moore

(57) ABSTRACT

Provided are methods for the identification of novel genes involved in a variety of cellular processes, including retinal degeneration, retinal disease, cancer, memory and learning, amylotropic lateral sclerosis, and methods for the identification of the function of a variety of genes and gene fragments of unknown function. The genes thus identified, as well as the compositions used in the identification methods, are also provided.

16 Claims, 29 Drawing Sheets

FOREIGN PATENT DOCUMENTS

| WO | WO 02/24234 A2 | 3/2002 |
| WO | WO 02/088320 A2 | 11/2002 |

OTHER PUBLICATIONS

Alfione et al., "In vivo model of adeno-associated virus vector persistence and rescue," *Journal of Virology*, 70:3235-3241, 1996.
Altschuler et al., "A method for generating transcripts defined with 5' and 3' termini by autolytic processing," *Gene*, 122:85-90, 1992.
Al-Ubaidi et al., "Photoreceptor degeneration induced by the expression of simian virus 40 large tumor antigen in the retina of transgenic mice," *Proc.Natl. Acad. Sci.USA*, 89:1194-1198, 1992.
Bergsland et al., "Update on Clinical Trials Targeting Vascular Endothelial Growth Factor in Cancer," *Am. J. Health Syst. Pharm.*, 61(5): S12-S20, Nov. 2004.
Blalock et al., "Hammerhead ribozyme targeting connective tissue growth factor mRNA blocks transforming growth factor-beta mediated cell proliferation," *Experimental Eye Research*, 78: 1127-1136, 2004.
Cech, "Self-splicing of Group I introns," *Annu. Rev. Biochem*, 59:543-568, 1990.
Chakravathy et al., "Nitric oxide synthase activity and expression in retinal capillary endothelial cells and pericytes," *Curr. Eye Res.*, 14(4):285-294, 1995.
Chen et al., "The human blue opsin promoter directs transgene expression in short-wave cones and bipolar cells in the mouse retina," *Proc. Natl. Acad. Sci. USA*, 91(7):2611-2615, 1994.
Christoffersen et al., "Ribozymes as Human Therapeutic Agents," *J. Med. Chem.*, 38: 2023-2037, Jun. 1995.
Chiu et al., "A sequence upstream of the mouse blue visual pigment gene directs blue cone-specific transgene expression in mouse retinas," *Visual Neuroscience*, 11(4):773-780, 1994.
Cipolla et al., "High glucose concentrations dilate cerebral arteries and diminish myogenic tone through an endothelial mechanism," *Stroke*, 28(2):405-411, 1997.
Cosentino et al., "High glucose increases nitric oxide synthase expression and superoxide anion generation in human aortic endothelial cells," *Circulation*, 96(1):25-28, 1997.
Cordiero et al., "Molecular Therapy in Ocular Wound Healing," *BJO Online*, 83: 1219-1224, 1999.
Crooke, "Another Piece in the Mosaic. Antisense and Nucleic Acid Drug Development," 8:vii-viii, 1998.
Crystal, "Transfer of genes to humans: early lessons and obstacles to success," *Science*, 270:404-410, 1995.
Daiger et al., "Correlation of phenotype with genotype in inherited retinal degeneration," *Behavioral and Brain Sciences*, 18:452-467, 1995.
Desjardin et al., "Developmentally important DNA elements within the bovine opsin upstream region," *Investigative Ophthalmology & Visual Science*, 37(1):154-165, 1996.
Drenser et al., "Ribozyme mediated degredation of the P23H and S334Ter mutant mRNAs associated with ADRP," *Investigative Opthalmology & Visual Science*, 38(4):S441, Abstract 2085, 1997 (Annual Mtg. Of the Association for Research in Vision and Opthalmology, Fort Lauderdale, Florida, USA, May 11-196, 1997).
Drenser et al., "Ribozyme mediated destruction of an messenger-RNA causing retinitis pigmentosis," *Investigative Ophthalmology & Visual Science*, 37(3):S10, Abstract 42, 1996.
Drenser et al., "Ribozyme-targeted destruction of RNA associated with autosomal-dominant retinitis pigmentosa," *Investigative Ophthalmology & Visual Science*, 39(5):681-689, 1998.
Farrar et al., "On the Genetics of Retinits Pignentosa and on Mutation-Independent Approaches to Therapeutic Intervention," *EMBO J.*, 21(5): 857-864, 2002.
Flannery et al., "Efficient photoreceptor-targeted gene expression in vivo by recombinant adeno-associated virus," *Proc. Natl. Acad. Sci. USA*, 94(13):6916-6921, 1997.
Flotte et al., "Stable in vivo expression of the cystic fibrosis transmembrane conductance regulator with an adeno-associated virus vector," *Proc. Natl, Acad. Sci. USA*, 90(22):10613-10617, 1993.

Fritz et al., "Design and Validation of Therapeutic Hammerhead Ribozymes for Autosomal Dominant Diseases," *Methods Mol. Bio.*, 252: 221-36, 2004.
Fritz et al., "Designing and Characterizing Hammerhead Ribozymes for Use in AAV Vector-Mediated Retinal Gene Therapies," *Methods Enzymol.*, 346: 358-77, 2002.
Fritz et al., "Development of Hammerhead Ribozymes to Modulate Endogenous Gene Expression For Functional Studies," *Methods*, 28(2): 276-85, Oct. 2002.
Gade et al., "Nitric oxide mediates hyperglycemia-induced defective migration in cultured endothelial cells," *Journal of Vascular Surgery*, 26(2):319-326, 1997.
Gewirtz et al., "Facilitating Oligonucleotide Delivery: Helping Antisense Deliver on its Promise," *Proc. Natl. Acad. Sci*, 93: 3161-3163, Apr. 1996.
Goldstein, Ostwal and Roth, "Nitric oxide: a review of its role in retinal function and disease," *Vision Res.*, 36(18):2979-2994, 1996.
Gorbatyuk et al., "Knockdown of Wild-Type Mouse Rhodopsin Using an AAV Vectored Ribozyme as Part of an RNA Replacement Approach," *Mol. Vis.*, 11: 648:56, Aug. 29, 2005.
Hangai et al., "Inducible nitric oxide synthase in retinal ischemia-reperfusion injury," *Exp. Eye Res.*, 63(5):501-509, 1996.
Hauswirth et al., "Adeno-associated virus delivery of an opsin promoter driven reporter gene to the mouse and rabbit retina," *Gene Therapy*, 2(Supp. 1):S2, Abstract 6, 1995.
Hauswirth et al., "Range of Retinal Disease Potentially Treatable by AAV-vectored Gene Therapy," *Novartis Found. Symp.*, 255: 179-194, 2004.
Hauswirth et al., "Ribozyme Gene Therapy for Autosomal Dominant Retinal Disease," *Clin. Chem. Lab. Med. 2000*, 38(2): 147-153, 2000.
Hauswirth et al., "Ribozyme Uses in Retinal Gene Therapy," *Prog. Retin. Eye Res.*, 19(6): 689-710, Nov. 2000.
Kaplitt et al., "Long-term gene expression and phenotypic correction using adeno-associated virus vectors in the mammalian brain," *Nature Genetics*, 8:148-154, 1994.
Kessler et al., "Gene delivery to skeletal muscle results in sustained expression and systemic delivery of a therapeutic protein," Proc. Natl. Acad. Sci. USA, 93:14082-14087, 1996.
Kido et al., "Use of a retroviral vector with an internal opsin promoter to direct gene expression to retinal photoreceptor cells,", *Current Eye Research*, 15:833-844, 1996.
Koizumi et al., "Ribozymes designed to inhibit transformation of NIH3T3 cells by the activated c-Ha-*ras* gene," *Gene*, 117:179-184, 1992.
Komatsu et al., "A new type of hairpin ribozyme consisting of three domains," *Biochemistry*, 36(32):9935-9940, 1997.
Lavail et al., "Ribozyme rescue of Photoreceptor Cells in P23H Transgenic Rats: Long-Term Survival and Late-Stage Therapy," *Proc. Natl. Acad. Sci. Early Edition*, 10: 1073, Sep. 2000.
Lem et al., "Tissue-specific and developmental regulation of rod opsin chimeric genes in transgenic mice," *Neuron*, 6:201-210, 1991.
Lewin et al., "Gene Therapy for Autosomal Dominant Disorders of Keratin," *J. Investig. Dermatol. Symp. Proc.*, 10(1): 47-61, 2005.
Lewin et al., "Ribozyme Gene Therapy: Applications for Molecular Medicine," *Trends Mol. Med.*, 7(5): 221-8, May 2001.
Lewin et al., "Ribozyme rescue of photoreceptor cells in a transgenic rat model of Autosomal Dominant Retinitis Pigmentosa," *Nat. Med.*, 4(8):967-971, Aug. 1998, Erratum in: *Nat. Med.*, 4(9): 1081, Sep. 1998.
Li et al., "Cone-specific gene transfer and expression using human red/green opsin promoter in a recombinant AAV,", *IOVS*, 39(4):S721, 3311-B137, 1998.
Little et al., "Generation of a mammalian cell line deficient in glucose-regulated protein stress induction through targeted ribozyme driven by a stress-inducible promoter," *The Journal of Biological Chemistry*, 270(16):9526-9534, 1995.
Liu et al., "Ribozyme Knockdown for the Gamma-Subunit of Rod cGMP Phosphodiesterase Alters the ERG and Retinal Morphology in Wild-Type Mice," *Invest. Ophthalmol. Vis. Sci.*, 46(10): 3836-44, Oct. 2005.

Lyngstadaas et al., "A Synthetic, Chemically Modified Ribozyme Eliminates Amelogenin, the Major Translation Product in Developing Mouse Enamel in vivo," *Embo J.*, 14: 5224-5229, 1995.

Millington-Ward et al., "Strategems in vivo for gene therapies directed to dominant mutations," *Human Molecular Genetics*, 6(9):1415-1426, 1997.

Ojwang et al., "Inhibition of human immunodeficiency virus type 1 expression by a hairpin ribozyme," *Proc. Natl. Acad. Sci. USA*, 89:10802-10806, 1992.

Orkin et al., "Report and Recommendations of the Panel to Assess the NIH Investment in Research on Gene Therapy," *National Institutes of Health*, 1995.

Ostwald et al., "Effect of nitric oxide synthase inhibition on blood flow after retinal ischemia in cats," *Investigative Ophthalmology & Visual Science*, 36(12):2396-2403, 1995.

Qi et al., "Optic Neuropathy Induced by Reductions in Mitochondrial Superoxide Dismutase," *Invest. Ophthalmol. Vis. Sci.*, 44(3): 1088-96, Mar. 2003.

Qi et al., "SOD2 Gene Transfer Protects Against Optic Neuropathy Induced By Deficiency of Complex I," *Ann. Neurol.*, 56(2): 182-91, Aug. 2004.

Qi et al., "Suppression of Complex I Gene Expression Induces Optic Neuropathy," *Ann. Neurol.*, 53(2): 198-205, Feb. 2003.

Raymond et al., "Expression of rod and cone visual pigments in goldfish and zebrafish: a rhodopsin-like gene is expressed in cones," *Neuron*, 10:1161-1174, 1993.

Ross et al., "Gene therapy in the United States: A five year status report," *Human Gene Therapy*, 7:1781-1790, 1996.

Sharma et al., "Enhance expression of inducible nitric oxide synthase in murine macrophages and glomerular mesangial cells by elevated glucose levels: Possible mediation via protein kinase C+," *Biochem. Biophys. Res. Comm.*, 207(1):80-88, 1995.

Shaw et al., "An Allele-Specific Hammerhead Ribozyme Gene Therapy For a Porcine Model of Autosomal Dominant Retinitis Pigmentosa," *Mol. Vis.*, 7: 6-13, Jan. 2001.

Shaw et al., "Decreased Expression of the Insulin-like Growth Factor 1 Receptor by Rribozyme Cleavage," *IOVS*, 44 (9): 4105-4113, Sep. 2003.

Shaw et al., "Ribozymes in Treatment of Inherited Retinal Desease," *Methods Enzymol.*, 316: 716-76, 2000.

Stein, "Keeping the Biotechnology of Antisense in Context," *Nat. Biotechnol.*, 17: 209, Mar. 1999.

Steinberg et al., "Transgenic rat models of inherited retinal degeneration caused by mutant opsin genes," *Inv. Ophth. Vis. Sci.*, 37:S698, Abstract, 1996.

Stull et al., "Antigene, Ribosyme and Aptamer Nucleic Acid Drugs: Progress and Prospects," *Pharm. Res.*, 12: 465-483, Apr. 1995.

Timmers et al., "Synthesis and stability of retinal photoreceptor mRNAs are coordinately regulated during bovine fetal development," *Exp. Eye Res.*, 56:257-265, 1993.

Van Ginkel et al., "Parallel regulation of fetal gene expression in different photoreceptor cell types," *The Journal of Biological Chemistry*, 269(7):4986-4992, 1994.

Verma et al., "Gene therapy—promises, problems and prospects," *Nature*, 389:239-242, 1997.

Von Weizsäcker et al., "Cleavage of hepatitis B virus RNA by three ribozymes transcribed from a single DNA template," *Biochemical and Biphysical Research Communications*, 189(2):743-748, 1992.

Xiao et al., "Efficient long-term gene transfer into muscle tissue of immunocompetent mice by adeno-associated virus vector," *Journal of Virology*, 70(11):8098-8108, 1996.

Xing et al., "An anti-lymphocytic choriomeningitis virus ribozyme expressed in tissue culture cells diminishes viral RNA levels and leads to a reduction in infectious viral yield," *Journal of Virology*, 67(4): 1840-1847, 1993.

Yu et al., "A hairpin ribozyme inhibits expression of diverse strains of human immunodeficiency virus type 1," *Proc. Natl, Acad. Sci. USA*, 90:6340-6344, 1993.

Yu et al., "In vitro and in vivo characterization of a second functional hairpin ribozyme against HIV-1," *Virology*, 206(1):381-386, 1995.

Yung, "Molecular modulation of vascular entothelian growth factor (VEGF) expression in glioma cells by ribozymes," *Neurology*, 48(3 Suppl. 2):A22, Abstract VI3.001, 1997.

Zolotukhin et al., "A humanized green fluorescent protein cDNA adapted for high-level expression in mammalian cells," *Journal of Virology*, 70(7):4646-4654, 1996.

International Search Report dated Feb. 1, 1999 (PCT/US98/07968) (4300.011510).

International Search Report dated Feb. 16, 1999 (PCT/US98/08003) (4300.011410).

International Search Report PCT/US02/13679; Apr. 4, 2005.

International Preliminary Examination Report PCT/US02/1379; Sep. 15, 2005.

5'-NNNNGUCNNNNNN-3'   Target (SEQ ID NO:2)
3'-NNNNCA NNNNNN-5'

```
     A   C U
     |    G
     A    A
     G    U
     C   AG
     C-G
     G-C
     U-A
     C-G
     G-C
     G  U
     C  U
```

(SEQ ID NO:1)

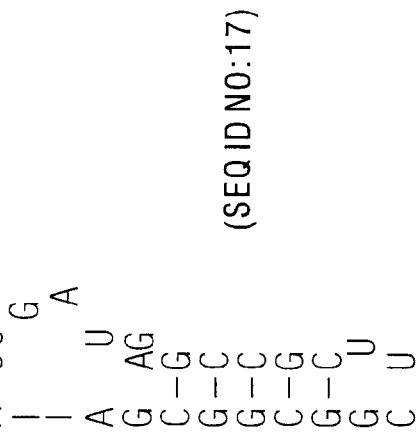

```
5'-UCCACAAGUCCAAACAG-3'  Substrate CREB 288 (SEQ ID NO:18)
3'-AGGUGUUCA GUUUGUC-5'
           A  CU G
            A   A
           G  AG
           C—G
           G—C
           G—C
           C—G
           C—C
           G  U
            C U
                    (SEQ ID NO:17)
```

Oligonucleotides:

```
            HindIII                                                      NsiI
Oligo 5:  5'-agcttCTGTTTGCTGATGAGCCGCTTCGGCGGGCGAAACTTGTGGAatgca-3'  (SEQ ID NO:19)
Oligo 6:  3'-    aGACAAACGACTACTCGGCGAAGCCGCCCGCTTTGAACACCTt    -5'  (SEQ ID NO:20)
```

Catalytic domain mutant CREB 288

```
Oligo 10: 5'-agcttCTGTTTGCTGcTGAcCCGCTTCGGCGGGCGAAACTTGTGGAatgca-3'  (SEQ ID NO:21)
Oligo 11: 3'-    aGACAAACGACgACTgGGCGAAGCCGCCCGCTTTGAACACCTt    -5'  (SEQ ID NO:22)
```

FIG. 12

```
5'-CUACGUAGCAGAA-3' (nt 1037-1049) βPDE murine (SEQ ID NO:30)
3'-GAUGCA CGUCUU-5'
        A  CU
        I    G
        I    A
        A  U
        G AG
        C-G
        C-G        (SEQ ID NO:29)
        G-C
        G-C
        A  G
        A  A
```
FIG. 15
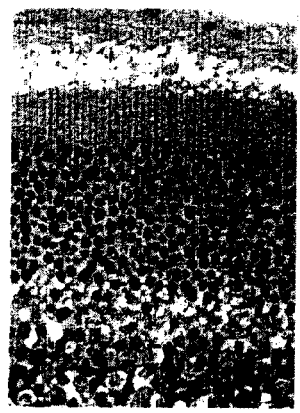
FIG. 16A
FIG. 16B
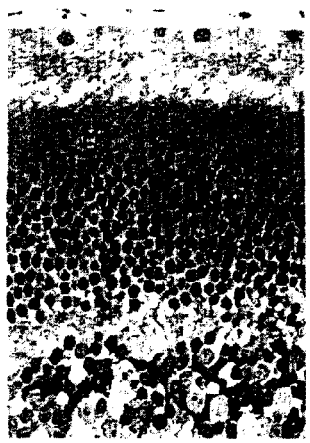
FIG. 16C
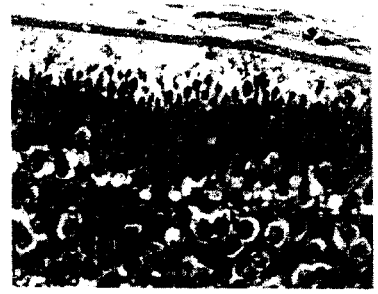
FIG. 16D

Human and rat ABCR (Rz114)

```
         ▼
5'-UUCGGUCUUGAUC-3'    Target CUTS AT POSITION 114 of ABCR)
3'-AAGACCA AACUAG-5'   (SEQ ID NO:32)
         A  CU
         |    G
         |     A
         A    U
         G   AG
         C-G
         G-C                    (SEQ ID NO:31)
         C-G
         G-C
         G   U
          C U
```

FIG. 17A mouse ABCR

```
         ▼
5'-GAACUGUCUCAAAC-3'   Target (SEQ ID NO: 34)
3'-CUUGACA AGUUUG-5'
         A  CU
         |    G
         |     A
         A    U
         G   AG
         C-G
         G-C                    (SEQ ID NO:33)
         C-G
         G-C
         G   U
          C U
```

FIG. 17B mouse NADH dehydrogenase MWFE subunit nt 338

```
5'-UGGAG   ▼UCAAUCGC-3'   Target 332-344  (SEQ ID NO:48)
3'-ACCU CA  UUAGCG-5'
        A  CU G
           C U
         A  AG
         G   G
         C — G
         G — C
         C — G
         C — C
         G   U
          C  U
```
(SEQ ID NO:47)

Ribozyme DNA oligo: 5'-GCGATTCTGATGAGGCGTTCGGGCGAAACTCCA-3' (SEQ ID NO:69)

5'-agctGCGATTCTGATGAGGCGTTCGGGCGAAACTCCAtgca-3' (SEQ ID NO:70)
3'-    CGCTAAGACTACTCGGCGAAGCCCGCGCTTTGAGGT    -5' (SEQ ID NO:71)

Complementary strand to order:

TGG AGT TTC GCG CCG AAG CGC TCA TCA GAA TCG C    (SEQ ID NO:72)

FIG. 26

Hammerhead for mouse MnSOD nt 432

```
5'-UUGGG     ▶ UCUUUUGA-3'  Target 426-438   (SEQ ID NO:50)
3'-AACCCA      AAAACU-5'
         A   C U
          A   G
           A U
          AG
         G   G
         C - G
         G - C            (SEQ ID NO:49)
         C - G
         G - C
          G   U
           C U
```

Ribozyme DNA oligo: 5'-TCAAAACTGATGAGGCGCTTCGGGGCGAAACCCAA-3'  (SEQ ID NO:73)

5'-agctTCAAAACTGATGAGGCGCTTCGGGGCGAAACCCAAtgca-3'  (SEQ ID NO:74)
3'-     AGTTTTGACTACTCGCGAAGCCGCGCTTTGGGTT     -5'  (SEQ ID NO:75)

Complementary strand to order:

TTG GGT TTC GCG CCG AAG CGC TCA TCA GCT GAA A   (SEQ ID NO:76)

FIG. 27

5'- CTG GCT CTT AAC GGC GTT TAT GTC CTT TGC TGT CTG AGG GGC CTC
AGC TCT GAC CAA TCT GGT CTT CGT GTG GTC ATT AGC ATG GGC TTC GTG
AGA CAG ATA CAG CTT TTG CTC TGG AAG AAC TGG ACC CTG CGG AAA AGG
CAA AAG ATT CGC TTT GTG GTG GAA CTC GTG TGG CCT TTA TCT TTA TTT
CTG GTC TTG ATC TGG TTA AGG AAT GCC AAC CCG CTC TAC AGC CAT CAT
GAA TGC CAT TTC CCC AAC AAG GCG ATG CCC TCA GCA GGA ATG CTG CCG
TGG CTC CAG GGG ATC TTC TGC AAT GTG AAC AAT CCC TGT TTT CAA AGC
CCC ACC CCA GGA GAA TCT CCT GGA ATT GTG TCA AAC TAT AAC AAC TCC
ATC TTG GCA AGG GTA TAT CGA GAT TTT CAA GAA CTC CTC ATG AAT GCA
CCA GAG AGC CAG CAC CTT GGC CGT ATT TGG ACA GAG CTA CAC ATC TTG
TCC CAA TTC ATG GAC ACC CTC CGG ACT CAC CCG AGA GAA TTG CAG GA
AGA GGA ATA CGA ATA AGG GAT ATC TTG AAA GAT GAA GAA ACA CTG ACA
CTA TTT CTC ATT AAA AAC ATC GGC CTG TCT GAC TCA GTG GTC TAC CTT
CTG ATC AAC TCT CAA GTC CGT CCA GAG CAG TTC GCT CAT GGA GTC CCG
GAC CTG GCG CTG AAG GAC ATC GCC TGC AGC GAG GCC CTC CTGGAGCGCTTC 3'

(SEQ ID NO: 65)

FIG. 29

960 240 180 120 80  40  20  10  5  1  0 (min)

FIG. 30

Rz 114 substrate excess experiment

Hammerhead for mouse D1-1-T7 Rz52   Target 46-57   (SEQ ID NO:52)

(SEQ ID NO:51)

Ribozyme DNA oligo: 5'-TTTCAGCTGATGAGGCGCTTCGGGCGGAAACGAAT-3'   (SEQ ID NO:83)

5'-agctTTTCAGCTGATGAGGCGCTTCGGGCGGAAACGAATtgca-3'   (SEQ ID NO:84)
3'-    AAAGTCGACTACTCGGGAAGCCGCGCTTTGCTTA    -5'   (SEQ ID NO:85)

Complementary strand to order:

ATT CGT TTC GCG CCG AAG CGC TCA TCA GCT GAA A   (SEQ ID NO:86)

Ribozyme SOD-1 429

5'-GGAAGUCGUUUGG-3' Substrate (SEQ ID NO:62)
3'-CCUUCA CAAACC-5'
```
       A CU
        | |  G
        | |  A
        A    U
        G    AG
        C  — G
        G  — C
        G  — C
        C  — G
        G    U
        C    U
```
(SEQ ID NO:61)

Oligonucleotides:

HindIII                                                                                     NsiI Oligo sod7: 5'-agcttCCAAACCTGATGAGCCGTTCGGGGCGAAACTTCCatgca-3'    SEQ ID NO:97
Oligo sod8: 3'-    aGGTTTGGACTACTCGGCAAGCCCGCTTTGAAGGt    -5'    SEQ ID NO:98

SEQUENCE LISTING

```
<160> NUMBER OF SEQ ID NOS: 98

<210> SEQ ID NO 1
<211> LENGTH: 37
<212> TYPE: RNA
<213> ORGANISM: Artificial Sequence
<220> FEATURE:
<223> OTHER INFORMATION: Description of Artificial Sequence: SYNTHETIC
      PEPTIDE
<220> FEATURE:
<221> NAME/KEY: misc_feature
<222> LOCATION: (1)..(37)
<223> OTHER INFORMATION: where n = a, g, c or u

<400> SEQUENCE: 1
nnnnnncuga ugagcagcuu cggcugcgaa acnnnnn                                37

<210> SEQ ID NO 2
<211> LENGTH: 14
<212> TYPE: RNA
<213> ORGANISM: Artificial Sequence
<220> FEATURE:
<223> OTHER INFORMATION: Description of Artificial Sequence: SYNTHETIC
      PEPTIDE
<220> FEATURE:
<221> NAME/KEY: misc_feature
<222> LOCATION: (1)..(14)
<223> OTHER INFORMATION: where n = a, g, c or u

<400> SEQUENCE: 2
nnnnngucnn nnnn                                                         14

<210> SEQ ID NO 3
<211> LENGTH: 36
<212> TYPE: RNA
<213> ORGANISM: Artificial Sequence
<220> FEATURE:
<223> OTHER INFORMATION: Description of Artificial Sequence: SYNTHETIC
      PEPTIDE

<400> SEQUENCE: 3
gcagcgcuga ugagcagcuu cggcugcgaa acucca                                 36

<210> SEQ ID NO 4
<211> LENGTH: 13
<212> TYPE: RNA
<213> ORGANISM: Artificial Sequence
<220> FEATURE:
<223> OTHER INFORMATION: Description of Artificial Sequence: SYNTHETIC
      PEPTIDE

<400> SEQUENCE: 4
uggaguccgc ugc                                                          13
```

```
<210> SEQ ID NO 5
<211> LENGTH: 38
<212> TYPE: RNA
<213> ORGANISM: Artificial Sequence
<220> FEATURE:
<223> OTHER INFORMATION: Description of Artificial Sequence: SYNTHETIC
      PEPTIDE

<400> SEQUENCE: 5
aaccugccug augagcagcu ucggcugcga aacccaug                                38

<210> SEQ ID NO 6
<211> LENGTH: 15
<212> TYPE: RNA
<213> ORGANISM: Artificial Sequence
<220> FEATURE:
<223> OTHER INFORMATION: Description of Artificial Sequence: SYNTHETIC
      PEPTIDE

<400> SEQUENCE: 6
caugggucgc agguu                                                         15

<210> SEQ ID NO 7
<211> LENGTH: 37
<212> TYPE: RNA
<213> ORGANISM: Artificial Sequence
<220> FEATURE:
<223> OTHER INFORMATION: Description of Artificial Sequence: SYNTHETIC
      PEPTIDE

<400> SEQUENCE: 7
auaucccuga ugagcagcuu cggcugcgaa acuguga                                 37

<210> SEQ ID NO 8
<211> LENGTH: 14
<212> TYPE: RNA
<213> ORGANISM: Artificial Sequence
<220> FEATURE:
<223> OTHER INFORMATION: Description of Artificial Sequence: SYNTHETIC
      PEPTIDE

<400> SEQUENCE: 8
ucacagucgg auau                                                          14

<210> SEQ ID NO 9
<211> LENGTH: 39
<212> TYPE: RNA
<213> ORGANISM: Artificial Sequence
<220> FEATURE:
<223> OTHER INFORMATION: Description of Artificial Sequence: SYNTHETIC
      PEPTIDE

<400> SEQUENCE: 9 aacuuucug augagcagcu ucggcugcga aacauaaug                                39

<210> SEQ ID NO 10
<211> LENGTH: 16
<212> TYPE: RNA
<213> ORGANISM: Artificial Sequence
<220> FEATURE:
<223> OTHER INFORMATION: Description of Artificial Sequence: SYNTHETIC
      PEPTIDE

<400> SEQUENCE: 10
cauuauguca aaaguu                                                        16
```

<210> SEQ ID NO 11
<211> LENGTH: 38
<212> TYPE: RNA
<213> ORGANISM: Artificial Sequence
<220> FEATURE:
<223> OTHER INFORMATION: Description of Artificial Sequence: SYNTHETIC
      PEPTIDE

<400> SEQUENCE: 11
gaccugcuga ugagccgcuu cggcggcgaa acugucug                           38

<210> SEQ ID NO 12
<211> LENGTH: 15
<212> TYPE: RNA
<213> ORGANISM: Artificial Sequence
<220> FEATURE:
<223> OTHER INFORMATION: Description of Artificial Sequence: SYNTHETIC
      PEPTIDE

<400> SEQUENCE: 12
cagacagucc agguc                                                   15

<210> SEQ ID NO 13
<211> LENGTH: 48
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 13
agcttgacct gctgatgagc cgcttcggcg gcgaaactgt ctgatgca                48

<210> SEQ ID NO 14
<211> LENGTH: 40
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 14
tcagacagtt tcgccgccga agcggctcat cagcaggtca                        40

<210> SEQ ID NO 15
<211> LENGTH: 48
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 15
agcttgacct gctgctgacc cgcttcggcg gcgaaactgt ctgatgca                48

<210> SEQ ID NO 16
<211> LENGTH: 40
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 16
tcagacagtt tcgccgccga agcgggtcag cagcaggtca                        40

<210> SEQ ID NO 17

<210> SEQ ID NO 17
<211> LENGTH: 40
<212> TYPE: RNA
<213> ORGANISM: Artificial Sequence
<220> FEATURE:
<223> OTHER INFORMATION: Description of Artificial Sequence: SYNTHETIC
      PEPTIDE

<400> SEQUENCE: 17 cguuugcug augagccgcu ucggcggcga aacuugugga                                40

<210> SEQ ID NO 18
<211> LENGTH: 17
<212> TYPE: RNA
<213> ORGANISM: Artificial Sequence
<220> FEATURE:
<223> OTHER INFORMATION: Description of Artificial Sequence: SYNTHETIC
      PEPTIDE

<400> SEQUENCE: 18
uccacaaguc caaacag                                                       17

<210> SEQ ID NO 19
<211> LENGTH: 50
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 19
agcttctgtt tgctgatgag ccgcttcggc ggcgaaactt gtggaatgca                    50

<210> SEQ ID NO 20
<211> LENGTH: 42
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 20
ttccacaagt ttcgccgccg aagcggctca tcagcaaaca ga                            42

<210> SEQ ID NO 21
<211> LENGTH: 50
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 21
agcttctgtt tgctgctgac ccgcttcggc ggcgaaactt gtggaatgca                    50

<210> SEQ ID NO 22
<211> LENGTH: 42
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 22
ttccacaagt ttcgccgccg aagcgggtca gcagcaaaca ga                            42

<210> SEQ ID NO 23
<211> LENGTH: 40

```
<212> TYPE: RNA
<213> ORGANISM: Artificial Sequence
<220> FEATURE:
<223> OTHER INFORMATION: Description of Artificial Sequence: SYNTHETIC
      PEPTIDE

<400> SEQUENCE: 23
auccacacug augagccgcu ucggcggcga aacuccugug                            40

<210> SEQ ID NO 24
<211> LENGTH: 17
<212> TYPE: RNA
<213> ORGANISM: Artificial Sequence
<220> FEATURE:
<223> OTHER INFORMATION: Description of Artificial Sequence: SYNTHETIC
      PEPTIDE

<400> SEQUENCE: 24
cacaggaguc uguggau                                                    17

<210> SEQ ID NO 25
<211> LENGTH: 50
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 25
agcttatcca cactgatgag ccgcttcggc ggcgaaactc ctgtgatgca                 50

<210> SEQ ID NO 26
<211> LENGTH: 42
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 26
tcacaggagt ttcgccgccg aagcggctca tcagtgtgga ta                        42

<210> SEQ ID NO 27
<211> LENGTH: 16
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 27
ggactgtcag atatcg                                                     16

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 28
actgagtggg tggagactga                                                 20

<210> SEQ ID NO 29
<211> LENGTH: 34
<212> TYPE: RNA
```

<213> ORGANISM: Artificial Sequence
<220> FEATURE:
<223> OTHER INFORMATION: Description of Artificial Sequence: SYNTHETIC
      PEPTIDE

<400> SEQUENCE: 29
uucugccuga ugaggccgaa aggccgaaac guag                              34

<210> SEQ ID NO 30
<211> LENGTH: 13
<212> TYPE: RNA
<213> ORGANISM: Artificial Sequence
<220> FEATURE:
<223> OTHER INFORMATION: Description of Artificial Sequence: SYNTHETIC
      PEPTIDE

<400> SEQUENCE: 30
cuacguagca gaa                                                    13

<210> SEQ ID NO 31
<211> LENGTH: 35
<212> TYPE: RNA
<213> ORGANISM: Artificial Sequence
<220> FEATURE:
<223> OTHER INFORMATION: Description of Artificial Sequence: SYNTHETIC
      PEPTIDE

<400> SEQUENCE: 31
gaucaacuga ugagcgcuuc ggcgcgaaac cagaa                            35

<210> SEQ ID NO 32
<211> LENGTH: 14
<212> TYPE: RNA
<213> ORGANISM: Artificial Sequence
<220> FEATURE:
<223> OTHER INFORMATION: Description of Artificial Sequence: SYNTHETIC
      PEPTIDE

<400> SEQUENCE: 32
uucuggucuu gauc                                                   14

<210> SEQ ID NO 33
<211> LENGTH: 35
<212> TYPE: RNA
<213> ORGANISM: Artificial Sequence
<220> FEATURE:
<223> OTHER INFORMATION: Description of Artificial Sequence: SYNTHETIC
      PEPTIDE

<400> SEQUENCE: 33
guuugacuga ugagcgcuuc ggcgcgaaac aguuc                            35

<210> SEQ ID NO 34
<211> LENGTH: 14
<212> TYPE: RNA
<213> ORGANISM: Artificial Sequence
<220> FEATURE:
<223> OTHER INFORMATION: Description of Artificial Sequence: SYNTHETIC
      PEPTIDE

<400> SEQUENCE: 34
gaacugucuc aaac                                                   14

<210> SEQ ID NO 35
<211> LENGTH: 35
<212> TYPE: RNA
<213> ORGANISM: Artificial Sequence -continued

```
<220> FEATURE:
<223> OTHER INFORMATION: Description of Artificial Sequence: SYNTHETIC
      PEPTIDE

<400> SEQUENCE: 35
guggcucuga ugagccguuc gcggcgaaac cgaau                          35

<210> SEQ ID NO 36
<211> LENGTH: 14
<212> TYPE: RNA
<213> ORGANISM: Artificial Sequence
<220> FEATURE:
<223> OTHER INFORMATION: Description of Artificial Sequence: SYNTHETIC
      PEPTIDE

<400> SEQUENCE: 36
auucggucag ccac                                                 14

<210> SEQ ID NO 37
<211> LENGTH: 35
<212> TYPE: RNA
<213> ORGANISM: Artificial Sequence
<220> FEATURE:
<223> OTHER INFORMATION: Description of Artificial Sequence: SYNTHETIC
      PEPTIDE

<400> SEQUENCE: 37
cuucugcuga ugagccguuc gcggcgaaac ucugu                          35

<210> SEQ ID NO 38
<211> LENGTH: 14
<212> TYPE: RNA
<213> ORGANISM: Artificial Sequence
<220> FEATURE:
<223> OTHER INFORMATION: Description of Artificial Sequence: SYNTHETIC
      PEPTIDE

<400> SEQUENCE: 38
acagagucca gaag                                                 14

<210> SEQ ID NO 39
<211> LENGTH: 34
<212> TYPE: RNA
<213> ORGANISM: Artificial Sequence
<220> FEATURE:
<223> OTHER INFORMATION: Description of Artificial Sequence: SYNTHETIC
      PEPTIDE

<400> SEQUENCE: 39
augauucuga ugaguccgaa aggacgaaac agcc                           34

<210> SEQ ID NO 40
<211> LENGTH: 13
<212> TYPE: RNA
<213> ORGANISM: Artificial Sequence
<220> FEATURE:
<223> OTHER INFORMATION: Description of Artificial Sequence: SYNTHETIC
      PEPTIDE

<400> SEQUENCE: 40
ggcugucaau cau                                                  13

<210> SEQ ID NO 41
<211> LENGTH: 34
<212> TYPE: RNA
<213> ORGANISM: Artificial Sequence
<220> FEATURE:
```

```
<223> OTHER INFORMATION: Description of Artificial Sequence: SYNTHETIC
      PEPTIDE

<400> SEQUENCE: 41
aucuugcuga ugaguccgaa aggacgaaac ccgu                                34

<210> SEQ ID NO 42
<211> LENGTH: 13
<212> TYPE: RNA
<213> ORGANISM: Artificial Sequence
<220> FEATURE:
<223> OTHER INFORMATION: Description of Artificial Sequence: SYNTHETIC
      PEPTIDE

<400> SEQUENCE: 42
acggguccaa gau                                                       13

<210> SEQ ID NO 43
<211> LENGTH: 34
<212> TYPE: RNA
<213> ORGANISM: Artificial Sequence
<220> FEATURE:
<223> OTHER INFORMATION: Description of Artificial Sequence: SYNTHETIC
      PEPTIDE

<400> SEQUENCE: 43
cauccucuga ugaguccgaa aggacgaaac aucu                                34

<210> SEQ ID NO 44
<211> LENGTH: 13
<212> TYPE: RNA
<213> ORGANISM: Artificial Sequence
<220> FEATURE:
<223> OTHER INFORMATION: Description of Artificial Sequence: SYNTHETIC
      PEPTIDE

<400> SEQUENCE: 44
agaugucagg aug                                                       13

<210> SEQ ID NO 45
<211> LENGTH: 34
<212> TYPE: RNA
<213> ORGANISM: Artificial Sequence
<220> FEATURE:
<223> OTHER INFORMATION: Description of Artificial Sequence: SYNTHETIC
      PEPTIDE

<400> SEQUENCE: 45
uugucacuga ugaguccgaa aggacgaaac aaug                                34

<210> SEQ ID NO 46
<211> LENGTH: 13
<212> TYPE: RNA
<213> ORGANISM: Artificial Sequence
<220> FEATURE:
<223> OTHER INFORMATION: Description of Artificial Sequence: SYNTHETIC
      PEPTIDE

<400> SEQUENCE: 46
cauugucuga caa                                                       13

<210> SEQ ID NO 47
<211> LENGTH: 34
<212> TYPE: RNA
<213> ORGANISM: Artificial Sequence
<220> FEATURE:
<223> OTHER INFORMATION: Description of Artificial Sequence: SYNTHETIC
```

```
                        PEPTIDE

<400> SEQUENCE: 47
gcgauucuga ugagcgcuuc ggcgcgaaac ucca                              34

<210> SEQ ID NO 48
<211> LENGTH: 13
<212> TYPE: RNA
<213> ORGANISM: Artificial Sequence
<220> FEATURE:
<223> OTHER INFORMATION: Description of Artificial Sequence: SYNTHETIC
      PEPTIDE

<400> SEQUENCE: 48
uggagucaau cgc                                                    13

<210> SEQ ID NO 49
<211> LENGTH: 34
<212> TYPE: RNA
<213> ORGANISM: Artificial Sequence
<220> FEATURE:
<223> OTHER INFORMATION: Description of Artificial Sequence: SYNTHETIC
      PEPTIDE

<400> SEQUENCE: 49
ucaaaacuga ugagcgcuuc ggcgcgaaac ccaa                              34

<210> SEQ ID NO 50
<211> LENGTH: 13
<212> TYPE: RNA
<213> ORGANISM: Artificial Sequence
<220> FEATURE:
<223> OTHER INFORMATION: Description of Artificial Sequence: SYNTHETIC
      PEPTIDE

<400> SEQUENCE: 50
uugggucuuu uga                                                    13

<210> SEQ ID NO 51
<211> LENGTH: 34
<212> TYPE: RNA
<213> ORGANISM: Artificial Sequence
<220> FEATURE:
<223> OTHER INFORMATION: Description of Artificial Sequence: SYNTHETIC
      PEPTIDE

<400> SEQUENCE: 51
uuucagcuga ugagcgcuuc ggcgcgaaac gaau                              34

<210> SEQ ID NO 52
<211> LENGTH: 13
<212> TYPE: RNA
<213> ORGANISM: Artificial Sequence
<220> FEATURE:
<223> OTHER INFORMATION: Description of Artificial Sequence: SYNTHETIC
      PEPTIDE

<400> SEQUENCE: 52
auucguccug aaa                                                    13

<210> SEQ ID NO 53
<211> LENGTH: 34
<212> TYPE: RNA
<213> ORGANISM: Artificial Sequence
<220> FEATURE:
<223> OTHER INFORMATION: Description of Artificial Sequence: SYNTHETIC
      PEPTIDE
```

```
<400> SEQUENCE: 53
aucaaucuga ugagcgcuuc ggcgcgaaac uuca                              34

<210> SEQ ID NO 54
<211> LENGTH: 13
<212> TYPE: RNA
<213> ORGANISM: Artificial Sequence
<220> FEATURE:
<223> OTHER INFORMATION: Description of Artificial Sequence: SYNTHETIC
      PEPTIDE

<400> SEQUENCE: 54
ugaagucauu gau                                                    13

<210> SEQ ID NO 55
<211> LENGTH: 34
<212> TYPE: RNA
<213> ORGANISM: Artificial Sequence
<220> FEATURE:
<223> OTHER INFORMATION: Description of Artificial Sequence: SYNTHETIC
      PEPTIDE

<400> SEQUENCE: 55
agugagcuga ugagccguuc gcggcgaaac cugc                             34

<210> SEQ ID NO 56
<211> LENGTH: 13
<212> TYPE: RNA
<213> ORGANISM: Artificial Sequence
<220> FEATURE:
<223> OTHER INFORMATION: Description of Artificial Sequence: SYNTHETIC
      PEPTIDE

<400> SEQUENCE: 56
gcagguccuc acu                                                    13

<210> SEQ ID NO 57
<211> LENGTH: 34
<212> TYPE: RNA
<213> ORGANISM: Artificial Sequence
<220> FEATURE:
<223> OTHER INFORMATION: Description of Artificial Sequence: SYNTHETIC
      PEPTIDE

<400> SEQUENCE: 57
ucaauacuga ugagccguuc gcggcgaaac acau                             34

<210> SEQ ID NO 58
<211> LENGTH: 13
<212> TYPE: RNA
<213> ORGANISM: Artificial Sequence
<220> FEATURE:
<223> OTHER INFORMATION: Description of Artificial Sequence: SYNTHETIC
      PEPTIDE

<400> SEQUENCE: 58
augugucuau uga                                                    13

<210> SEQ ID NO 59
<211> LENGTH: 34
<212> TYPE: RNA
<213> ORGANISM: Artificial Sequence
<220> FEATURE:
<223> OTHER INFORMATION: Description of Artificial Sequence: SYNTHETIC
      PEPTIDE
```

```
<400> SEQUENCE: 59
uucaugcuga ugagccguuc gcggcgaaac cacc                          34

<210> SEQ ID NO 60
<211> LENGTH: 13
<212> TYPE: RNA
<213> ORGANISM: Artificial Sequence
<220> FEATURE:
<223> OTHER INFORMATION: Description of Artificial Sequence: SYNTHETIC
      PEPTIDE

<400> SEQUENCE: 60
ggugguccau gaa                                                 13

<210> SEQ ID NO 61
<211> LENGTH: 34
<212> TYPE: RNA
<213> ORGANISM: Artificial Sequence
<220> FEATURE:
<223> OTHER INFORMATION: Description of Artificial Sequence: SYNTHETIC
      PEPTIDE

<400> SEQUENCE: 61
ccaaaccuga ugagccguuc gcggcgaaac uucc                          34

<210> SEQ ID NO 62
<211> LENGTH: 13
<212> TYPE: RNA
<213> ORGANISM: Artificial Sequence
<220> FEATURE:
<223> OTHER INFORMATION: Description of Artificial Sequence: SYNTHETIC
      PEPTIDE

<400> SEQUENCE: 62
ggaagucguu ugg                                                 13

<210> SEQ ID NO 63
<211> LENGTH: 37
<212> TYPE: RNA
<213> ORGANISM: Artificial Sequence
<220> FEATURE:
<223> OTHER INFORMATION: Description of Artificial Sequence: SYNTHETIC
      PEPTIDE

<400> SEQUENCE: 63
uaugcuacug augagccgcu cggcggcga aacggua                        37

<210> SEQ ID NO 64
<211> LENGTH: 14
<212> TYPE: RNA
<213> ORGANISM: Artificial Sequence
<220> FEATURE:
<223> OTHER INFORMATION: Description of Artificial Sequence: SYNTHETIC
      PEPTIDE

<400> SEQUENCE: 64
uaccgucuag caua                                                14

<210> SEQ ID NO 65
<211> LENGTH: 720
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 65
```

```
ctggctctta acggcgttta tgtcctttgc tgtctgaggg gcctcagctc tgaccaatct    60
ggtcttcgtg tggtcattag catgggcttc gtgagacaga tacagctttt gctctggaag   120
aactggaccc tgcggaaaag gcaaaagatt cgctttgtgg tggaactcgt gtggccttta   180
tctttatttc tggtcttgat ctggttaagg aatgccaacc cgctctacag ccatcatgaa   240
tgccatttcc ccaacaaggc gatgccctca gcaggaatgc tgccgtggct ccaggggatc   300
ttctgcaatg tgaacaatcc ctgttttcaa agccccaccc caggagaatc tcctggaatt   360
gtgtcaaact ataacaactc catcttggca agggtatatc gagatttttca agaactcctc   420 atgaatgcac cagagagcca gcaccttggc cgtatttgga cagagctaca catcttgtcc   480
caattcatgg acaccctccg gactcacccg gagagaattg caggaagagg aatacgaata   540
agggatatct tgaaagatga agaaacactg acactatttc tcattaaaaa catcggcctg   600
tctgactcag tggtctacct tctgatcaac tctcaagtcc gtccagagca gttcgctcat   660
ggagtcccgg acctggcgct gaaggacatc gcctgcagcg aggccctcct ggagcgcttc   720
```

```
<210> SEQ ID NO 66
<211> LENGTH: 14
<212> TYPE: RNA
<213> ORGANISM: Artificial Sequence
<220> FEATURE:
<223> OTHER INFORMATION: Description of Artificial Sequence: SYNTHETIC
      PEPTIDE
<220> FEATURE:
<221> NAME/KEY: misc_feature
<222> LOCATION: (1)..(14)
<223> OTHER INFORMATION: where n = a, g, c or u
<220> FEATURE:
<221> NAME/KEY: misc_feature
<222> LOCATION: (4)
<223> OTHER INFORMATION: where b = g, c or u

<400> SEQUENCE: 66
nnnbngucnn nnnn                                                       14

<210> SEQ ID NO 67
<211> LENGTH: 46
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 67
agcttatgct actgatgagc cgcttcggcg gcgaaacggt aatgca                    46

<210> SEQ ID NO 68
<211> LENGTH: 38
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 68
ttaccgtttc gccgccgaag cggctcatca gtagcata                             38

<210> SEQ ID NO 69
<211> LENGTH: 34
<212> TYPE: DNA
<213> ORGANISM: Artificial Sequence
<220> FEATURE:
<223> OTHER INFORMATION: Description of Artificial Sequence: SYNTHETIC
```

OLIGONUCLEOTIDE

<400> SEQUENCE: 69
gcgattctga tgagcgcttc ggcgcgaaac tcca                               34

<210> SEQ ID NO 70
<211> LENGTH: 42
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 70
agctgcgatt ctgatgagcg cttcggcgcg aaactccatg ca                     42

<210> SEQ ID NO 71
<211> LENGTH: 34
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 71
tggagtttcg cgccgaagcg ctcatcagaa tcgc                              34

<210> SEQ ID NO 72
<211> LENGTH: 34
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 72
tggagtttcg cgccgaagcg ctcatcagaa tcgc                              34

<210> SEQ ID NO 73
<211> LENGTH: 34
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 73
tcaaaactga tgagcgcttc ggcgcgaaac ccaa                              34

<210> SEQ ID NO 74
<211> LENGTH: 42
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 74
agcttcaaaa ctgatgagcg cttcggcgcg aaacccaatg ca                     42

<210> SEQ ID NO 75
<211> LENGTH: 34
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 75
ttgggtttcg cgccgaagcg ctcatcagtt ttga         34

<210> SEQ ID NO 76
<211> LENGTH: 34
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 76
ttgggtttcg cgccgaagcg ctcatcagct gaaa         34

<210> SEQ ID NO 77
<211> LENGTH: 32
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 77
tatttctggt cttgatctgg ttaaggaatg cc           32

<210> SEQ ID NO 78
<211> LENGTH: 32
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 78
ggcattcctt aaccagatca agaccagaaa ta           32

<210> SEQ ID NO 79
<211> LENGTH: 14
<212> TYPE: RNA
<213> ORGANISM: Artificial Sequence
<220> FEATURE:
<223> OTHER INFORMATION: Description of Artificial Sequence: SYNTHETIC
      PEPTIDE

<400> SEQUENCE: 79
uucuggucuu gauc                               14

<210> SEQ ID NO 80
<211> LENGTH: 57
<212> TYPE: RNA
<213> ORGANISM: Artificial Sequence
<220> FEATURE:
<223> OTHER INFORMATION: Description of Artificial Sequence: SYNTHETIC
      PEPTIDE

<400> SEQUENCE: 80
ggccgaauuc gaucaacuga ugagccgcuu cggcggcgaa accagaaacg cgucgcg    57

<210> SEQ ID NO 81
<211> LENGTH: 57
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 81
ggccgaattc gatcaactga tgagccgctt cggcggcgaa accagaaacg cgtcgcg    57

<210> SEQ ID NO 82
<211> LENGTH: 57
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 82
cgcgacgcgt ttctggtttc gccgccgaag cggctcatca gttgatcgaa ttcggcc    57

<210> SEQ ID NO 83
<211> LENGTH: 34
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 83
tttcagctga tgagcgcttc ggcgcgaaac gaat    34

<210> SEQ ID NO 84
<211> LENGTH: 42
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 84
agcttttcag ctgatgagcg cttcggcgcg aaacgaattg ca    42

<210> SEQ ID NO 85
<211> LENGTH: 34
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 85
attcgtttcg cgccgaagcg ctcatcagct gaaa    34

<210> SEQ ID NO 86
<211> LENGTH: 34
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 86
attcgtttcg cgccgaagcg ctcatcagct gaaa    34

<210> SEQ ID NO 87
<211> LENGTH: 34
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 87
atcaatctga tgagcgcttc ggcgcgaaac ttca                    34

<210> SEQ ID NO 88
<211> LENGTH: 42
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 88
agctatcaat ctgatgagcg cttcggcgcg aaacttcatg ca           42

<210> SEQ ID NO 89
<211> LENGTH: 34
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 89
tgaagtttcg cgccgaagcg ctcatcagct tgat                    34

<210> SEQ ID NO 90
<211> LENGTH: 34
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 90
tgaagtttcg cgccgaagcg ctcatcagct tgat                    34

<210> SEQ ID NO 91
<211> LENGTH: 44
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 91
agcttagtga gctgatgagc cgttcgcggc gaaacctgca tgca          44

<210> SEQ ID NO 92
<211> LENGTH: 36
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 92
tgcaggtttc gccgcgaacg gctcatcagc tcacta                  36

<210> SEQ ID NO 93
<211> LENGTH: 44
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 93

```
agctttcaat actgatgagc cgttcgcggc gaaacacata tgca         44
```

<210> SEQ ID NO 94
<211> LENGTH: 36
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 94

```
tatgtgtttc gccgccaacg gctcatcagt attgaa                  36
```

<210> SEQ ID NO 95
<211> LENGTH: 44
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 95

```
agcttttcat gctgatgagc cgttcgcggc gaaaccacca tgca         44
```

<210> SEQ ID NO 96
<211> LENGTH: 36
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 96

```
tggtggtttc gccgcgaacg gctcatcagc atgaaa                  36
```

<210> SEQ ID NO 97
<211> LENGTH: 44
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 97

```
agcttccaaa cctgatgagc cgttcgcggc gaaacttcca tgca         44
```

<210> SEQ ID NO 98
<211> LENGTH: 36
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE

<400> SEQUENCE: 98

```
tggaagtttc gccgcgaacg gctcatcagg tttgga                  36
```

ADENO-ASSOCIATED VIRUS-DELIVERED RIBOZYME COMPOSITIONS AND METHODS OF USE

The present application is a divisional of currently pending application Ser. No. 09/561,498, filed Apr. 28, 2000, which claims the benefit of provisional patent application Ser. No. 60/131,942 filed Apr. 30, 1999, the entire contents of which is specifically incorporated herein by reference in its entirety.

The United States government has certain rights in the present invention pursuant to Grant Numbers EY11596 from the National Institutes of Health.

1.0 BACKGROUND OF THE INVENTION 1.1 Field of the Invention

The present invention relates generally to the fields of genetics, molecular and cellular biology and medicine. More particularly, it concerns identification of novel genes involved in a variety of cellular processes, including retinal degeneration, cancer, memory and learning, and identification of the function of a variety of genes and gene fragments of unknown function. The genes thus identified, as well as the compositions used in the identification methods, are also disclosed.

1.2 Description of the Related Art

Recent advances in human genome research, assisted by the advent of automated DNA sequencing, have yielded a wealth of knowledge about human genes and proteins. Advances in gene sequencing and gene isolation, combined with computer-based bioinformation systems and analysis, offer the potential for many new treatments.

Advances in genomics and combinatorial chemistry have revolutionized the way drugs are discovered. With sequencing and characterization of the 100,000 human genes only a few years away, random compound screening is being replaced by identifying disease-associated genes, followed by rational drug design to specifically target gene products that are involved in the disease pathway. However, the sheer volume of genetic information being produced means that the problem of finding a new genetic target is being replaced by the problem of determining which of the many new targets are the best.

Through the efforts of the Human Genome Project, academic centers and the biopharmaceutical industry, there is now a significant amount of gene sequence information available to researchers. However, while this information is accessible, knowing a gene sequence alone, without an understanding of its biological function, is not usually enough to enable effective drug development. What is needed, and is presently lacking in the art, are methods of identifying the particular gene or genes involved in selected biological and physiological processes. This lack of adequate technologies to accomplish in vivo target validation currently represents a major roadblock in the translation of gene sequence information emerging from the Human Genome Project into new therapeutic targets.

2.0 SUMMARY OF THE INVENTION

The present invention overcomes these and other deficiencies in the art by providing methods for the identification of novel genes that are involved, either directly or indirectly, in a variety of cellular, biological and physiological processes. Additionally, the present invention overcomes other shortcomings of the art by providing methods for identifying the function of previously identified genes or gene fragments, such as expressed sequence tags (ESTs), which heretofore has been both difficult and extremely time consuming and labor intensive. The present invention provides methods to "knock-out", or inactivate, genes of unknown function in any cell, or more importantly somatic tissue, and obtain evidence of the function of the genes based on the resulting "knock-out" phenotype. These methods are also useful in testing genes of known or suspected function for their disease-causing potential, thereby identifying new disease-causing genes. The present invention provides significant advantages over traditional gene disruptions in embryonic stem cells, as genes that are critical to development and lead to embryonic lethality can be "knocked-out" in adult animals and studied using the methods provided herein. Thus, the present invention also overcomes further deficiencies in the art by providing animal models of a variety of different physiological conditions, including certain inborn errors, and diseases.

The present invention provides methods of identifying one or more genes having a selected function, comprising contacting a plurality of genes suspected of comprising the gene with a plurality or library of ribozymes, and identifying one or more ribozymes from the plurality or library that alter the selected function of the one or more genes, thereby identifying one or more genes having the selected function.

In preferred aspects of the invention, the gene or genes to be identified are involved in one or more cellular, biological and/or physiological process. The processes can be life threatening, for example acquired or in-born diseases such as cancer, degenerative, such retinal degeneration, impaired learning or long or short-term memory loss, or any other normal or abnormal process of interest.

In various embodiments the plurality of genes are comprised within an animal, for example a mammal or a human subject. However, this is not essential, and thus in other embodiments the plurality of genes are provided in an ex vivo setting, for example in tissue culture or cell culture, or in an in vitro setting, using crude, partially isolated or purified nucleic acids.

The library of ribozymes comprises a plurality of ribozymes that comprise degenerate bases within the region of the ribozyme involved in target recognition and binding of the ribozyme to its target nucleic acid. In certain aspects of the present invention the ribozymes are completely degenerate at these recognition and binding positions, having the sequence shown in SEQ ID NO:1, while in other aspects of the invention the ribozymes have completely or partially (only two or three of the possible four ribonucleotide bases) degenerate bases at one, two, three four, five, six, seven, eight, nine or ten positions or so. All types of ribozymes, including hammerhead, hairpin, a hepatitis δ virus, group I intron or RNaseP RNA (in association with an RNA guide sequence) or Neurospora VS RNA motifs are contemplated for use in the present invention, although in certain preferred aspects the ribozymes are hammerhead ribozymes. In various aspects of the invention, the ribozymes are chemically synthesized or transcribed either in vitro or in vivo.

The ribozymes can be delivered by a variety of different method, as described herein below, but in preferred aspects of the invention, the ribozymes or library of ribozymes are cloned into an adeno-associated viral expression vector, and comprised within a plurality of adeno-associated virus particles.

In preferred aspects of the present invention, the one or more ribozymes and/or the one or more genes identified by the present methods are isolated, and in certain aspects of the invention, the nucleotide sequence of all or a portion of the ribozymes and/or genes is obtained.

Thus, the present invention provides a method of identifying at least a first gene involved in retinal degeneration, comprising contacting a plurality of genes suspected of comprising the at least a first gene with a library of ribozymes, and identifying at least a first ribozyme from the library that alters retinal degeneration, thereby identifying the at least a first gene involved in retinal degeneration. One ribozyme contemplated for use in identifying genes involved in retinal degeneration has the nucleotide sequence of SEQ ID NO:29. Among the genes that can be thus identified are rhodopsin genes and genes encoding the β-subunit of cGMP phosphodiesterase.

The present invention also provides a method of identifying at least a first tumor suppressor gene, comprising contacting a plurality of genes suspected of comprising the at least a first tumor suppressor gene with a library of ribozymes, and identifying at least a first ribozyme from the library that alters tumor suppression, thereby identifying the at least a first tumor suppressor gene. Ribozymes contemplated for use in identifying tumor suppressor genes include, but are not limited to, those having the nucleotide sequence of SEQ ID NO:3, SEQ ID NO:5, SEQ ID NO:7 and SEQ ID NO:9. Examples of genes that can be identified using these methods include, but are not limited to, a p53 gene, a p16 gene, a retinoblastoma gene and a p19ARF gene.

The present invention also provides a method of identifying at least a first gene involved in amyotrophic lateral sclerosis disease, comprising contacting a plurality of genes suspected of comprising the at least a first gene with a library of ribozymes, and identifying at least a first ribozyme from the library that is involved amyotrophic lateral sclerosis disease, thereby identifying the at least a first gene involved in causing such a disorder in a mammal. Ribozymes contemplated for use in identifying genes involved in ALS include, but are not limited to, those having a nucleotide sequence comprising all or a portion of a gene encoding superoxide dismutase or a manganese superoxide dismutase.

The present invention also provides a method of identifying at least a first gene involved in amyotrophic lateral sclerosis disease, comprising contacting a plurality of genes suspected of comprising the at least a first gene with a library of ribozymes, and identifying at least a first ribozyme from the library that is involved amyotrophic lateral sclerosis disease, thereby identifying the at least a first gene involved in causing such a disorder in a mammal. Ribozymes contemplated for use in identifying genes involved in ALS include, but are not limited to, those having a nucleotide sequence comprising all or a portion of a gene encoding superoxide dismutase or a manganese superoxide dismutase.

The present invention also provides the isolated genes and ribozymes identified by the methods provided herein. Thus, genes and ribozymes that are involved in or alter retinal degeneration, retinal disease, memory, learning, ALS, and tumor suppressor genes, identified by these methods, are provided by the present invention.

In certain aspects of the present invention, a ribozyme is designed based upon a small fragment of a gene, for example an EST, where the function of the gene from which the EST is derived is either known or unknown, and where the full length gene has not yet been cloned. The present invention provides a method of identifying an essentially full-length gene having a selected function, comprising contacting a plurality of genes suspected of comprising the essentially full-length gene with at least a first ribozyme that cleaves the ribonucleic acid of the essentially full-length gene, thereby identifying the essentially full-length gene having the selected function.

Since certain ribozymes provided by the present invention have been designed to target specific or particular genes, the present invention provides a method of identifying these specific or particular genes, comprising contacting a plurality of genes suspected of comprising the specific gene with at least a first ribozyme that cleaves the ribonucleic acid of the specific gene, thereby identifying the specific or particular gene. Thus, the present invention provides methods for identifying a rhodopsin gene, a gene encoding the γ- or the β-subunit of cGMP phosphodiesterase, a p53 gene, a p16 gene, a retinoblastoma gene, a p19ARF gene, a gene encoding a subunit of NADH dehydrogenase, a superoxide dismutase- or a manganese superoxide dismutase-encoding gene, and/or a CREB gene.

Additionally, the present invention provides a method of identifying a function of a selected gene, comprising contacting a plurality of genes suspected of comprising the selected gene with a ribozyme that cleaves the ribonucleic acid of the selected gene, and identifying the effect of the ribozyme, thereby identifying the function of the selected gene.

The present invention also provides a method of inducing a selected physiologically abnormal condition in an animal, comprising administering to the animal at least a first ribozyme that cleaves the ribonucleic acid of at least a first gene involved in preventing the selected physiologically abnormal condition, thereby inducing the selected physiologically abnormal condition in the animal. In certain methods, the physiologically abnormal condition is retinal degeneration, cancer, memory loss or impaired learning. Thus, the present invention also provides an animal in which any particular gene of interest has been inactivated, thereby providing animal models for a variety of different abnormal conditions and diseases. Likewise, the present invention provides a method of inducing a selected physiologically abnormal condition in an animal, comprising administering to the animal at least a first ribozyme that cleaves the ribonucleic acid of at least a first gene involved in causing the selected physiologically abnormal condition, thereby inducing the selected physiologically abnormal condition in the animal. Thus, the present invention also provides methods for creating non-human animal models in which any particular gene of interest has been inactivated, thereby providing tools for the study of a variety of different abnormal conditions and diseases.

3.0 BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein:

Figure 11:
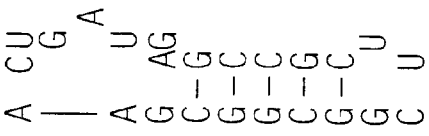

FIG. 11 shows the nucleotide sequence (SEQ ID NO:11) and structure of a CREB 230 hammerhead ribozyme, including RNA target sequence (SEQ ID NO:12; CREB 230). Also shown are the oligonucleotides used to clone the CREB230 ribozyme (SEQ ID NO:13 and SEQ ID NO:14), and the oligonucleotides used to clone a mutant, inactive form of the CREB230 ribozyme (SEQ ID NO:15 and SEQ ID NO:16).

FIG. 12 shows the nucleotide sequence (SEQ ID NO:17) and structure of a CREB 288 hammerhead ribozyme, including RNA target sequence (SEQ ID NO:18; CREB 288). Also shown are the oligonucleotides used to clone the CREB288 ribozyme (SEQ ID NO:19 and SEQ ID NO:20), and the oligonucleotides used to clone a mutant, inactive form of the CREB288 ribozyme (SEQ ID NO:21 and SEQ ID NO:22).

Figure 13:
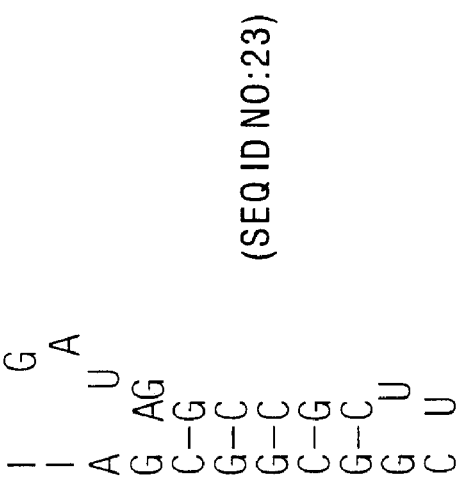

FIG. 13 shows the nucleotide sequence (SEQ ID NO:23) and structure of a CREB 380 hammerhead ribozyme, including RNA target sequence (SEQ ID NO:24; CREB 380). Also shown are the oligonucleotides used to clone the CREB380 ribozyme (SEQ ID NO:25 and SEQ ID NO:26).

Figure 14:
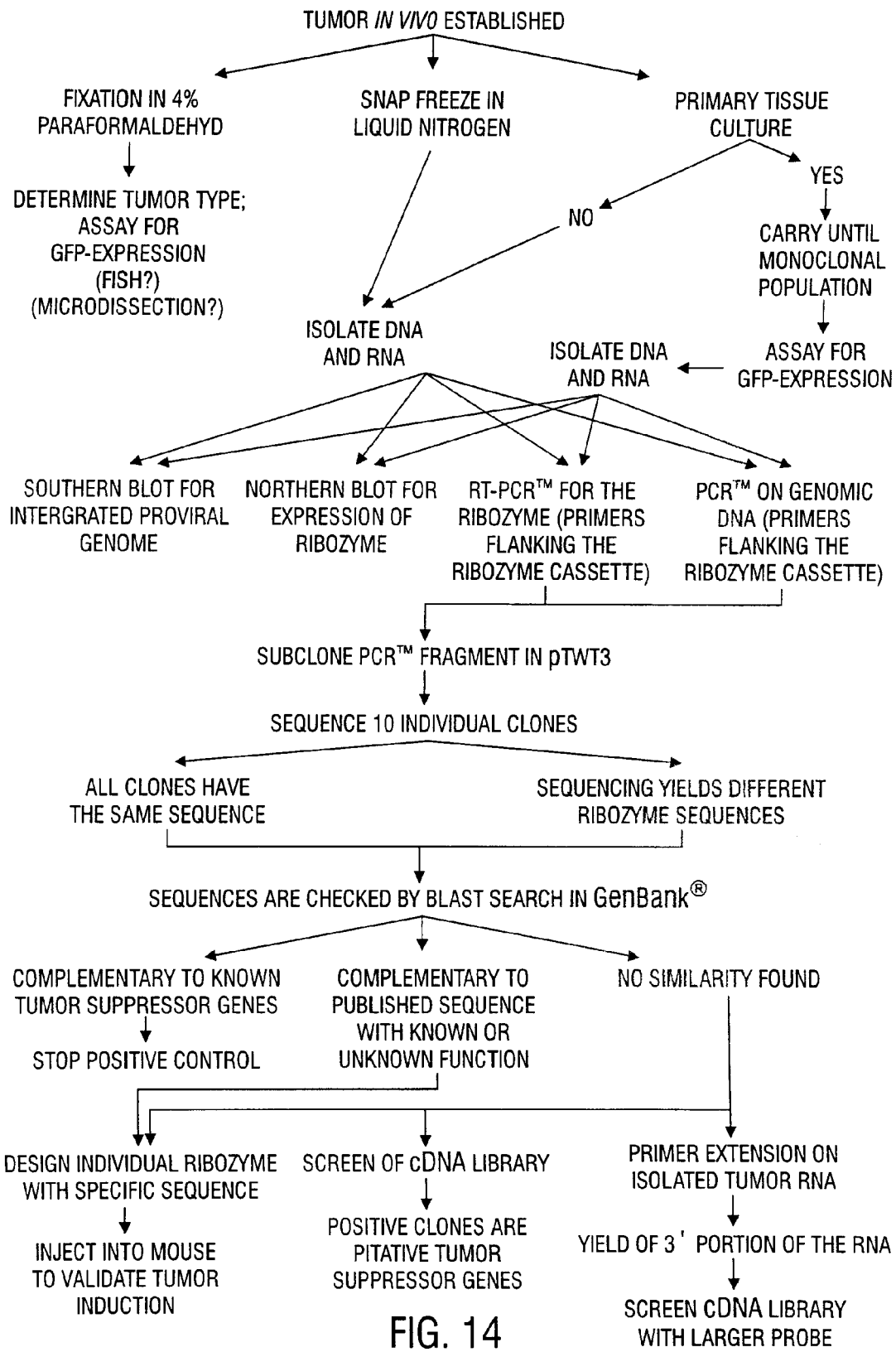

FIG. 14 illustrates a flow sheet for candidate tumor suppressor genes.

FIG. 15 shows the nucleotide sequence (SEQ ID NO:29) and structure of an anti-β-subunit of cGMP phosphodiesterase (βPDE) hammerhead ribozyme, including RNA target sequence (SEQ ID NO:30; nt 1037-1049 of the murine βPDE).

FIG. 16A, FIG. 16B, FIG. 16C and FIG. 16D illustrate micrographs of outer nuclear layers of treated and control eyes. FIG. 16A. Control eye (left) injected with PBS. FIG. 16B. Right eye of same mouse as that shown in FIG. 16A, injected with a ribozyme against the β-subunit of cGMP phosphodiesterase (βPDE). FIG. 16C. Control eye (left), injected with an inactive form of a ribozyme against βPDE. FIG. 16D. Right eye of same mouse as that shown in FIG. 16C, injected with an active ribozyme against βPDE.

FIG. 17A shows the nucleotide sequence (SEQ ID NO:31) and structure of an anti-ABCR hammerhead ribozyme, including RNA target sequence (SEQ ID NO:32 of the human ABCR gene).

FIG. 17B shows the nucleotide sequence (SEQ ID NO:33) and structure of an anti-ABCR hammerhead ribozyme, including RNA target sequence (SEQ ID NO:34 of the mouse ABCR gene).

Figure 18A:
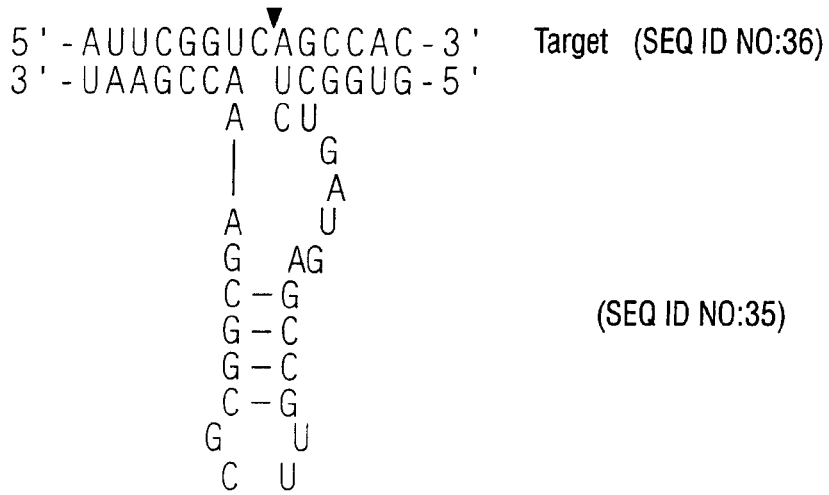

FIG. 18A shows the nucleotide sequence (SEQ ID NO:35) and structure of an anti-γPDE hammerhead ribozyme, including RNA target sequence (SEQ ID NO:36 of the mouse γPDE gene).

Figure 18B:
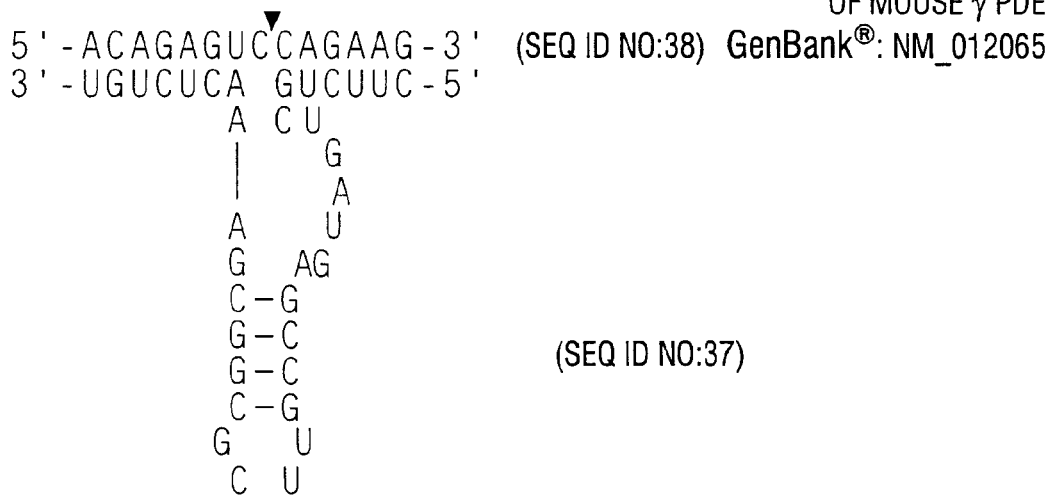

FIG. 18B shows the nucleotide sequence (SEQ ID NO:37) and structure of an anti-γPDE hammerhead ribozyme, including RNA target sequence (SEQ ID NO:38) of the mouse γPDE gene).

Figure 19:
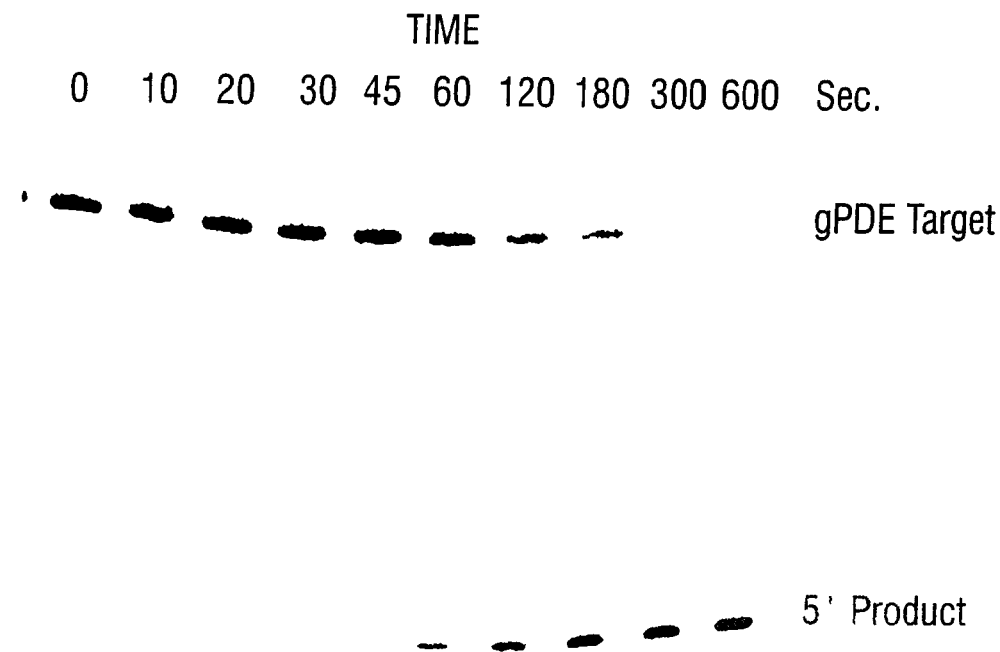

FIG. 19 shows the time course of cleavage by HHRZ 42.

Figure 20:
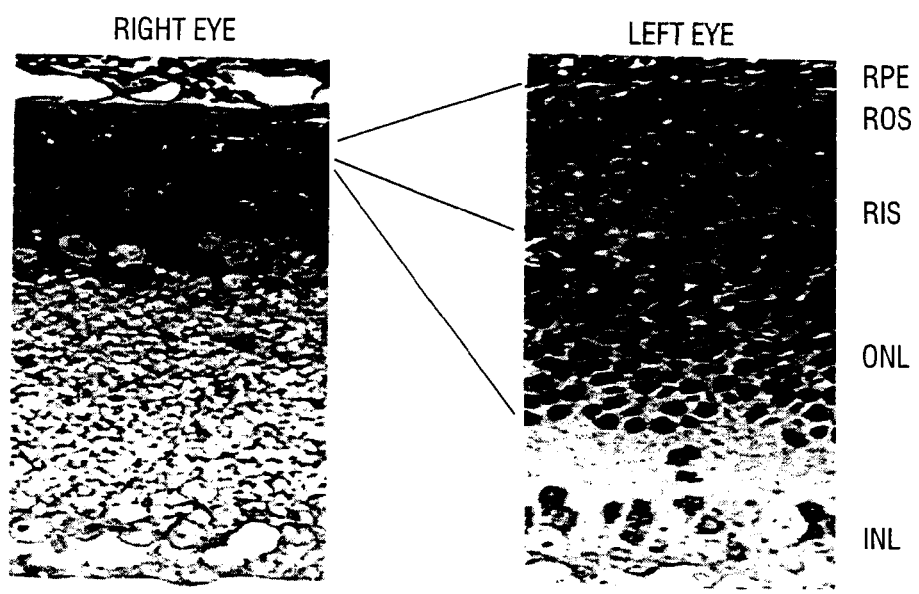

FIG. 20 shows light micrographs of the retina from a wild type mouse C57BL/6(+/+, WF12) with 8 weeks after subretinal injection. R-eye, injected with pHRz35+pHRz42 ribozymes, has decreased more than 90% in its ONL, ROS and RIS thickness compared to L-eye, control eye injected with PBS.

Figure 21A:
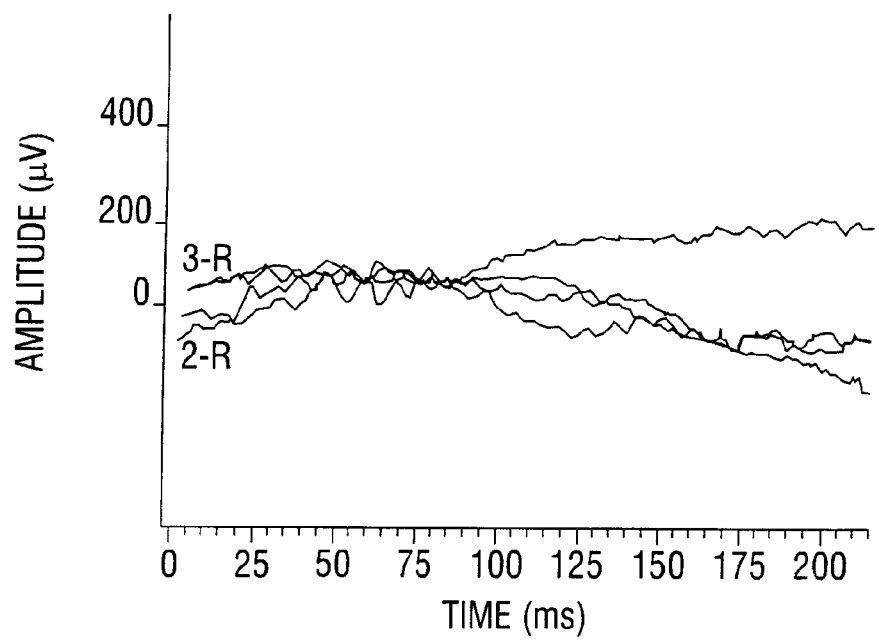
Figure 21B:
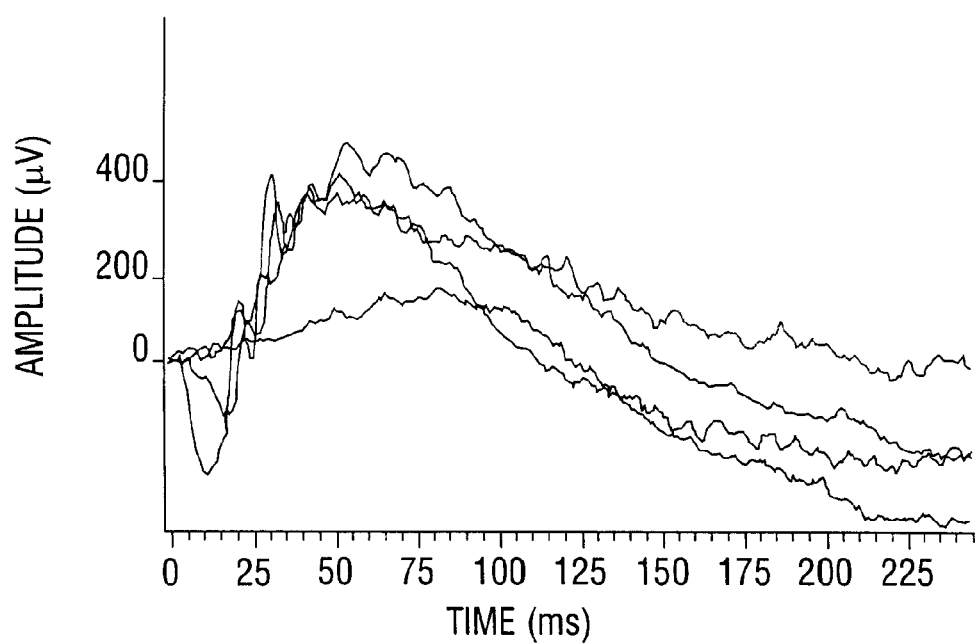

FIG. 21 shows scotopic (ROD) ERG waveforms for right and left eyes of wild type γPDE Rz in +/−mouse at 6 weeks p.i. Flash intensities are −1.1, −0.1, 0.9, 1.9 log cd-s-m$^2$.

Figure 22:
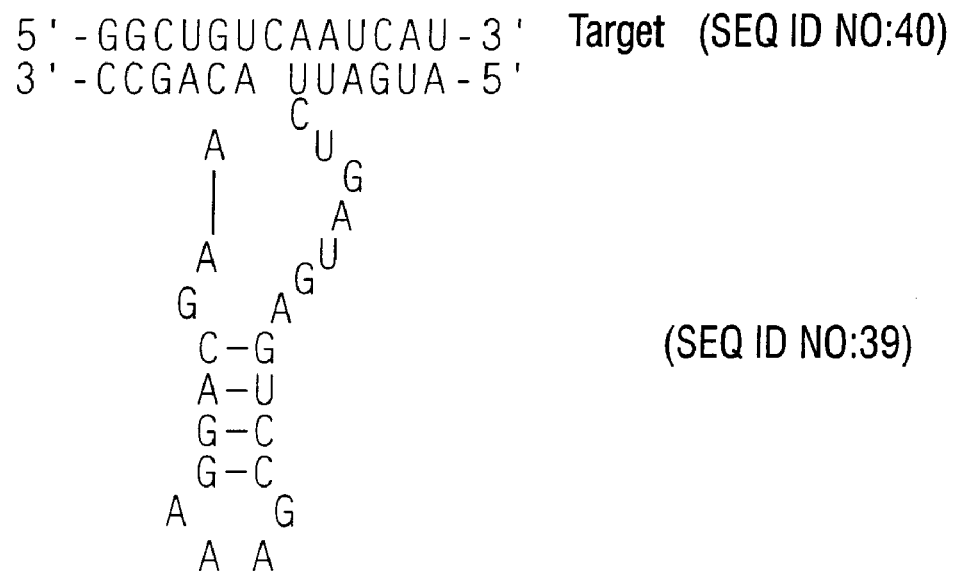

FIG. 22 shows the nucleotide sequence (SEQ ID NO:39) and structure of an anti-IT15-2Rz hammerhead ribozyme, including RNA target sequence (SEQ ID NO:40).

Figure 23:
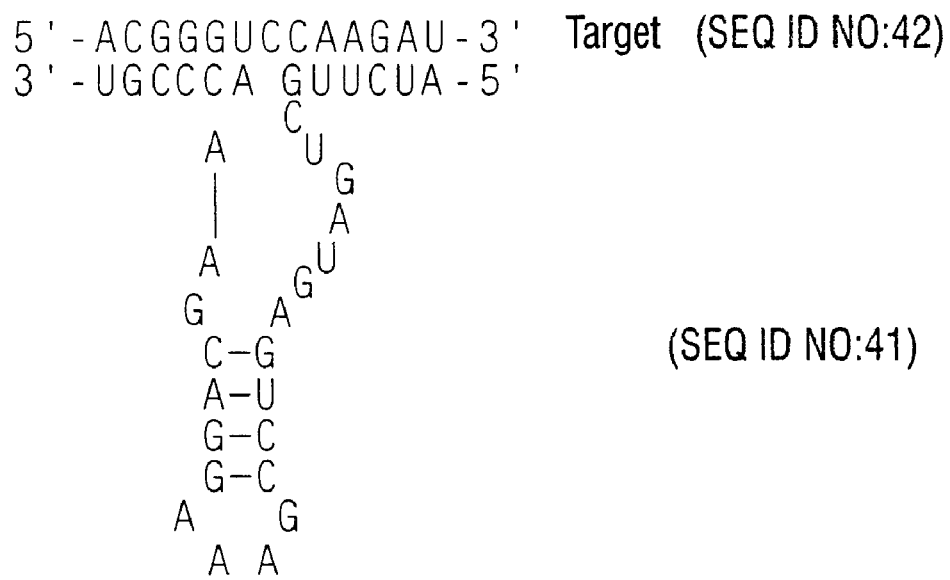

FIG. 23 shows the nucleotide sequence the nucleotide sequence (SEQ ID NO:41) and structure of an anti-IT15-4 hammerhead ribozyme, including RNA target sequence (SEQ ID NO:42).

Figure 24:
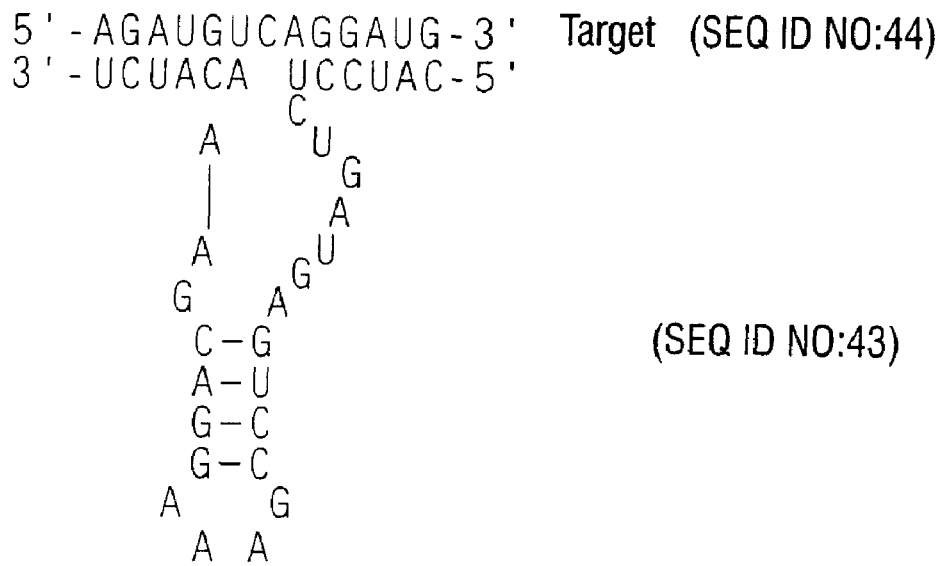

FIG. 24 shows the nucleotide sequence (SEQ ID NO:43) and structure of an anti-IT15-12Rz hammerhead ribozyme, including the RNA target sequence (SEQ ID NO:44).

Figure 25:
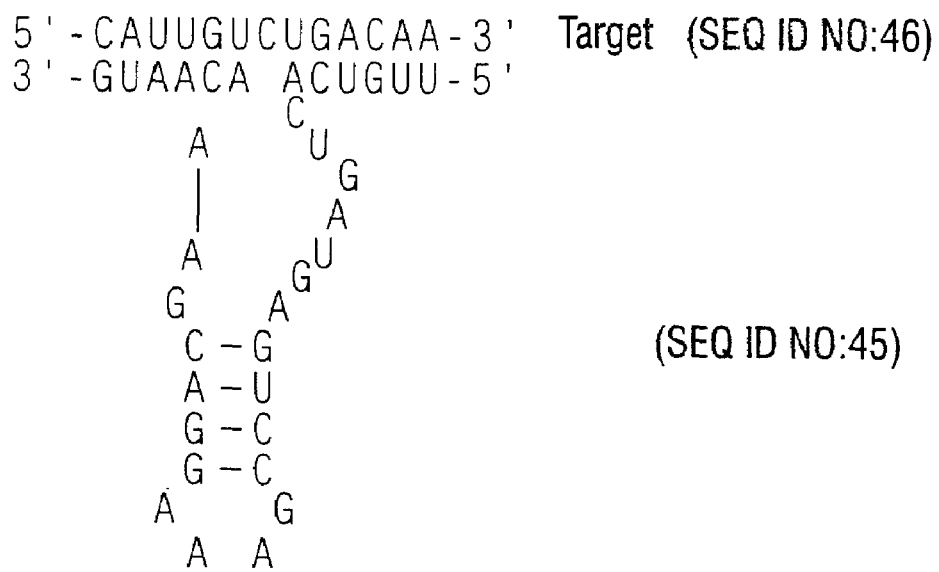

FIG. 25 shows shows the nucleotide sequence (SEQ ID NO:45) and structure of an anti-IT15-8Rz hammerhead ribozyme, including the RNA target sequence (SEQ ID NO:46).

FIG. 26 shows the nucleotide sequence (SEQ ID NO:47) and structure of a mouse anti-NADH dehydrogenase MWFE subunit nt 338 hammerhead ribozyme, including the RNA target sequence (SEQ ID NO:48).

FIG. 27 shows shows the nucleotide sequence (SEQ ID NO:49) and structure of a mouse anti-MnSOD nt 432 hammerhead ribozyme, including the RNA target sequence SEQ ID NO:50).

Figure 28:
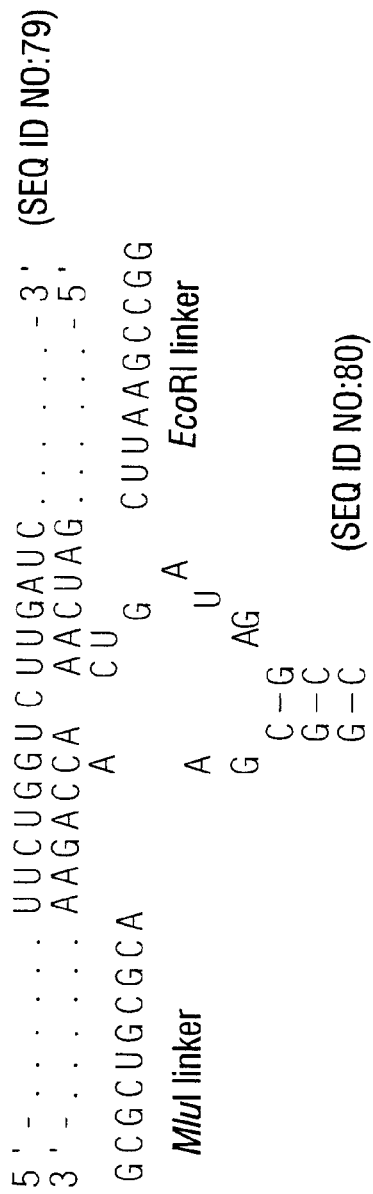

FIG. 28 shows the target strands of human rod ABCR at position 114 of the coding region. Shown is the nucleotide sequence (SEQ ID NO:81) of the ABCR ribozyme, and the RNA target sequence is shown as SEQ ID NO:80.

FIG. 29 shows the subunit sequence of the human rod photoreceptor ABC transporter (ABCR) cDNA (SEQ ID NO:65).

FIG. 30 shows the time course for the Rz114 oligo target.

Figure 31:
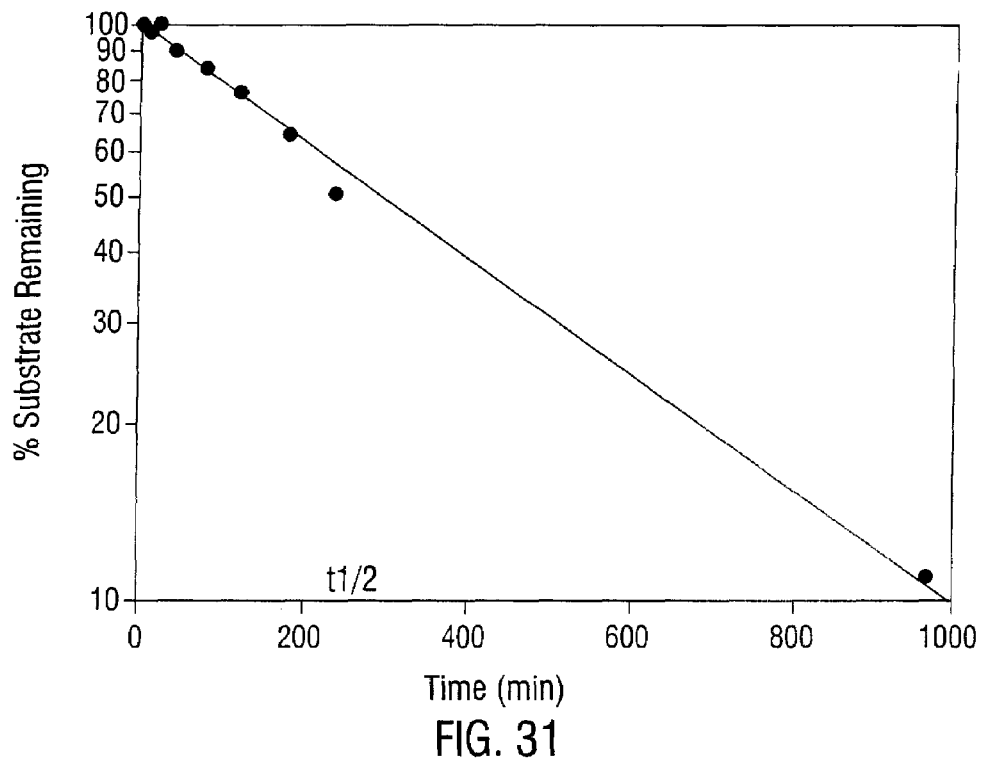
Figure 32:
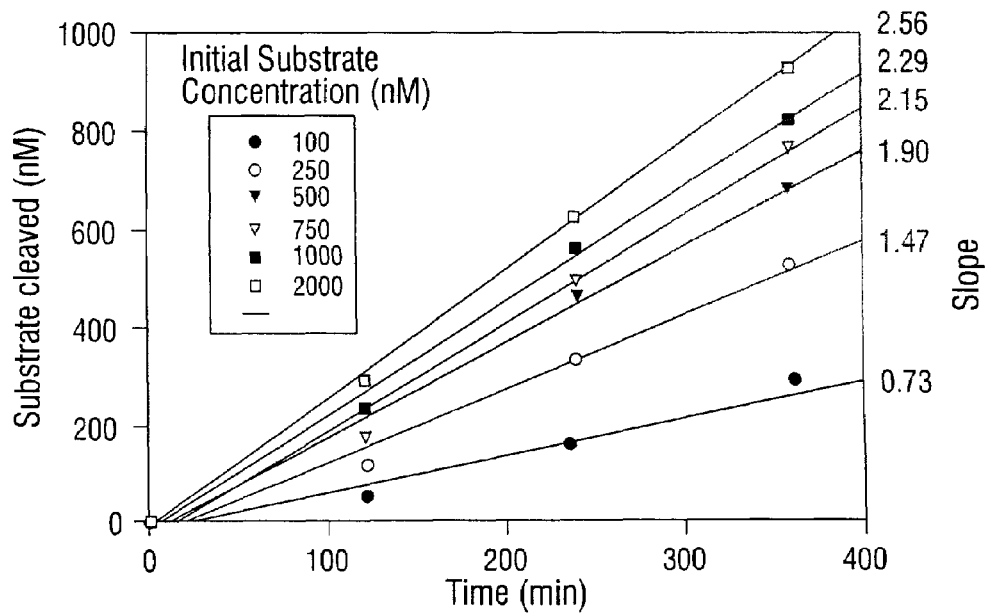

FIG. 31 shows the Rz oligo target time course as a semilogarithmic plot of the disappearance of substrate as a function of time demonstrating a $t_{1/2}$=240 min and single-exponential decay of half-lives. $K_{obs}$ is given by t½=0.693/$k_{obs}$. and $K_{obs}$=0.00289 min$^{-1}$ FIG. 32 shows a cleavage versus time plot of a substrate express experiment. The ribozyme concentration is 20 nM, and the substrate concentration varied from 100-2000 nM. The slopes of the lines are calculated by linear regression and shown on the right side of the figure.

Figure 33:

FIG. 33 shows a Rz114 substrate excess experiment.

Figure 34:
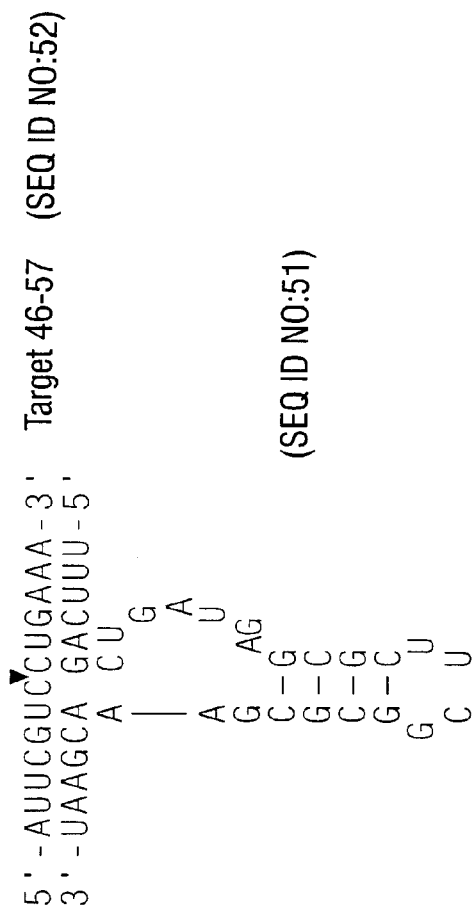

FIG. 34 shows the nucleotide sequence (SEQ ID NO:51) and structure of a mouse anti-D1-1-T7 Rz52 hammerhead ribozyme, including the RNA target sequence (SEQ ID NO:52).

Figure 35:
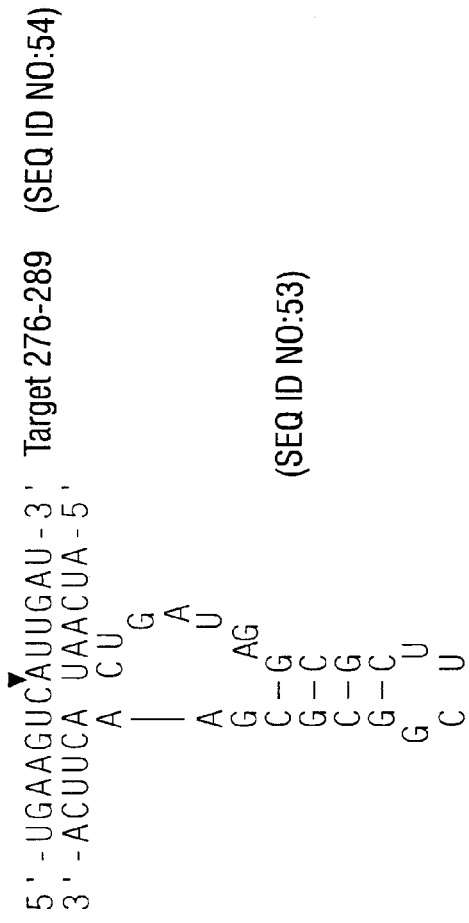

FIG. 35 shows the nucleotide sequence (SEQ ID NO:53) and structure of a mouse anti-D1-1-T7 Rz282 hammerhead ribozyme, including the RNA target sequence (SEQ ID NO:54).

Figure 36A:
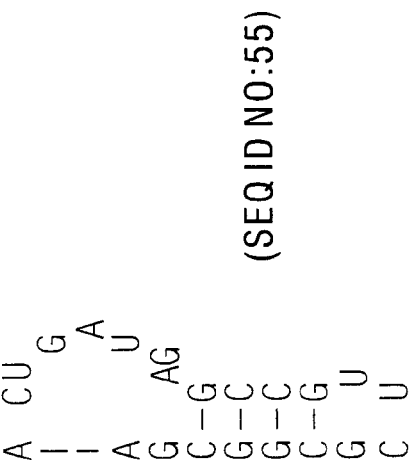

FIG. 36A shows the nucleotide sequence (SEQ ID NO:55) and structure of an anti-SOD-1 186 hammerhead ribozyme, including RNA target sequence (SEQ ID NO:56).

Figure 36B:
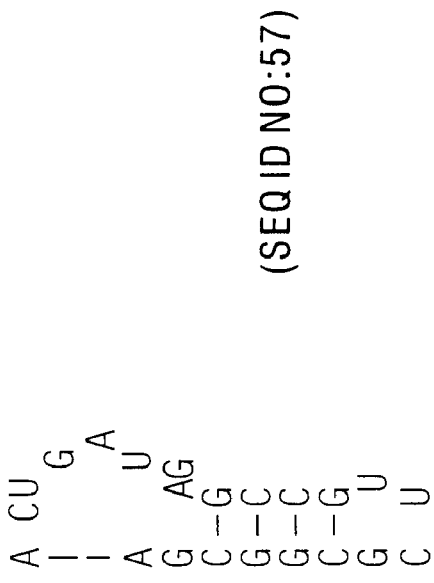

FIG. 36B shows the nucleotide sequence (SEQ ID NO:57) and structure of an anti-SOD-1 295 hammerhead ribozyme, including RNA target sequence (SEQ ID NO:58).

Figure 36C:
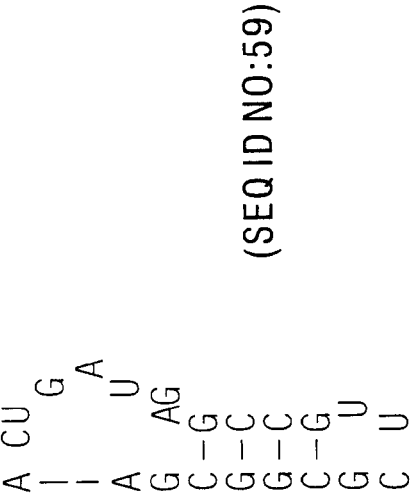

FIG. 36C shows the nucleotide sequence (SEQ ID NO:59) and structure of an anti-SOD-1 359 hammerhead ribozyme, including RNA target sequence (SEQ ID NO:60).

Figure 36D:
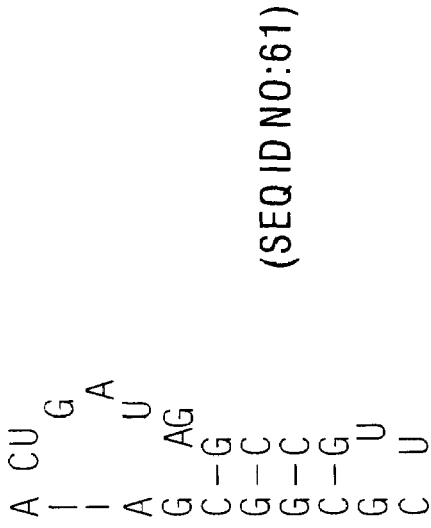

FIG. 36D shows the nucleotide sequence (SEQ ID NO:61) and structure of an anti-SOD-1 429 hammerhead ribozyme, including RNA target sequence (SEQ ID NO:62).

4.0 DESCRIPTION OF ILLUSTRATIVE EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The present invention provides methods for the identification of novel genes that are involved, either directly or indirectly, in a variety of cellular, biological and physiological processes, as well as methods for identifying the function of previously identified genes or gene fragments, such as expressed sequence tags (ESTs). The present invention provides methods to "knock-out" genes of unknown function in any somatic tissue and obtain evidence of the function of the genes based on the resulting "knock-out" phenotype. The invention also provides methods for testing genes of known or suspected function for their disease-causing potential, thereby identifying new disease-causing genes. The present invention also provides animal models of a variety of different physiological conditions, including certain inborn errors, and diseases.

The present methods involve the use of ribozymes, either designed to target a specific gene or gene fragment, or libraries of ribozymes that, through degeneracy in the bases involved in target recognition and binding, target random genes. Additionally, the invention provides methods of delivering or providing the ribozyme constructs to cells or animals using adeno-associated viral vectors and virus particles.

4.1 Adeno-Associated Virus Delivery of Ribozymes

For the vast amounts of data produced by the Human Genome Project to be useful, the function of identified genes must be deduced and their roles in human disease, if any, established. However, to date, only about 6,000 of the 50,000-100,000 human genes have been associated with a phenotype. Thus, documenting the full spectrum of disease-causing genes and creating animal models to understand pathogenic mechanisms and develop therapies are the next major challenges of human genetics. The present invention combines tools of virus-vectored gene therapy and promoter-regulated ribozymes to functionally identify such genes and create animal models of genetic disease. Ribozymes are RNA enzymes that have the potential to block the expression of specific genes. Adeno-associated virus (AAV) has been successfully used to deliver ribozymes as therapy in animal models of dominant genetic disease. The present invention extends the approach to create disease in experimental animals, and therefore to establish animal models for disease. The AAV-ribozyme approach permits the generation of somatic gene knockouts, avoiding the problem of embryonic lethality and the limitation to small animals typical of current gene-disruption strategies.

Over 100 genetic loci have been linked to retinal disease in man. Of these, some are well documented to be associated genes for retinal proteins, but most are simply intervals on the human genetic map. In addition, the genetic etiology of some major retinal diseases, including age-related macular degeneration, is obscure. Age related macular degeneration affects one in three individuals over the age of 70. Differential-display and expressed sequence tag libraries are available that contain clones of genes expressed highly in specific retinal cells, including photoreceptor cells and the retinal pigment epithelium. To identify which among these highly expressed genes may be required for retinal function, hammerhead and hairpin ribozymes have been designed to cleave the messenger RNA molecules that they encode. These are then delivered to experimental animals using AAV to determine which lead to retinal degeneration.

Mutations in two major genetic pathways, characterized by the P53 and by the Rb genes respectively, have been demonstrated to lead to unregulated cell division associated with cancer. Other genes associated with, and perhaps independent of these pathways, may also be involved in controlling the replication and spread of tumor cells. A library of ribozymes containing partially randomized targeting domains have been delivered to specific tissues in order to create animals prone to tumors due to deficits in the expression of previously unidentified tumor suppressor genes. Sequence tags based on these ribozymes are then used to identify and clone potential tumor suppressor genes.

4.2 Ribozymes

Although proteins traditionally have been used for catalysis of nucleic acids, another class of macromolecules has emerged as useful in this endeavor. Ribozymes are RNA-protein complexes that cleave nucleic acids in a site-specific fashion. Ribozymes have specific catalytic domains that possess endonuclease activity (Kim and Cech, 1987; Gerlach et al., 1987; Forster and Symons, 1987). For example, a large number of ribozymes accelerate phosphoester transfer reactions with a high degree of specificity, often cleaving only one of several phosphoesters in an oligonucleotide substrate (Cech et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce, 1989; Cech et al., 1981). For example, U.S. Pat. No. 5,354,855 (specifically incorporated herein by reference) reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., 1991; Sarver et al., 1990). Recently, it was reported that ribozymes elicited genetic changes in some cells lines to which they were applied; the altered genes included the oncogenes H-ras, c-fos and genes of HIV. Most of this work involved the modification of a target mRNA, based on a specific mutant codon that is cleaved by a specific ribozyme.

Six basic varieties of naturally occurring enzymatic RNAs are known presently. Each can catalyze the hydrolysis of RNA phosphodiester bonds in trans (and thus can cleave other RNA molecules) under physiological conditions. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nature of a ribozyme is advantageous over many technologies, such as antisense technology (where a nucleic acid molecule simply binds to a nucleic acid target to block its translation) since the concentration of ribozyme necessary to affect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base pairing mechanism of binding to the target RNA, but also on the mechanism of target RNA cleavage. Single mismatches, or base-substitutions, near the site of cleavage can completely eliminate catalytic activity of a ribozyme. Similar mismatches in antisense molecules do not prevent their action (Woolf et al., 1992). Thus, the specificity of action of a ribozyme is greater than that of an antisense oligonucleotide binding the same RNA site.

The enzymatic nucleic acid molecule may be formed in a hammerhead, hairpin, a hepatitis δ virus, group I intron or RNaseP RNA (in association with an RNA guide sequence) or Neurospora VS RNA motif. Examples of hammerhead motifs are described by Rossi et al. (1992). Examples of hairpin motifs are described by Hampel et al. (Eur. Pat. Appl. Publ. No. EP 0360257), Hampel and Tritz (1989), Hampel et al. (1990) and U.S. Pat. No. 5,631,359 (specifically incorporated herein by reference). An example of the hepatitis δ virus motif is described by Perrotta and Been (1992); an example of the RNaseP motif is described by Guerrier-Takada et al. (1983); Neurospora VS RNA ribozyme motif is described by Collins (Saville and Collins, 1990; Saville and Collins, 1991; Collins and Olive, 1993); and an example of the Group I intron is described in U.S. Pat. No. 4,987,071 (specifically incorporated herein by reference). All that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule. Thus the ribozyme constructs need not be limited to specific motifs mentioned herein.

In certain embodiments, it may be important to produce enzymatic cleaving agents that exhibit a high degree of specificity for the RNA of a desired target, such as one of the sequences disclosed herein. The enzymatic nucleic acid molecule is preferably targeted to a highly conserved sequence region of a target mRNA. Such enzymatic nucleic acid molecules can be delivered exogenously to specific cells as required, although in preferred embodiments the ribozymes are expressed from DNA or RNA vectors that are delivered to specific cells.

Small enzymatic nucleic acid motifs (e.g., of the hammerhead or the hairpin structure) may also be used for exogenous delivery. The simple structure of these molecules increases the ability of the enzymatic nucleic acid to invade targeted regions of the mRNA structure. Alternatively, catalytic RNA molecules can be expressed within cells from eukaryotic promoters (e.g., Scanlon et al., 1991; Kashani-Sabet et al., 1992; Dropulic et al., 1992; Weerasinghe et al., 1991; Ojwang et al., 1992; Chen et al., 1992; Sarver et al., 1990). Those skilled in the art realize that any ribozyme can be expressed in eukaryotic cells from the appropriate DNA vector. The activity of such ribozymes can be augmented by their release from the primary transcript by a second ribozyme (Int. Pat. Appl. Publ. No. WO 93/23569, and Int. Pat. Appl. Publ. No. WO 94/02595, both hereby incorporated by reference; Ohkawa et al., 1992; Taira et al., 1991; and Ventura et al., 1993).

Ribozymes may be added directly, or can be complexed with cationic lipids, lipid complexes, packaged within liposomes, or otherwise delivered to target cells. The RNA or RNA complexes can be locally administered to relevant tissues ex vivo, or in vivo through injection, aerosol inhalation, infusion pump or stent, with or without their incorporation in biopolymers.

Ribozymes may be designed as described in int. Pat. Appl. Publ. No. WO 93/23569 and Int. Pat. Appl. Publ. No. WO 94/02595 (each specifically incorporated herein by reference) and synthesized to be tested in vitro and in vivo, as described. Such ribozymes can also be optimized for delivery. While specific examples are provided, those in the art will recognize that equivalent RNA targets in other species can be utilized when necessary.

Hammerhead or hairpin ribozymes may be individually analyzed by computer folding (Jaeger et al., 1989) to assess whether the ribozyme sequences fold into the appropriate secondary structure, as described herein. Those ribozymes with unfavorable intramolecular interactions between the binding arms and the catalytic core are eliminated from consideration. Varying binding arm lengths can be chosen to optimize activity. Generally, at least 5 or so bases on each arm are able to bind to, or otherwise interact with, the target RNA.

Ribozymes of the hammerhead or hairpin motif may be designed to anneal to various sites in the mRNA message, and can be chemically synthesized. The method of synthesis used follows the procedure for normal RNA synthesis as described in Usman et al. (1987) and in Scaringe et al. (1990) and makes use of common nucleic acid protecting and coupling groups, such as dimethoxytrityl at the 5'-end, and phosphoramidites at the 3'-end. Average stepwise coupling yields are typically >98%. Hairpin ribozymes may be synthesized in two parts and annealed to reconstruct an active ribozyme (Chowrira and Burke, 1992). Ribozymes may be modified extensively to enhance stability by modification with nuclease resistant groups, for example, 2'-amino, 2'-C-allyl, 2'-flouro, 2'-o-methyl, 2'-H (for a review see e.g., Usman and Cedergren, 1992). Ribozymes may be purified by gel electrophoresis using general methods or by high-pressure liquid chromatography and resuspended in water.

Ribozyme activity can be optimized by altering the length of the ribozyme binding arms, or chemically synthesizing ribozymes with modifications that prevent their degradation by serum ribonucleases (see e.g., Int. Pat. Appl. Publ. No.

WO 92/07065; Perrault et al, 1990; Pieken et al., 1991; Usman and Cedergren, 1992; Int. Pat. Appl. Publ. No. WO 93/15187; Int. Pat. Appl. Publ. No. WO 91/03162; Eur. Pat. Appl. Publ. No. 92110298.4; U.S. Pat. No. 5,334,711; and Int. Pat. Appl. Publ. No. WO 94/13688, which describe various chemical modifications that can be made to the sugar moieties of enzymatic RNA molecules), modifications which enhance their efficacy in cells, and removal of stem II bases to shorten RNA synthesis times and reduce chemical requirements.

A preferred means of accumulating high concentrations of a ribozyme(s) within cells is to incorporate the ribozyme-encoding sequences into a DNA expression vector. Transcription of the ribozyme sequences are driven from a promoter for eukaryotic RNA polymerase I (pol I), RNA polymerase II (pol II), or RNA polymerase III (pol III). Transcripts from pol II or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters may also be used, providing that the prokaryotic RNA polymerase enzyme is expressed in the appropriate cells (Elroy-Stein and Moss, 1990; Gao and Huang, 1993; Lieber et al., 1993; Zhou et al, 1990). Ribozymes expressed from such promoters can function in mammalian cells (Kashani-Sabet et al, 1992; Ojwang et al, 1992; Chen et at, 1992; Yu et al., 1993; L'Huillier et al., 1992; Lisziewicz et al, 1993). Although incorporation of the present ribozyme constructs into adeno-associated viral vectors is preferred, such transcription units can be incorporated into a variety of vectors for introduction into mammalian cells, including but not restricted to, plasmid DNA vectors, other viral DNA vectors (such as adenovirus vectors), or viral RNA vectors (such as retroviral, semliki forest virus, sindbis virus vectors).

Sullivan et al. (Int. Pat. Appl. Publ. No. WO 94/02595) describes general methods for delivery of enzymatic RNA molecules. Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, ribozymes may be directly delivered ex vivo to cells or tissues with or without the aforementioned vehicles. Alternatively, the RNA/vehicle combination may be locally delivered by direct inhalation, by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of ribozyme delivery and administration are provided in Int. Pat. Appl. Publ. No. WO 94/02595 and Int. Pat. Appl. Publ. No. WO 93/23569, each specifically incorporated herein by reference.

Ribozymes of this invention may be used to inhibit gene expression and define the role (essentially) of specified gene products in the progression of disease. In this manner, other genetic targets may be defined as important mediators of the disease. These studies lead to better treatment of the disease progression by affording the possibility of combination therapies (e.g., multiple ribozymes targeted to different genes, ribozymes coupled with known small molecule inhibitors, or intermittent treatment with combinations of ribozymes and/or other chemical or biological molecules).

4.3 Promoters and Enhancers

Recombinant vectors form important aspects of the present invention. The term "expression vector or construct" means any type of genetic construct containing a nucleic acid in which part or all of the nucleic acid encoding sequence is capable of being transcribed. In preferred embodiments, expression only includes transcription of the nucleic acid, for example, to generate ribozyme constructs.

Particularly useful vectors are contemplated to be those vectors in which the nucleic acid segment to be transcribed is positioned under the transcriptional control of a promoter. A "promoter" refers to a DNA sequence recognized by the synthetic machinery of the cell, or introduced synthetic machinery, required to initiate the specific transcription of a gene. The phrases "operatively positioned," "under control" or "under transcriptional control" means that the promoter is in the correct location and orientation in relation to the nucleic acid to control RNA polymerase initiation and expression of the gene.

In preferred embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a ribozyme construct in its natural environment. Such promoters may include promoters normally associated with other genes, and/or promoters isolated from any other bacterial, viral, eukaryotic, or mammalian cell.

Naturally, it will be important to employ a promoter that effectively directs the expression of the DNA segment in the cell type, organism, or even animal, chosen for expression. The use of promoter and cell type combinations for protein expression is generally known to those of skill in the art of molecular biology; for example, see Sambrook et al. (1989), incorporated herein by reference. The promoters employed may be constitutive, or inducible, and can be used under the appropriate conditions to direct high-level expression of the introduced DNA segment.

At least one module in a promoter functions to position the start site for RNA synthesis. The best-known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter that is employed to control the expression of a nucleic acid is not believed to be critical, so long as it is capable of expressing the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter, such as a CMV or an HSV promoter. In certain aspects of the invention, tetracycline controlled promoters are contemplated.

In various other embodiments, the human cytomegalovirus (CMV) immediate early gene promoter, the SV40 early promoter and the Rous sarcoma virus long terminal repeat can be used to obtain high-level expression of transgenes. The use of other viral or mammalian cellular or bacterial phage promoters that are well known in the art to achieve expression of a transgene is contemplated as well, provided that the levels of expression are sufficient for a given purpose. Tables 1 and 2 below list several elements/promoters that may be employed, in the context of the present invention, to regulate the expression of the present ribozyme constructs. This list is not intended to be exhaustive of all the possible elements involved in the promotion of transgene expression but, merely, to be exemplary thereof.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Additionally any promoter/enhancer combination (as per the Eukaryotic Promoter Data Base EPDB) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

TABLE 1

PROMOTER AND ENHANCER ELEMENTS

| Promoter/Enhancer | References |
|---|---|
| Immunoglobulin Heavy Chain | Banerji et al., 1983; Gilles et al., 1983; Grosschedl and Baltimore, 1985; Atchinson and Perry, 1986, 1987; Imler et al., 1987; Weinberger et al., 1984; Kiledjian et al., 1988; Porton et al., 1990 |
| Immunoglobulin Light Chain | Queen and Baltimore, 1983; Picard and Schaffner, 1984 |
| T-Cell Receptor | Luria et al., 1987; Winoto and Baltimore, 1989; Redondo et al., 1990 |
| HLA DQ a and DQ β | Sullivan and Peterlin, 1987 |
| β-Interferon | Goodbourn et al., 1986; Fujita et al., 1987; Goodbourn and Maniatis, 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRa | Sherman et al., 1989 |
| β-Actin | Kawamoto et al., 1988; Ng et al.; 1989 |
| Muscle Creatine Kinase | Jaynes et al., 1988; Horlick and Benfield, 1989; Johnson et al., 1989 |
| Prealbumin (Transthyretin) | Costa et al., 1988 |
| Elastase I | Ornitz et al., 1987 |
| Metallothionein | Karin et al., 1987; Culotta and Hamer, 1989 |
| Collagenase | Pinkert et al., 1987; Angel et al., 1987 |
| Albumin Gene | Pinkert et al., 1987; Tronche et al., 1989, 1990 |
| α-Fetoprotein | Godbout et al., 1988; Campere and Tilghman, 1989 |
| t-Globin | Bodine and Ley, 1987; Perez-Stable and Constantini, 1990 |
| β-Globin | Trudel and Constantini, 1987 |
| e-fos | Cohen et al., 1987 |
| c-HA-ras | Treisman, 1986; Deschamps et al., 1985 |
| Insulin | Edlund et al., 1985 |
| Neural Cell Adhesion Molecule (NCAM) | Hirsh et al., 1990 |
| $\alpha_{1\text{-Antitrypain}}$ | Latimer et al., 1990 |
| H2B (TH2B) Histone | Hwang et al., 1990 |
| Mouse or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor | Pech et al., 1989 |
| Duchenne Muscular Dystrophy | Klamut et al., 1990 |
| SV40 | Banerji et al., 1981; Moreau et al., 1981; Sleigh and Lockett, 1985; Firak and Subramanian, 1986; Herr and Clarke, 1986; Imbra and Karin, 1986; Kadesch and Berg, 1986; Wang and Calame, 1986; Ondek et al., 1987; Kuhl et al., 1987; Schaffner et al., 1988 |

TABLE 1-continued

PROMOTER AND ENHANCER ELEMENTS

| Promoter/Enhancer | References |
| --- | --- |
| Polyoma | Swartzendruber and Lehman, 1975; Vasseur et al., 1980; Katinka et al., 1980, 1981; Tyndall et al., 1981; Dandolo et al., 1983; de Villiers et al., 1984; Hen et al., 1986; Satake et al., 1988; Campbell and Villarreal, 1988 |
| Retroviruses | Kriegler and Botchan, 1982, 1983; Levinson et al., 1982; Kriegler et al., 1983, 1984a, b, 1988; Bosze et al., 1986; Miksicek et al., 1986; Celander and Haseltine, 1987; Thiesen et al., 1988; Celander et al., 1988; Choi et al., 1988; Reisman and Rotter, 1989 |
| Papilloma Virus | Campo et al., 1983; Lusky et al., 1983; Spandidos and Wilkie, 1983; Spalholz et al., 1985; Lusky and Botchan, 1986; Cripe et al., 1987; Gloss et al., 1987; Hirochika et al., 1987; Stephens and Hentschel, 1987; Glue et al., 1988 |
| Hepatitis B Virus | Bulla and Siddiqui, 1986; Jameel and Siddiqui, 1986; Shaul and Ben-Levy, 1987; Spandau and Lee, 1988; Vannice and Levinson, 1988 |
| Human Immunodeficiency Virus | Muesing et al., 1987; Hauber and Cullan, 1988; Jakobovits et al., 1988; Feng and Holland, 1988; Takebe et al., 1988; Rosen et al., 1988; Berkhout et al., 1989; Laspia et al., 1989; Sharp and Marciniak, 1989; Braddock et al., 1989 |
| Cytomegalovirus | Weber et al., 1984; Boshart et al., 1985; Foecking and Hofstetter, 1986 |
| Gibbon Ape Leukemia Virus | Holbrook et al., 1987; Quinn et al., 1989 |

TABLE 2

INDUCIBLE ELEMENTS

| Element | Inducer | References |
| --- | --- | --- |
| MT II | Phorbol Ester (TFA) Heavy metals | Palmiter et al., 1982; Haslinger and Karin, 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors and Varmus, 1983; Chandler et al., 1983; Lee et al., 1984; Ponta et al., 1985; Sakai et al., 1988 |
| β-Interferon | poly(rI)x poly(rc) | Tavernier et al., 1983 |
| Adenovirus 5 E2 | Ela | Imperiale and Nevins, 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | Ela, SV40 Large T Antigen | Taylor et al., 1989; Taylor and Kingston, 1990a, b |
| Proliferin | Phorbol Ester-TPA | Mordacq and Linzer, 1989 |
| Tumor Necrosis Factor | FMA | Hensel et al., 1989 |
| Thyroid Stimulating Hormone a Gene | Thyroid Hormone | Chatterjee et al., 1989 |

As used herein, the terms "engineered" and "recombinant" cells are intended to refer to a cell into which an exogenous DNA segment, such as DNA segment that leads to the transcription of a ribozyme, has been introduced. Therefore, engineered cells are distinguishable from naturally occurring cells, which do not contain a recombinantly introduced exogenous DNA segment. Engineered cells are thus cells having DNA segment introduced through the hand of man.

To express a ribozyme in accordance with the present invention one would prepare an expression vector that comprises a ribozyme-encoding nucleic acid under the control of one or more promoters. To bring a sequence "under the control of" a promoter, one positions the 5' end of the transcription initiation site of the transcriptional reading frame generally between about 1 and about 50 nucleotides "downstream" of (i.e., 3' of) the chosen promoter. The "upstream" promoter stimulates transcription of the DNA and promotes expression of the encoded ribozyme. This is the meaning of "recombinant expression" in this context.

4.4 Adeno-Associated Virus (AAV)

Adeno-associated virus (AAV) is particularly attractive for gene transfer because it does not induce any pathogenic response and can integrate into the host cellular chromosome (Kotin et al., 1990). The AAV terminal repeats (TRs) are the only essential cis-components for the chromosomal integration (Muzyczka and McLaughlin, 1988). These TRs are reported to have promoter activity (Flotte et al., 1993). They may promote efficient gene transfer from the cytoplasm to the nucleus or increase the stability of plasmid DNA and enable longer-lasting gene expression (Bartlett et al., 1996). Studies using recombinant plasmid DNAs containing AAV TRs have attracted considerable interest. AAV-based plasmids have been shown to drive higher and longer transgene expression than the identical plasmids lacking the TRs of AAV in most cell types (Philip et al., 1994; Shafron et al., 1998; Wang et al., 1999).

AAV (Ridgeway, 1988; Hermonat and Muzyczka, 1984) is a parvovirus, discovered as a contamination of adenoviral stocks. It is a ubiquitous virus (antibodies are present in 85% of the US human population) that has not been linked to any disease. It is also classified as a dependovirus, because its replication is dependent on the presence of a helper virus, such as adenovirus. Five serotypes have been isolated, of which AAV-2 is the best characterized. AAV has a single-stranded linear DNA that is encapsidated into capsid proteins VP1, VP2 and VP3 to form an icosahedral virion of 20 to 24 nm in diameter (Muzyczka and McLaughlin, 1988).

The AAV DNA is approximately 4.7 kilobases long. It contains two open reading frames and is flanked by two ITRs. There are two major genes in the AAV genome: rep and cap. The rep gene encodes a protein responsible for viral replications, whereas the cap gene encodes the capsid protein VP1-3. Each ITR forms a T-shaped hairpin structure. These terminal repeats are the only essential cis components of the AAV for chromosomal integration. Therefore, the AAV can be used as a vector with all viral coding sequences removed and replaced by the cassette of genes for delivery. Three viral promoters have been identified and named p5, p19, and p40, according to their map position. Transcription from p5 and p19 results in production of rep proteins, and transcription from p40 produces the capsid proteins (Hermonat and Muzyczka, 1984).

There are several factors that prompted researchers to study the possibility of using rAAV as an expression vector. One is that the requirements for delivering a gene to integrate into the host chromosome are surprisingly few. It is necessary to have the 145-bp ITRs, which are only 6% of the AAV genome. This leaves room in the vector to assemble a 4.5-kb DNA insertion. While this carrying capacity may prevent the AAV from delivering large genes, it is amply suited for delivering the antisense constructs of the present invention.

AAV is also a good choice of delivery vehicles due to its safety. There is a relatively complicated rescue mechanism: not only wild type adenovirus but also AAV genes are required to mobilize rAAV. Likewise, AAV is not pathogenic and not associated with any disease. The removal of viral coding sequences minimizes immune reactions to viral gene expression, and therefore, rAAV does not evoke an inflammatory response. AAV therefore, represents an ideal candidate for delivery of the present hammerhead ribozyme constructs.

4.5 Pharmaceutical Compositions and Kits

Pharmaceutical compositions of the present invention will generally comprise an effective amount of at least a first ribozyme or ribozyme library, incorporated into an adeno-associated viral vector, or adeno-associated viral particles containing at least a first ribozyme or ribozyme library, dissolved or dispersed in a pharmaceutically acceptable carrier or aqueous medium.

The phrases "pharmaceutically or pharmacologically acceptable" refer to molecular entities and compositions that do not produce an adverse, allergic or other untoward reaction when administered to an animal, or a human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

4.5.1 Parenteral Formulations

The agents of the present invention will often be formulated for parenteral administration, e.g., formulated for injection via the intravenous, intramuscular, sub-cutaneous or other such routes. The preparation of an aqueous composition that contains one or more agents, such as a ribozyme, ribozyme library or adeno-associated virus containing a ribozyme or ribozyme library, will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

Solutions of the active compounds as freebase or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Compositions comprising the agents of the present invention can be formulated into a composition in a neutral or salt form. Pharmaceutically acceptable salts include the acid addition salts and those formed with inorganic acids such as, for example, hydrochloric or phosphoric acids, or such organic acids as acetic, oxalic, tartaric, mandelic, and the like. Salts can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), dimethylsulfoxide (DMSO), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and freeze-drying techniques, which yield a powder of the active ingredient, plus any additional desired ingredient from a previously sterile-filtered solution thereof.

Upon formulation, solutions will be administered in a manner compatible with the dosage formulation and in such amount as is biologically or therapeutically effective. Formulations are easily administered in a variety of dosage forms, such as the type of injectable solutions described above, but drug release capsules and the like can also be employed.

Suitable pharmaceutical compositions in accordance with the invention will generally include an amount of one or more of the agents of the present invention admixed with an acceptable pharmaceutical diluent or excipient, such as a sterile aqueous solution, to give a range of final concentrations, depending on the intended use. The techniques of preparation is generally well known in the art as exemplified by Remington's Pharmaceutical Sciences, 16th Ed. Mack Publishing Company, 1980, incorporated herein by reference. It should be appreciated that endotoxin contamination should be kept minimally at a safe level, for example, less that 0.5 ng/mg protein. Moreover, for human administration, preparations should meet sterility, pyrogenicity, general safety and purity standards as required by FDA Office of Biological Standards.

In addition to the compounds formulated for parenteral administration, such as intravenous or intramuscular injection, other pharmaceutically acceptable forms are also contemplated, e.g., tablets or other solids for oral administration, time release capsules, liposomal forms and the like. Other pharmaceutical formulations may also be used, dependent on the condition to be treated. Of course, methods for the determination of optimal dosages for conditions such as these would be evident to those of skill in the art in light of the instant specification, and the knowledge of the skilled artisan.

It is contemplated that certain benefits will result from the manipulation of the agents of the present invention to provide them with a longer in vivo half-life. Slow release formulations are generally designed to give a constant drug level over an extended period. Increasing the half-life of a drug, such as agents of the present invention, is intended to result in high intracellular levels upon administration, which levels are maintained for a longer time, but which levels generally decay depending on the pharmacokinetics of the construct.

4.5.2 Therapeutic Kits

The present invention also provides therapeutic kits comprising the agents of the present invention described herein. Such kits will generally contain, in suitable container, a pharmaceutically acceptable formulation of at least a first ribozyme, ribozyme library or adeno-associated virus particles comprising at least a first ribozyme or ribozyme library, in accordance with the invention. The kits may also contain other pharmaceutically acceptable formulations.

The kits may have a single container that contains the agent, with or without any additional components, or they may have distinct container means for each desired agent. In such kits, the components may be pre-complexed, either in a molar equivalent combination, or with one component in excess of the other; or each of the components of the kit may be maintained separately within distinct containers prior to administration to a patient.

When the components of the kit are provided in one or more liquid solutions, the liquid solution is an aqueous solution, with a sterile aqueous solution being particularly preferred. However, the components of the kit may be provided as dried powder(s). When reagents or components are provided as a dry powder, the powder can be reconstituted by the addition of a suitable solvent. It is envisioned that the solvent may also be provided in another container means. One of the components of the kit may be provided in capsules for oral administration.

The container means of the kit will generally include at least one vial, test tube, flask, bottle, syringe or other container means, into which a ribozyme, ribozyme library or adeno-associated viral particles comprising a ribozyme or ribozyme library, and any other desired agent, may be placed and, preferably, suitably aliquoted. Where additional components are included, the kit will also generally contain a second vial or other container into which these are placed, enabling the administration of separated designed doses. The kits may also comprise a second/third container means for containing a sterile, pharmaceutically acceptable buffer or other diluent.

The kits may also contain a means by which to administer the ribozyme, ribozyme library or adeno-associated viral particles comprising a ribozyme or ribozyme library to an animal or patient, e.g., one or more needles or syringes, or even an eye dropper, pipette, or other such like apparatus, from which the formulation may be injected into the animal or applied to a diseased area of the body. The kits of the present invention will also typically include a means for containing the vials, or such like, and other component, in close confinement for commercial sale, such as, e.g., injection or blow-molded plastic containers into which the desired vials and other apparatus are placed and retained.

4.6 Mutagenesis

Site-specific mutagenesis is a technique useful in the preparation and testing of sequence variants by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art. As will be appreciated, the technique typically employs a bacteriophage vector that exists in both a single stranded and double stranded form. Typical vectors useful in site-directed mutagenesis include vectors such as the M13 phage. These phage vectors are commercially available and their use is generally well known to those skilled in the art. Double stranded plasmids are also routinely employed in site directed mutagenesis, which eliminates the step of transferring the gene of interest from a phage to a plasmid.

In general, site-directed mutagenesis is performed by first obtaining a single-stranded vector, or melting of two strands of a double stranded vector that includes within its sequence a DNA sequence encoding the desired ribozyme or other nucleic acid construct. An oligonucleotide primer bearing the desired mutated sequence is synthetically prepared. This primer is then annealed with the single-stranded DNA preparation, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected that include recombinant vectors bearing the mutated sequence arrangement.

The preparation of sequence variants of the selected ribozyme using site-directed mutagenesis is provided as a means of producing potentially useful species and is not meant to be limiting, as there are other ways in which sequence variants may be obtained. For example, recombinant vectors encoding the desired gene may be treated with mutagenic agents, such as hydroxylamine, to obtain sequence variants.

4.7 Nucleic Acid Amplification

Nucleic acid, used as a template for amplification, may be isolated from cells contained in the biological sample according to standard methodologies (Sambrook et al., 1989). The nucleic acid may be genomic DNA or fractionated or whole cell RNA. Where RNA is used, it may be desired to convert the RNA to a complementary DNA. In one embodiment, the RNA is whole cell RNA and is used directly as the template for amplification.

Pairs of primers that selectively hybridize to nucleic acids corresponding to the ribozymes or conserved flanking regions are contacted with the isolated nucleic acid under conditions that permit selective hybridization. The term "primer", as defined herein, is meant to encompass any nucleic acid that is capable of priming the synthesis of a nascent nucleic acid in a template-dependent process. Typically, primers are oligonucleotides from ten to twenty base pairs in length, but longer sequences can be employed. Primers may be provided in double-stranded or single-stranded form, although the single-stranded form is preferred.

Once hybridized, the nucleic acid:primer complex is contacted with one or more enzymes that facilitate template-dependent nucleic acid synthesis. Multiple rounds of amplification, also referred to as "cycles," are conducted until a sufficient amount of amplification product is produced.

Next, the amplification product is detected. In certain applications, the detection may be performed by visual means. Alternatively, the detection may involve indirect identification of the product via chemiluminescence, radioactive scintigraphy of incorporated radiolabel or fluorescent label or even via a system using electrical or thermal impulse signals (Affymax technology).

A number of template dependent processes are available to amplify the marker sequences present in a given template sample. One of the best-known amplification methods is the polymerase chain reaction (referred to as PCR™), which is described in detail in U.S. Pat. Nos. 4,683,195, 4,683,202 and 4,800,159 (each of which is incorporated herein by reference in its entirety).

Briefly, in PCR™, two primer sequences are prepared that are complementary to regions on opposite complementary strands of the marker sequence. An excess of deoxynucleoside triphosphates is added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated.

A reverse transcriptase PCR™ amplification procedure may be performed in order to quantify the amount of mRNA amplified. Methods of reverse transcribing RNA into cDNA are well known and described in Sambrook et al. (1989). Alternative methods for reverse transcription utilize thermostable, RNA-dependent DNA polymerases. These methods are described in Int. Pat. Appl. Publ. No. WO 90/07641 (specifically incorporated herein by reference). Polymerase chain reaction methodologies are well known in the art.

Another method for amplification is the ligase chain reaction ("LCR"), disclosed in EPA No. 320 308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750 describes a method similar to LCR for binding probe pairs to a target sequence.

Qβ Replicase (QβR), described in Int. Pat. Appl. No. PCT/US87/00880, incorporated herein by reference, may also be used as still another amplification method in the present invention. In this method, a replicative sequence of RNA that has a region complementary to that of a target is added to a sample in the presence of an RNA polymerase. The polymerase will copy the replicative sequence that can then be detected.

An isothermal amplification method, in which restriction endonucleases and ligases are used to achieve the amplification of target molecules that contain nucleotide 5'-[α-thio]-triphosphates in one strand of a restriction site may also be useful in the amplification of nucleic acids in the present invention.

Strand Displacement Amplification (SDA), described in U.S. Pat. Nos. 5,455,166, 5,648,211, 5,712,124 and 5,744, 311, each incorporated herein by reference, is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA. Target specific sequences can also be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products that are released after digestion. The original template is annealed to another cycling probe and the reaction is repeated.

Still another amplification methods described in GB Application No. 2 202 328, and in Int. Pat. Appl. No. PCT/US89/01025, each of which is incorporated herein by reference in its entirety, may be used in accordance with the present invention. In the former application, "modified" primers are used in a PCR™-like, template- and enzyme-dependent synthesis. The primers may be modified by labeling with a capture moiety (e.g., biotin) and/or a detector moiety (e.g., enzyme). In the latter application, an excess of labeled probes is added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS), including nucleic acid sequence based amplification (NASBA) and 3SR Gingeras et al., Int. Pat. Appl. Publ. No. WO 88/10315, incorporated herein by reference. In NASBA, the denaturation of a clinical sample, treatment with lysis buffer and minispin columns for isolation of DNA and RNA or guanidinium chloride extraction of RNA. These amplification techniques involve annealing a primer that has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by an RNA polymerase such as T7 or SP6. In an isothermal cyclic reaction, the RNA's are reverse transcribed into single stranded DNA, which is then converted to double stranded DNA, and then transcribed once again with an RNA polymerase such as T7 or SP6. The resulting products, whether truncated or complete, indicate target specific sequences.

Davey et al, EPA No. 329 822 (incorporated herein by reference in its entirety) disclose a nucleic acid amplification process involving cyclically synthesizing single-stranded RNA ("ssRNA"), ssDNA, and double-stranded DNA (dsDNA), which may be used in accordance with the present invention. The ssRNA is a template for a first primer oligonucleotide, which is elongated by reverse transcriptase (RNA-dependent DNA polymerase). The RNA is then removed from the resulting DNA:RNA duplex by the action of ribonuclease H(RNase H, an RNase specific for RNA in duplex with either DNA or RNA). The resultant ssDNA is a template for a second primer, which also includes the sequences of an RNA polymerase promoter (exemplified by T7 RNA polymerase) 5' to its homology to the template. This primer is then extended by DNA polymerase (exemplified by the large "Klenow" fragment of *E. coli* DNA polymerase I), resulting in a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller et al., Int. Pat. Appl. Publ. No. WO 89/06700 (incorporated herein by reference in its entirety) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR™" (Frohman, 1990, specifically incorporated herein by reference).

Methods based on ligation of two (or more) oligonucleotides in the presence of nucleic acid having the sequence of the resulting "di-oligonucleotide," thereby amplifying the di-oligonucleotide, may also be used in the amplification step of the present invention.

Following any amplification, it may be desirable to separate the amplification product from the template and the excess primer for the purpose of determining whether specific amplification has occurred. In one embodiment, amplification products are separated by agarose, agarose-acrylamide or polyacrylamide gel electrophoresis using standard methods (see e.g., Sambrook et al., 1989).

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography.

Amplification products must be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In one embodiment, visualization is achieved indirectly. Following separation of amplification products, a labeled, nucleic acid probe is brought into contact with the amplified marker sequence. The probe preferably is conjugated to a chromophore but may be radiolabeled. In another embodiment, the probe is conjugated to a binding partner, such as an antibody or biotin, and the other member of the binding pair carries a detectable moiety.

In one embodiment, detection is by Southern blotting and hybridization with a labeled probe. The techniques involved in Southern blotting are well known to those of skill in the art and can be found in many standard books on molecular protocols. See Sambrook et al., 1989. Briefly, amplification products are separated by gel electrophoresis. The gel is then contacted with a membrane, such as nitrocellulose, permitting transfer of the nucleic acid and non-covalent binding. Subsequently, the membrane is incubated with a chromophore-conjugated probe that is capable of hybridizing with a target amplification product. Detection is by exposure of the membrane to x-ray film or ion-emitting detection devices.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

5.0 EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

5.1 Example 1

Preparation of Ribozyme and Selection of Ribozyme Targets

Targets for ribozymes are chosen from complete cDNA sequences or 100-300 nt expressed sequence tags from among genes that are highly expressed in photoreceptor cells or the retinal pigment epithelium. Targets consist of 4 nucleotides 5' and 6 nucleotides 3' of the nucleotide triplets GUC, CUC, UUC or AUC. Analysis of possible secondary structure of the 25 nt sequence containing the target sites is made using the MFOLD algorithm (http://mfold2.wustl.edu/rna/form.cgi, Genetics Computer Group, Madison, Wis.), and targets likely to be embedded in local stem structures are avoided. Ribozyme-accessible sites may also be detected by treatment with single-strand RNA-specific modifying reagents (Shaw and Lewin, 1995).

Figures 5, 6:
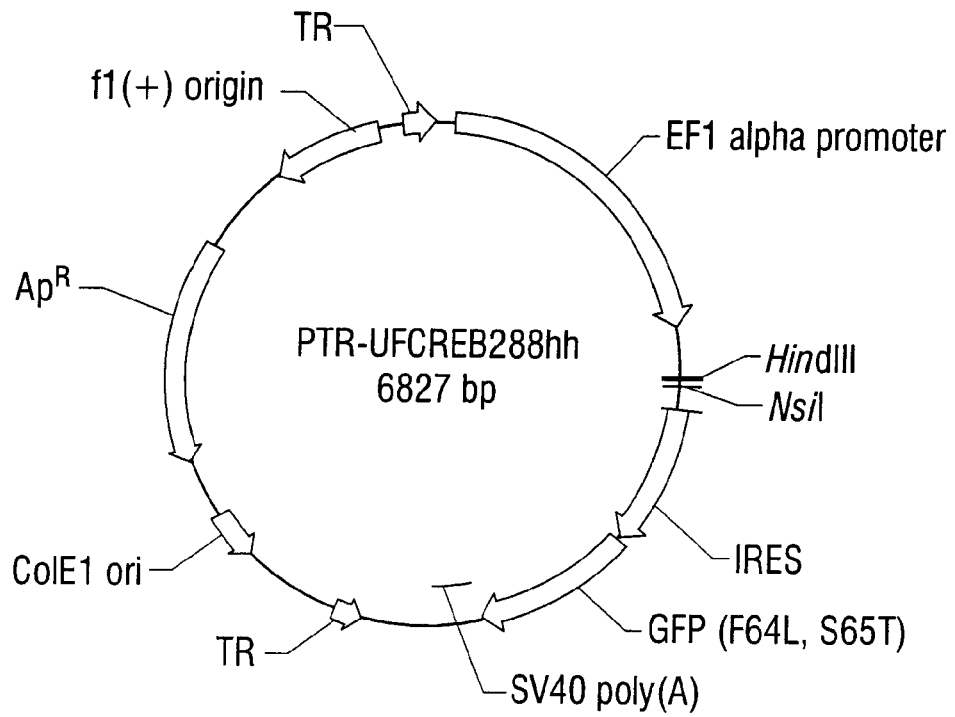
FIG. 5 shows a plasmid map of pTR-UFCREB288 hh.
FIG. 6 shows the nucleotide sequence (SEQ ID NO:1) and structure of a degenerate hammerhead ribozyme, including RNA target sequence (SEQ ID NO:2).
Figure 7:
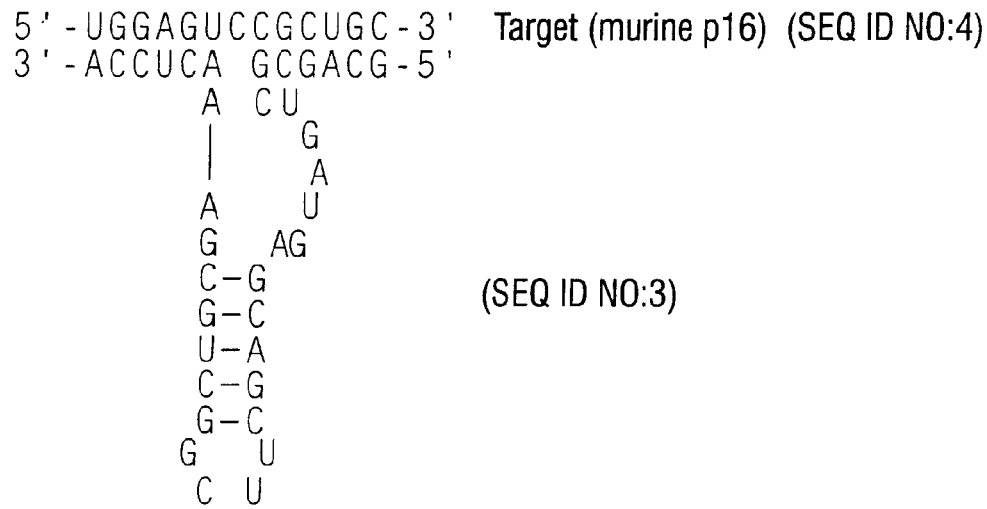
FIG. 7 shows the nucleotide sequence (SEQ ID NO:3) and structure of an anti-p16 hammerhead ribozyme, including RNA target sequence (SEQ ID NO:4; murine p16).
Figure 8:
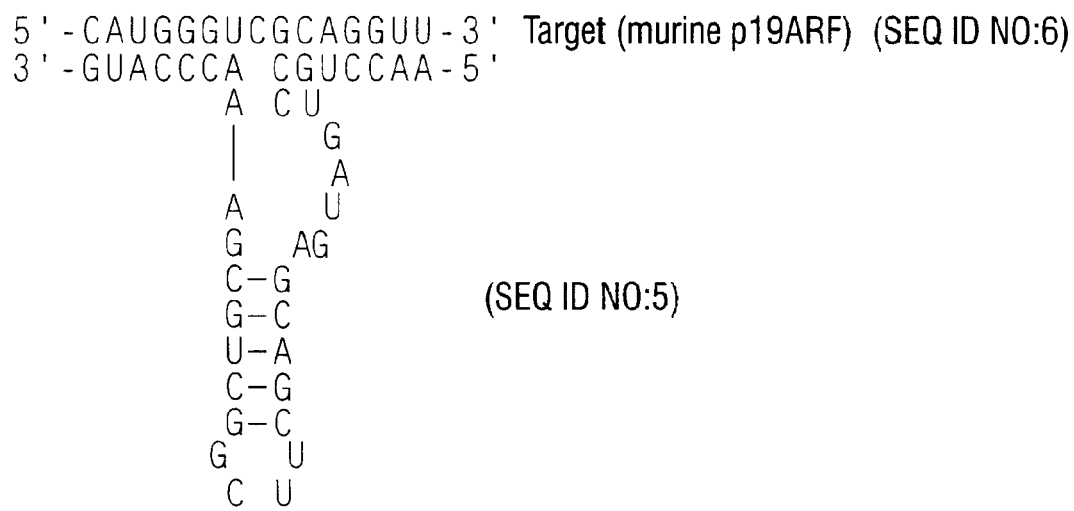
FIG. 8 shows the nucleotide sequence (SEQ ID NO:5) and structure of an anti-p19ARF hammerhead ribozyme, including RNA target sequence (SEQ ID NO:6; murine p19ARF).
Figure 9:
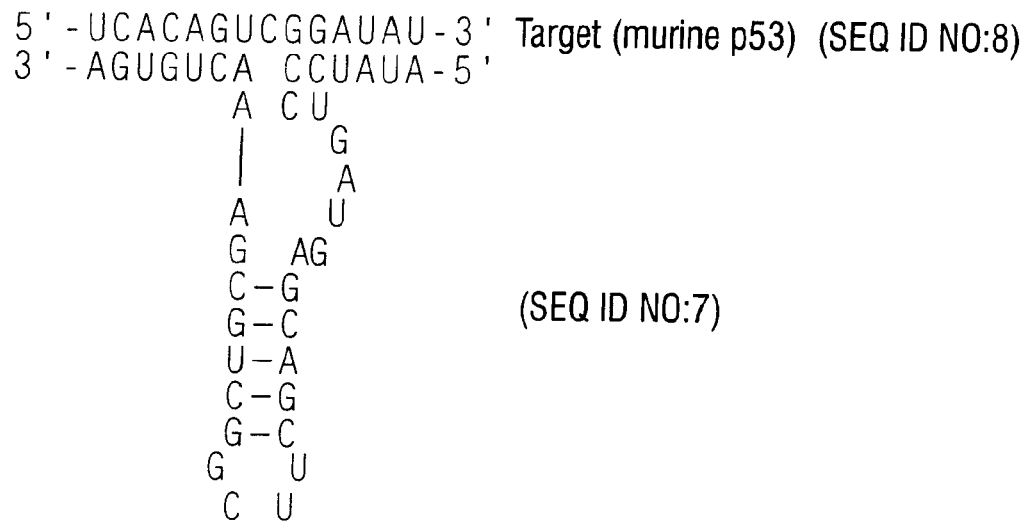
FIG. 9 shows the nucleotide sequence (SEQ ID NO:7) and structure of an anti-p53 hammerhead ribozyme, including RNA target sequence (SEQ ID NO:8; murine p53).

Hammerhead ribozymes of the general structure shown in FIG. 6 are designed, where N can represent any ribonucleotide, and are complementary to the ribonucleotides of the target sequence. There are alternative forms (and sequences) of the stem-loop structure shown that are likely to function as well as that shown in FIG. 6, and are thus also contemplated for use in the present invention.

Target sequences of 14 nucleotides and cognate ribozymes are chemically synthesized and obtained from a commercial vendor (Dharmacon, Inc. Boulder, Colo.). Protecting groups are removed from the 2' positions of RNA oligonucleotides according to the manufacturer's instructions, and oligonucleotides are labeled with polynucleotide kinase and [$\gamma$-$^{32}$P]ATP at 37° C. for 30 minutes and then is diluted to 100 µl with sterile water and extracted with phenol:chloroform:isoamyl alcohol (50:50:1) to inactivate the enzyme. Unincorporated nucleotides are removed by passing the aqueous phase over a G-25 Sephadex spin column. Ribozymes or larger targets (>30 nucleotides) are purified on 8% acrylamide, 8M urea sequencing gels run in TBE buffer (89 mM Tris borate, pH 8.3, 20 mM EDTA). Labeled molecules are visualized by autoradiography, excised with a sterile scalpel, and eluted from the gel in 1 M NH$_4$OAc, 50 mM Tris HCl, pH 7.5, 20 mM EDTA, 0.5% SDS at 37° C. for 1-4 hours. In embodiments where the gel purification is omitted, the transcript is treated with RNase-free DNase I to remove DNA sequences that may anneal to the target or to the ribozyme.

Specific radioactivity of each molecule is used to calculate the concentration of target and ribozyme molecules. Analyses to determine multiple turnover kinetic constants are typically carried out in 20 mM MgCl$_2$, 40 mM Tris-HCl, pH 7.5, at 37° C. for short intervals. The appropriate interval is determined by a time-course experiment under multiple turnover conditions (i.e. substrate excess). Cleavage products for target RNAs produced by in vitro transcription are analyzed by electrophoresis on 8 or 10% acrylamide 8 M urea sequencing gels run in TBE. Initial rates are measured when the amount of cleavage is linear with time and when no more than 10% of substrate has been converted to product. Rates are measured at several intervals (e.g., 5, 10 and 20 min) to insure linearity. Samples are pre-incubated at 37° C. prior to initiation of cleavage and contain 1-10 nM ribozyme and increasing concentrations of substrate RNA, holding ribozyme concentration constant. Substrate concentrations greatly exceed ribozyme concentration, the lowest being in 5-fold excess. Kinetic parameters are obtained by double reciprocal plots of velocity versus substrate concentration (Lineweaver-Burke plots) or by plots of reaction velocity versus the ratio of velocity to substrate concentration (Eadie-Hofstee plots). Ribozymes with a $k_{cat}$ of less than 0.5 min or a $K_M$>5 µM are discarded.

Figure 1:
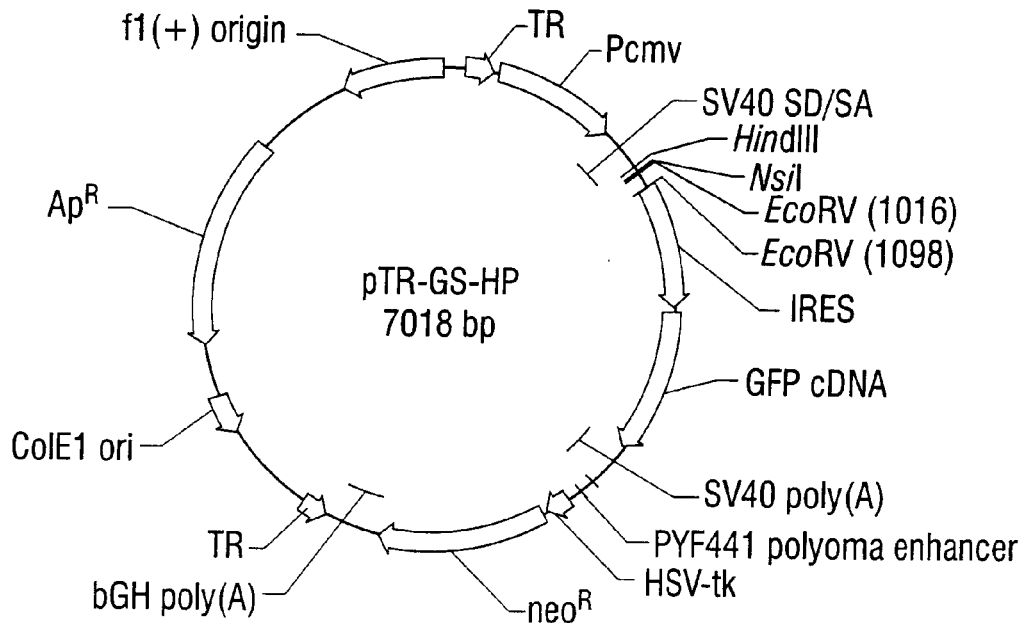
FIG. 1 shows a plasmid map of pTR-GS-HP.

DNA oligonucleotides encoding kinetically competent ribozymes are cloned in a derivative of AAV vector pTR-GS-HP (FIG. 1). Oligonucleotides contain a cleavage site for restriction enzyme HindIII 5' and for NsiI 3' to permit insertion into this vector. This 7-kb vector encodes a hairpin ribozyme that cleaves internally and reveals the hammerhead ribozyme directed at the target of interest at the 3'-end of the RNA. The primary transcript also contains the humanized GFP gene (Zolotukhin et al., 1996), the gene for neomycin resistance driven by the HSV thymidine kinase promoter, followed by the bovine growth hormone polyA site. The CMV promoter present in the original vector has been replaced by the 472 base pair mouse opsin proximal promoter (Flannery et al., 1997) for expression in rod photoreceptor cells, with a deleted version of the red cone specific promoter (Nathans et al., 1986), or with a 2.6 kb RPE-specific promoter from the CRALBP gene (GenBank Accession No. AF084638).

5.1.1 Construction of the Vector Backbone

AAV vectors are packaged using a 2-plasmid transfection system and EK 293 cells as follows. To produce rAAV, a triple co-transfection procedure is used to introduce a rAAV vector plasmid together with pACG2 AAV helper plasmid and pXX6 Ad helper plasmid (Xiao et al., 1998) at a 1:1:1 molar ratio. Alternatively, rAAV vector plasmid is co-transfected with the helper plasmid pDG carrying the AAV rep and cap genes, as well as Ad helper genes required for rAAV replication and packaging (Grimm et al., 1998). Plasmid DNA used in the transfection is purified by a conventional alkaline lysis/CsCl gradient protocol. The transfection is carried out as follows: 293 cells are split 1:2 the day prior to the experiment, so that, when transfected, the cell confluence is about 75-80%. Ten 15-cm plates are transfected as one batch. To make CaPO$_4$ precipitate, 180 µg of pACG2 is mixed with 180 µg of rAAV vector plasmid and 540 µg of pXX6 in a total volume of 12.5 ml of 0.25 M CaCl$_2$. Alternatively, 0.7 mg of pDG and 180 µg of rAAV vector plasmid are mixed in the same volume. The old media is removed from the cells and the formation of the CaPO$_4$-precipitate is initiated by adding 12.5 ml of 2×HBS pH 7.05 (pre-warmed at 37° C. to the DNA-CaCl$_2$ solution. The DNA is incubated for 1 min; and transferring the mixture into pre-warmed 200 ml of DMEM-10% FBS stops the formation of the precipitate. Twenty-two ml of the media is immediately dispensed into each plate and cells are incubated at 37° C. for 48 hrs. The CaPO$_4$-precipitate is allowed to stay on the cells during the whole incubation period without compromising cell viability. Forty-eight hr post-transfection cells are harvested by centrifugation at 1,140×g for 10 min; the media is discarded. Cells are then lysed in 15 ml of 0.15 M NaCl, 50 mM Tris HCl pH 8.5 by 3 freeze/thaw cycles in dry ice-ethanol and 37° C. baths. Benzonase™ (Nycomed Pharma A/S, pure grade, Benzon Pharma A/S, Roskilde, Denmark) is added to the mixture (50 U/ml, final concentration) and the lysate is incubated for 30 min at 37° C. The lysate is clarified by centrifugation at 3,700×g for 20 min and the virus-containing supernatant is considered the crude lysate, from which a high titer stock can be prepared using standard protocols. No helper adenovirus is used in this preparation. Infectious titers are routinely $10^{10}$-$10^{11}$ virus per milliliter.

5.1.2 Assay of Ribozyme Activity

To test for the function of target genes, 2 μl of AAV-expressing ribozymes are injected subretinally in the right eyes of 15-day-old mice, under general and local anesthetic. This leads to a local retinal detachment that resolves within minutes. Groups of 8 mice are used for each ribozyme construct, and the left eyes of these animals are untreated and serve as controls. Animals which develop cataracts as a result of the injection or which show signs of injury or inflammation are removed from the study and euthanized.

At 6 weeks of age (4 weeks post injection) animals are assayed for retinal function by electroretinography (ERG) and for retinal thickness by optical coherence tomography (OCT) (Ripandelli et al., 1998; Jacobson et al., 1998). For ERG, mice are dark adapted overnight, and then in dim red light anesthetized with intramuscular injections of xylazine (13 mg/kg) and ketamine (87 mg/kg). Full-field scotopic ERGs are elicited with 10-μsec flashes of white light and responses are recorded using a UTAS-E 2000 Visual Electrodiagnostic System (LKC Technologies, Inc., Gaithersburg, Md.). The corneas of the mice are anesthetized with a drop of 0.5% proparacaine hydrochloride, and the pupils are dilated with 1% atropine and 2.5% phenylephrine hydrochloride. Small contact lenses with gold wire loops are placed on both corneas with a drop of 2.5% methylcellulose to maintain corneal hydration. A silver wire reference electrode is placed subcutaneously between the eyes and a ground electrode is placed subcutaneously in the hind leg. Stimuli are presented at intensities of −1.1, 0.9 and 1.9 log cd m$^{-2}$ at 10-second, 30-second and 1-minute intervals, respectively. Responses are amplified at a gain of 4,000, filtered between 0.3 to 500 Hz and digitized at a rate of 2,000 Hz on 2 channels. Three responses are averaged for each intensity. The a-waves are measured from the baseline to the peak in the cornea-negative direction, and b-waves are measured from the cornea-negative peak to the major cornea-positive peak. For quantitative comparison of differences between the two eyes of mice, the values from all the stimulus intensities are averaged for a given animal.

This analysis is repeated at 16 weeks of age, at which time all animals are euthanized. Left and right eyes of the animals showing evidence of retinal degeneration (by either ERG or OCT) are fixed in a mixture of mixed aldehydes (2% formaldehyde and 2.5% glutaraldehyde). Eyes are embedded in epoxy resin, and 1-μm thick histological sections are made along the vertical meridian. Tissue sections are aligned so that the ROS and Müller cell processes crossing the inner plexiform layer are continuous throughout the plane of section to assure that the sections are not oblique, and the thickness of the ONL and lengths of RIS and ROS are measured (Faktorovich et al., 1990). RPE and choroidal layers are examined for evidence of neovascularization, RPE cell death or abnormal deposits.

AAV-ribozymes that lead to retinal degeneration are tested a second time in a similar protocol to confirm the result. EST clones are identified as containing ribozyme targets the cleavage of which leads to retinal dystrophy in animals. Clamped PCR™ methods (5' and 3' RACE) are used to sequence the entire cDNAs for ESTs containing those targets. Searches of GenBank and other sequence databases are made to identify known genes or similarity to genes of known function. The tissue distribution of gene expression of ESTs of interest is determined by Northern hybridization of RNA extracted from a variety of mouse tissues.

5.1.3 Identification of Candidate Genes

In situ hybridization analysis is used to map the general genomic location of previously unknown genes. This is followed by mapping of the gene by hybridization to YAC, BAC and cosmid clones of the mouse genome. Based on the synteny between the human and mouse genomes, this information is used to map genes of interest in intervals of the human genome. In these way regions containing candidate genes for inherited retinal disease are identified. Of particular interest are loci mapped on the human genome that contain unknown genes responsible for retinal degeneration (Daiger et al., 1998).

Similar analysis is performed for all three retinal-specific promoters. Because these promoters function in a retinal specific manner in a variety of mammals, similar analysis is conducted using other animal models. For example, AAV-ribozymes are tested in the cone-rich retina of pigs and in the macular retina of rhesus macaques.

The 7-kb vector pTR-GS-HP (FIG. 1) contains a hairpin ribozyme between the two EcoRV sites. The hairpin ribozyme cleaves directly upstream of its position and can thereby reveal the hammerhead ribozyme. This ribozyme is directionally cloned between the HindIII (5') and the NsiI (3') site. The ribozyme library and the "positive control" ribozymes (p53, p16, Rb, p19ARF) have been cloned. The downstream portion of the transcript contains an IRES element where translation of the humanized gfp gene is initiated (Zolotukhin et al., 1996). The HSV-TK promoter drives the neomycin resistance gene.

In pTR-UF33-HP (FIG. 2) the CMV promoter, which is silenced in the liver, has been substituted by the EF1 promoter (human elongation factor 1α, GenBank Accession No. E02627; Kim et al., 1990). This promoter is highly active in a variety of tissues in vivo and does not exhibit any silencing. The vector pTR-UF12-HP (FIG. 3) contains the CMV-IE enhancer-chicken-β-actin hybrid promoter (Sawicki et al., 1998; GenBank Accession No. E03011) in place of the CMV promoter.

5.2 Example 2

Candidate Genes for Retinal Degeneration 5.2.1 β-Subunit of Mouse cGMP Phosphodiesterase Using the rod opsin promoters that are well characterized in vivo a retinitis pigmentosa (RP)-like rod degeneration was created in rd/+mice (Bowes et al., 1990; Bennett et al., 1998). These mice have one rd allele and one wild-type allele of the gene for the β-subunit of cGMP phosphodi-esterase (βPDE; GenBank Accession No. X55968), and have an apparently normal retina at all ages. In the homozygous condition, the rd/rd mouse is a classical animal model for recessive RP, losing all rods within a month or two after birth.

A ribozyme was designed (FIG. 15) that digested the normal allele RNA well in vitro, but that did not cleave rd RNA. This ribozyme also specifically cleaved full length normal βPDE mRNA in a total retinal RNA preparation. This ribozyme was then packaged into rAAV downstream of a proximal rod opsin promoter, as described herein below, and injected into one eye of a series of rd/+mice. At 4 months postinjection, approximately 50% fewer photoreceptor nuclei were found in the outer nuclear layers of the ribozyme treated eyes relative to contralateral control eyes (FIG. 16A, FIG. 16B, FIG. 16C and FIG. 16D). Control eyes were similarly injected either with PBS carrier (FIG. 16A) or rAAV containing an inactive ribozyme (FIG. 16C). These studies provide morphological evidence that ribozymes against a photoreceptor specific wild-type mRNA can create retinal degeneration.

5.2.2 γ-Subunit of Mouse cGMP Phosphodiesterase

Two novel ribozymes have been generated that target the gamma subunit of the cyclic GMP phosphodiesterase. These are termed HHRZ35 and HHRZ42 (FIG. 18A and FIG. 18B, respectively). Both cleave the mRNA for gamma-PDE efficiently and lead to retinal degeneration in a mouse. Two ribozymes have also been designed against a photoreceptor cell EST clone obtained as described above. These were termed HHRZ52 (FIG. 34) and HHRZ282 (FIG. 35). These have been cloned in pT7T3-19.3. Two additional ribozymes against the wild-type ABCR gene: Human ABCR Rz114 (FIG. 17A) and Mouse ABCR Rz (FIG. 17B), which is mutated in Stargardt's macular dystrophy, have also been prepared that are useful in generating animal models of macular disease. One ribozyme is specific for rat and the other will cleave the human, macaque and rat mRNA. This latter ribozyme has been tested extensively in vitro and has been injected into rhesus macaques using an AAV vector with containing the mouse opsin promoter to demonstrate the elicitation of retinal degeneration in vivo.

5.3 Example 3

Candidate Tumor Suppressor Genes

The analysis of DNA isolated from malignant tumors has identified two major groups of genes that are involved in tumorigenesis, oncogenes and tumor suppressor genes (Knudson 1993). The former is a group of genes that are overactive or constitutively active due to certain mutations and lead to uncontrolled cell growth. These genes often are transcription factors, such as the ras-family, or genes that drive the cell cycle into G1 and S phase (Collins et al., 1997). The latter group, tumor suppressor genes, inhibits progression of the cell cycle. The major role of tumor suppressor genes such as p53, p16, Smad4 (DPC4) or Rb in tumorigenesis is widely recognized. They also play an important role in determining the biological behavior of (metastasis, growth dynamics, invasion) of malignant tumors (Vogelstein and Kinzler, 1993). Although roughly 20 tumor suppressor genes are known, an estimated 100 exist. Currently, the search and discovery of new potential tumor suppressor genes is a long and laborious process.

A library of hammerhead ribozymes is delivered by recombinant AAV to several tissues (liver, skeletal muscle, epithelium of the small and large intestine, retina). Recombinant AAV has been shown to stably express a transgene at high levels in various tissues (brain, liver, skeletal muscle, retina, intestinal epithelium) for up to 18 months (Klein et al., 1998; Song et al., 1998; Flannery et al., 1997; Herzog et al., 1997; During et al., 1998; Fisher et al., 1997). Ribozymes contained in the library that target a tumor suppressor gene cause a tumor to arise from that particular cell. The tumor growth itself is an amplification step that makes the isolation of that individual ribozyme more straightforward. Using the specific recognition sequence of these ribozymes, new potential tumor suppressor genes are discovered.

In order to facilitate the induction of malignant tumors, ribozymes against known tumor suppressor genes (p53, p16, p19ARF and Retinoblastoma (Rb); "positive control" ribozymes) are injected in combination with the library. The probability of infecting a single cell with two recombinant AAV vectors at the same time (e.g., in the liver) is approximately 5-10%. As a "positive control" ribozymes that target known tumor suppressor genes, e.g., are included. They are injected individually or in combination to induce tumor development in mice.

Tumorigenesis is a multi-step process that involves a series of genetic alterations and mutations (Vogelstein and Kinzler, 1993). The two major groups of genes that are involved in this process are oncogenes and tumor suppressor genes (Knudson, 1993). Mutations in the two tumor-suppressor genes encoding p53 and the retinoblastoma protein (Rb), which function as important regulators of the cell cycle, lead to transformation of the cell and ultimately autonomous tumor growth (Collins et al., 1997). The causative role of tumor suppressor genes in the development of malignant tumors has further been validated by the generation of knockout mice for these genes. p53 knock-out or p16 knock-out mice are highly susceptible to spontaneous tumor development (Jacks et al., 1994; Serrano et al., 1996). Moreover, if two tumor suppressor genes, such as p53 and Rb, are inactivated at the same time the mice become even more susceptible to cancer (Harvey et al., 1995). Tumor suppressor genes also play an important role in determining the biological behavior (growth dynamics, invasion, metastasis) of malignant tumors (Vogelstein and Kinzler, 1993).

Although a number of genes and pathways that are involved in the regulation of the cell cycle and cell replication have been identified as tumor suppressor genes other, so far unknown genes associated with, or perhaps independent of these pathways certainly play a role in controlling this process. Estimates of the total numbers of tumor suppressor genes run in the hundreds.

5.3.1 Methods

A library of ribozymes packaged into recombinant AAV are delivered to various tissues in mice. If one (or more) of the ribozymes contained in the library targets a tumor suppressor gene, cells producing this ribozyme may give rise to a tumor. The growth of the tumor constitutes an amplification of that particular ribozyme against the background of the library, making the isolation of that ribozyme possible. The specific target sequence are then determined and used as a probe for the identification of novel tumor suppressor genes.

For this purpose, a degenerate hammerhead ribozyme (library) was designed (FIG. 5). The nucleotides GUC at the target sequence, which are necessary for efficient cleavage, are flanked by a total of 11 degenerate nucleotides (5 and/or 6 on each side). The complexity of the library is therefore $4.19 \times 10^6$. The ribozyme library has been cloned into recombinant AAV (rAAV) vectors. Either the elongation factor-1α promoter or the CMV immediate early enhancer/chicken β-actin promoter is used to drive the transcription of the ribozyme in two otherwise identical libraries. These promoters are both known to direct sustained, high-level expression of marker genes in a wide variety of tissues. Immediately downstream of the hammerhead ribozyme is a hairpin ribozyme that cleaves the transcript internally and liberates the hammerhead ribozyme for better activity.

Figure 10A:
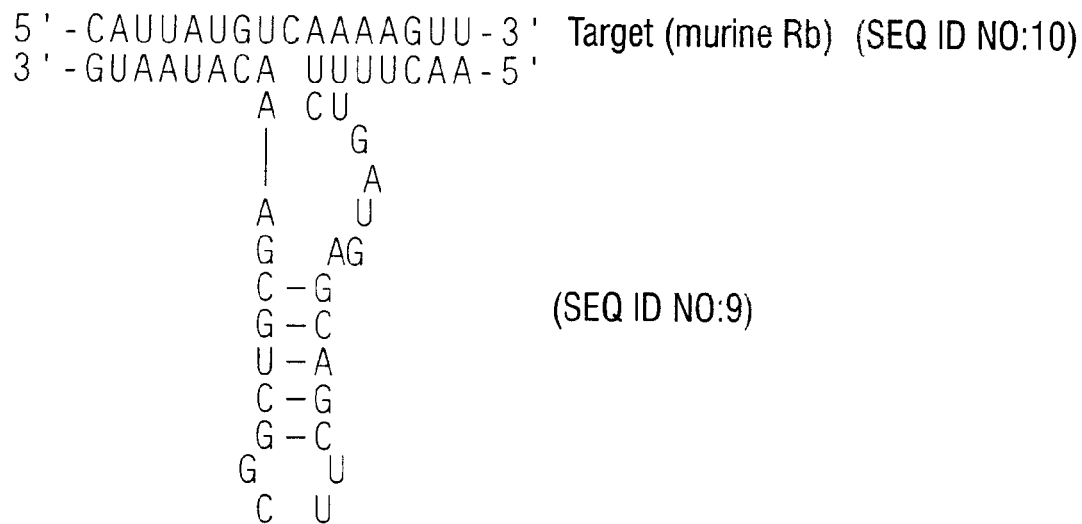
FIG. 10A shows the nucleotide sequence (SEQ ID NO:9) and structure of an anti-retinoblastoma hammerhead ribozyme, including RNA target sequence (SEQ ID NO:10; murine retinoblastoma).
Figure 10B:
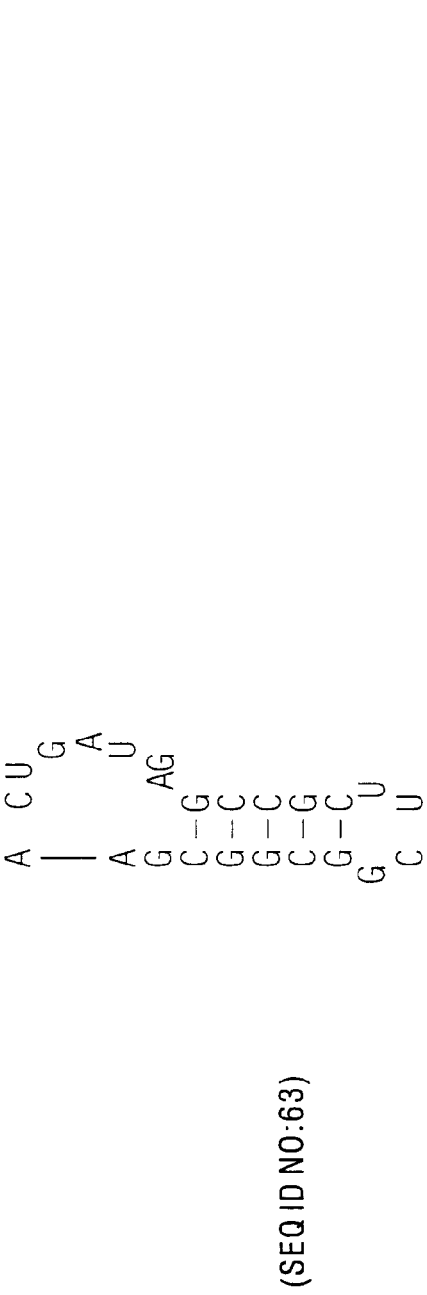
FIG. 10B shows the nucleotide sequence (SEQ ID NO:63) and structure of an anti-retinoblastoma hammerhead ribozyme, including RNA target sequence (SEQ ID NO:64; murine retinoblastoma).

After packaging, recombinant virus are delivered to various tissues in mice (skeletal muscle, liver, neuronal tissue, mammary glands). Protocols for packaging and purification of rAAV routinely provide titers of $10^{12}$ infectious units per milliliter, meaning that tissues will be infected at high multiplicity. Recombinant AAV has been shown to stably express marker genes at high levels in these tissues for up to 24 months (Klein et al., 1998; Song et al., 1998; Herzog et al., 1997). In order to facilitate the induction of tumors in vivo, the packaged ribozyme library are injected as a mixture with virus carrying ribozyme against known tumor suppressor genes. Hammerhead ribozymes that target Rb (FIG. 10A and FIG. 10B), p53, p16 and p19 have been designed and successfully tested in vitro (FIG. 6). These ribozymes are also used in combinations as positive controls.

Once a tumor has developed in injected mice, it is analyzed by standard histology techniques, and a cell-line will be established if possible. The ribozyme itself can be amplified by RT-PCR from tumor RNA. Alternatively, the portion of the vector containing the ribozyme may be amplified by standard PCR from DNA. An rAAV expressing this ribozyme may be generated to confirm that this virus alone can induce tumors in specific tissues. Sequencing can identify the 14 base pair recognition sequence of that ribozyme, and this sequence-tag will be used to screen DNA databases (e.g., GenBank). If the sequence matches a known gene involved in cell growth regulation or, in fact, a known tumor-suppressor gene, this result serves as an internal positive control and validates the overall method.

In some cases a tumor may develop because more than one tumor suppressor gene has been inactivated. One of the potential strengths of this approach is the fact that several ribozymes within the library are delivered simultaneously to the same cell and act in a combinatorial fashion. The initial tumors that are screened will, therefore, result in the isolation of an enriched subpopulation of ribozymes. To identify the ribozymes that were responsible for tumor induction, the enriched subpopulation is then re-cloned in AAV vectors and re-injected into animals. In this manner, the minimum ribozyme (i.e. tumor suppressor) combination necessary for tumor induction is identified for each target tissue.

5.3.2 Construction/Cloning of the Hammerhead Ribozyme Library

The degenerate hammerhead ribozyme (library ribozyme) has the structure shown in FIG. 6. The bases GUC are fixed, as they comprise the cleavage site. Six bases on the 5' end and 5 bases on the 3' end are degenerate. Therefore the specific recognition sequence of any given ribozyme of the library is 14 bases. Since there are 11 degenerate nucleotides the complexity of the library is $4^{11}$ which equals $4.2 \times 10^6$.

Two DNA-oligonucleotides (oligos) are designed with the respective nucleotides being degenerate. The sense and antisense oligos overlap 12 base pairs. The oligos are annealed in buffer containing 50 mM NaCl, 10 mM Tris-HCl, 10 mM $MgCl_2$, 1 mM dithiothreitol (pH 7.9). The overhanging ends are filled in with DNA polymerase Klenow fragment in the presence of 0.1 mM dNTP. They are digested sequentially with the two enzymes HindIII and NsiI. The double stranded library ribozyme oligo is purified on a 12% non-denaturing poly acrylamide gel.

The backbone vectors are sequentially cut with HindIII and NsiI and purified on an agarose gel. 300 ng of the vector is used per ligation reaction. The optimal amount of insert (library ribozyme) oligo is determined by a set of test ligations with a titration of the insert. Once the optimal vector:insert ratio is found, a sufficient number of ligation reactions are set up.

The ligation is transformed into Supercompetent Surecells (Epicuran Coli® SURE® Electroporation Competent Cells, Stratagene, La Jolla, Calif.). With the optimal vector: insert ratio approximately $2.0$-$2.5 \times 10^6$ colonies per transformation are achieved.

A sufficient multiple of the complexity of the library is obtained when performing 20 transformations. The transformations are pooled and plated out on LB-agar containing 50 μg/ml ampicillin and grown overnight at 37° C. The colonies are counted on a set of dilutions to obtain the exact number of colonies. The colonies are washed off the plate in a total of 100 ml of LB media. Aliquots of 2 ml are frozen down as a glycerol stock.

Plasmid DNA is isolated on a CsCl gradient by standard techniques (Sambrook et al., 1989) in sufficient quantities.

5.3.3 Packaging of AAV-Vectors

AAV vectors are packaged as described in Example 1 above.

5.3.4 Injection of Recombinant AAV into Animals

Each animal is injected with $10^{10}$ infectious units. For each procedure the mice are lightly anesthetized with an inhalant anesthetic methoxyfluorane (Metofane™, The Dow Chemical Company, Midland, Mich.; Johnson & Johnson, New Brunswick, N.J.). The application sites are skeletal muscle, intravenous (tail vein), peroral application and peranal application.

For skeletal muscle injection, recombinant AAV in a volume of 50 μl is injected into the hamstring muscle group of both hind legs. A 1-ml syringe with a 28-Gauge needle is used. For better visualization the coat over the injection site is removed with a razor. For tail vein injection, each mouse is restrained in a Plexiglas™ (Rohm & Haas Company, Philadelphia, Pa.) box by holding the mouse by its tail for the duration of the injection. The AAV suspension in a total volume of 100 μl is slowly injected into one of the tail veins. For peroral application, an orogastric tube is carefully inserted. The AAV suspension is administered through this tube in a total volume of 100 μl. Mice are then allowed to recover and returned to ad libitum access to water and standard mouse diet. For peranal application, 100 μl of recombinant AAV are instilled by an enema. A total of 50 animals are injected for each route of application.

The injected mice are monitored on a regular basis (twice weekly) by weighing them and by "clinical assessment." If any signs of an obvious tumor are discovered or if a mouse loses more than 20% of its bodyweight the mouse is sacrificed and an autopsy is performed. All relevant organs (brain, heart, lung, liver, kidneys, spleen, injected skeletal muscle, stomach, large and small bowel) are harvested and a blood sample is taken. The injected sites are carefully examined for any tumors. Tumors are divided into three pieces and analyzed as described in the flow sheet shown in FIG. 14.

5.3.5 Tumor Analysis

Tumors are fixed in 4% paraformaldehyde in PBS, pH 7.5 for 2 days followed by equilibration in 30% sucrose in PBS pH 7.5 until equilibrated. The samples are frozen at −20° C. and cryosectioned on cryostat. GFP expression is analyzed under fluorescent light microscope.

For primary tissue culture, the tumor tissue is mechanically dissociated and placed in RPMI 1640 media, 15% FCS. The cells are split as necessary. If necessary tumor cells are separated from fibroblasts by selectively trypsinizing. GFP expression is analyzed under the fluorescent light microscope or by FACScan™ (Becton Dickinson and Company, Franklin Lakes, N.J.) analysis.

The isolation of genomic RNA and total DNA is carried out according to standard procedures (Sambrook et al., 1989). DNA analysis (Southern Blot) and RNA analysis (Northern Blot) is carried out according to standard procedures (Sambrook et al., 1989).

For RT-PCR™, cDNA is synthesized with reverse transcriptase (Gibco BRL) according to the manufacturer's instructions. The PCR™ is carried out with a Perkin-Elmer PCR™ Kit according to the manufacturer's instructions. For PCR™ of genomic DNA, a Perkin-Elmer PCR™ Kit with pfu-polymerase is used. The manufacturer's instructions are followed. The following primers are used: sense 5'-GGACT-GTCAGATATCG-3' (SEQ ID NO:27); antisense 5'-ACT-GAGTGGGTGGAGACTGA-3' (SEQ ID NO:28).

The PCR™-fragments are subcloned into pT7/T3-19 at the restriction sites HindIII and NsiI by standard techniques for sequence analysis. A standard T7 sequencing primer is used. For sequencing a Big Dye Sequencing Kit is used. A cDNA library screen is carried out by standard procedures (Sambrook et al., 1989).

Alternatively, Balb C 3T3 fibroblasts may be used to select sub-libriaries of potentially oncogenic ribozymes, which are then re-tested in mice by the method described above.

5.4 Example 4

Candidate Genes Involved in Memory and Learning

The formation of long-term memories involves the expression of genes; disruption of mRNA and protein synthesis affects memory formation (Rosenzweig, 1996). For the last two decades scientists have been looking for candidate genes involved in this process using pharmacological and genetic techniques. The hippocampus has been shown to be the locus for memory, since lesions in this region result in impaired acquisition of spatial memory (Morris et al., 1990). CREB, a ubiquitous transcription factor that binds the cAMP responsive element (Gonzalez et al., 1989), has been shown to play a role in the switch from short term to long-term memory in Aplysia, drosophila, mice and rats (Silva et al., 1998). CREB deficient knockout mice, and antisense CREB injected rats present memory abnormalities (Silva et al., 1998; Guzowski et al., 1997). Because virus-targeted ribozymes are well suited for studying learning and memory where temporal and spatial specificity are critical, ribozymes directed to CREB mRNA are chosen to knock out CREB expression. This approach is also used to alter the expression of a number of downstream targets of CREB, as well as novel genes. The ability to disrupt these neuronal functions is important in the development of animal models for neurological disorders.

In brief, appropriate ribozymes that target CREB mRNA are designed and cloned, and these ribozymes are shown to cleave their target RNA substrate both in vitro and in vivo. Then, the levels of hippocampal CREB protein are analyzed to detect the decrease in CREB ribozyme injected animals. Loss of function of Long Term Memory (LTM) in rats is studied using the Morris water maze-learning paradigm (Morris, 1981). Differential display methods are used to identify other candidate genes involved in learning and memory, and the process outlined above is repeated for these newly identified genes.

Figure 2:
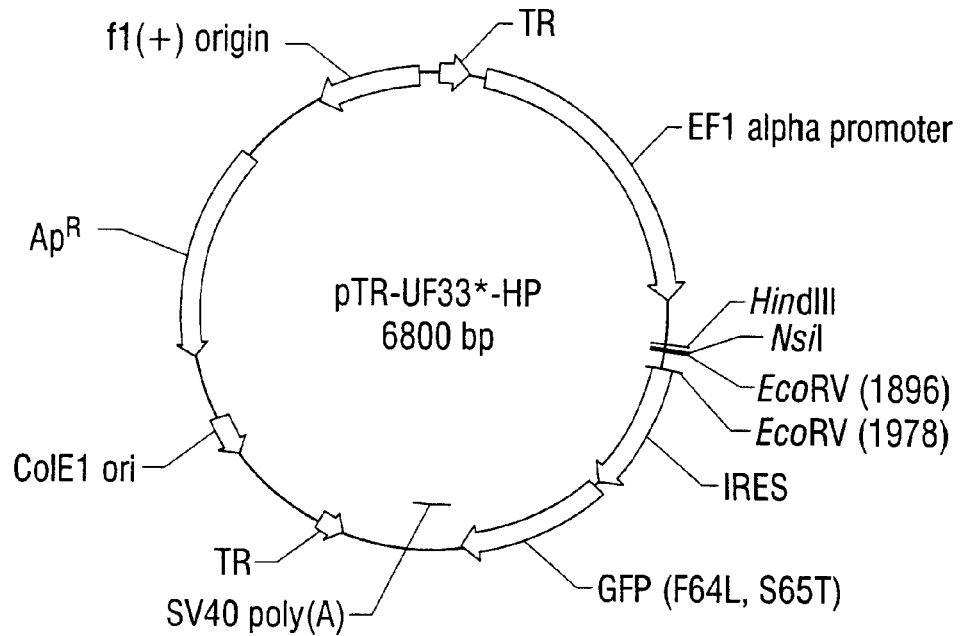
FIG. 2 shows a plasmid map of pTR-UF33*-HP.
Figure 3:
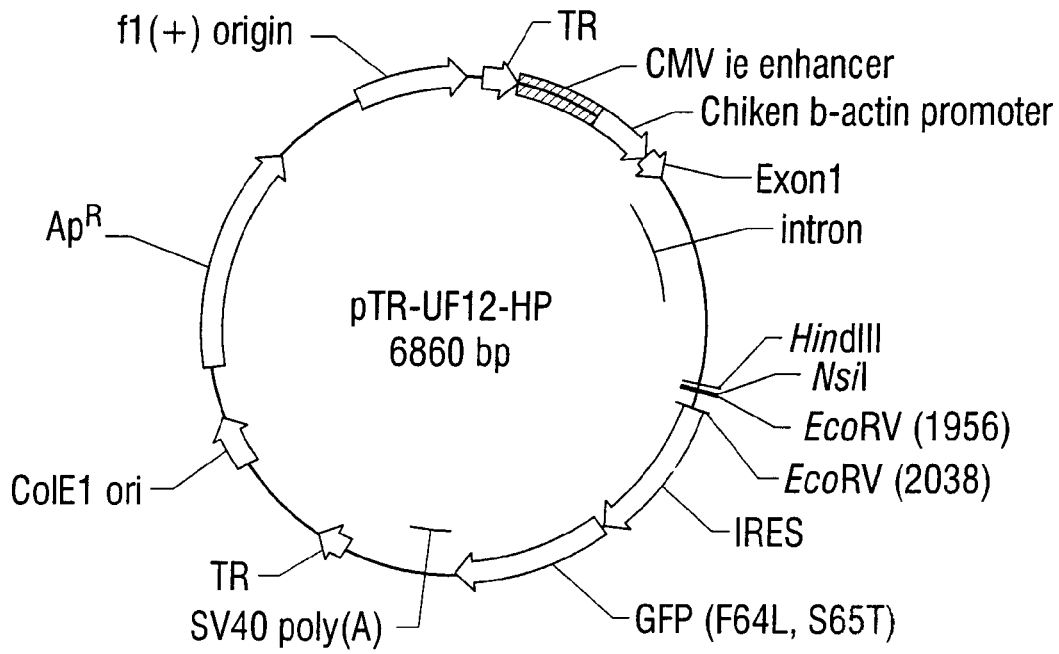
FIG. 3 shows a plasmid map of pTR-UF12-HP.
Figure 4:
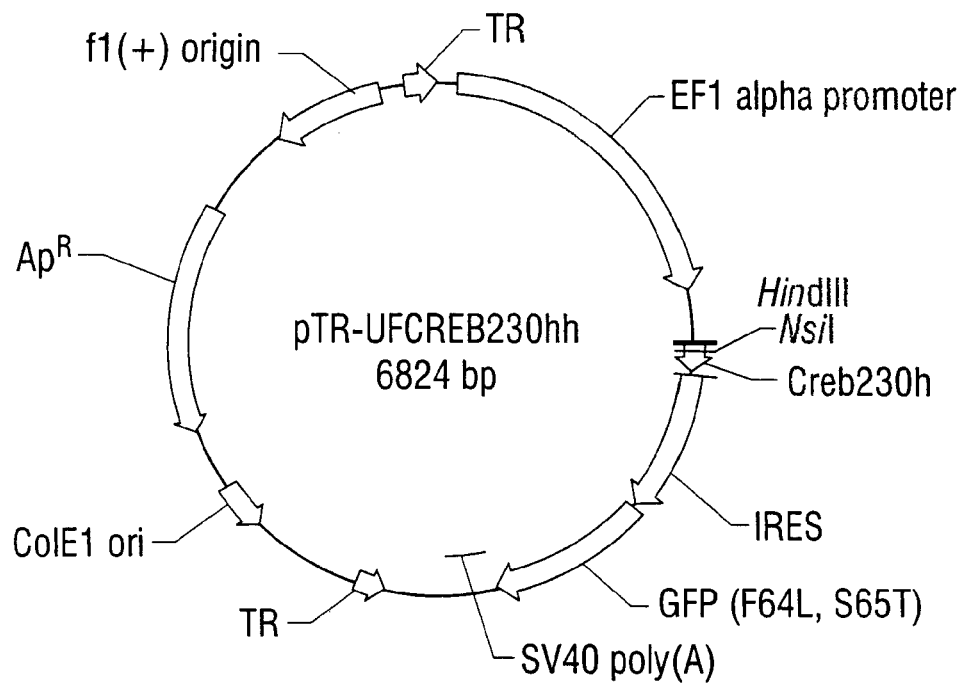
FIG. 4 shows a plasmid map of pTR-UFCREB230 hh.

A number of CREB isoforms have been characterized (Blendy et al., 1996). Three ribozymes were designed and termed CREB230 (FIG. 11), CREB 288 (FIG. 12), and CREB380 (FIG. 13) that target all isoforms of CREB. Double stranded oligonucleotides representing the sequences for these ribozymes were subcloned into the T7T3-19 expression vector (Life Biotechnologies, Gaithersburg, Md.). Ribozymes were transcribed in vitro from T7T3-19 and tested for cleavage of a CREB substrate in vitro as detailed herein above. Both CREB 230 and CREB 288 efficiently cleaved CREB RNA substrate in vitro. These ribozymes were subcloned into vector pTR-UF33*-HP (FIG. 2). As a negative control, two ribozymes containing two point mutations in the catalytic domain have been designed: CREB230m (FIG. 11) and CREB288m (FIG. 12), and have been subcloned into T7T3-19 and pTR-UF33*-HP. AAV vectors are packaged as described in Example 1 above.

Rat hippocampi are injected with AAV-expressing ribozymes using standard stereotactical procedures (Klein et al., 1998). The decrease in levels of CREB mRNA in the injected brains is determined by in situ hybridization (Simmons et al., 1989). Brains are also analyzed for a decrease in protein levels by immunocytochemistry using an anti-CREB antibody. The Morris water maze paradigm (Rozenzweig, 1996) is used to look for phenotypic differences in learning and memory between control and ribozyme injected animals.

The differential display method is used to identify novel genes involved in the consolidation of memory formation (Liang and Pardee, 1997). Normal and memory deficient animals (CREBhh) are subjected to the training paradigm. mRNA is isolated from the hippocampi of these animals at different times after training, and PCR™ amplified using a series of primer sets and run on sequencing gels to display the differential pattern of expression of mRNAs in CREBhh versus normal rats. Differentially expressed mRNAs are cloned and characterized. Searching the GenBank database identifies known genes. The differential pattern of expression is confirmed by dot blot analysis and the presence of these messages in the hippocampus is determined by RNase protection assay (Gilman et al., 1987), or by in situ hybridization (Simmons et al., 1989). Candidate genes are further evaluated for their role in learning and memory by designing candidate gene-specific ribozymes and testing them as described above for CREB.

5.5 Example 5

Candidate Genes for Retinal Disease

This example describes methods for delivering ribozymes against specific wild type (wt) alleles in a somatic retinal tissue to reduce the corresponding mRNA level sufficiently to create a "somatic knockdown" and lead to photoreceptor (PR) cell loss and a retinal disease-like phenotype. This approach permits the functional screening in animals of candidate photoreceptor-restricted ESTs (expressed sequence tags, i.e. mRNA sequences) from retina-specific libraries to identify all of the genes associated with retinal disease.

Recombinant AAV (rAAV) has been demonstrated as an efficient and nontoxic way to deliver and express genes in photoreceptor cells of the rodent retina. Proximal rod opsin promoters regulating reporter genes in rAAV were found to target expression efficiently and specifically to rod photoreceptors without pathology (Flannery et al., 1997). The duration of expression was long-term and undiminished for the life of the rat (>30 months). Additionally the number of photoreceptors expressing the transgene and the fraction of the retina transduced suggested alteration of retinal phenotypes might be possible. Indeed, rAAV delivered ribozymes against a mutant P23H rod opsin gene (Drenser et al., 1998) in transgenic rats (an animal model for autosomal dominant Retinitis Pigmentosa) preserved 30-80% of the photoreceptors that would have been lost at 8 and 3 months respectively (Lewin et al., 1998). Rescue was confirmed functionally by electroretinographic (ERG) analysis, cellularly by preservation of photoreceptor morphology and molecularly by specific reduction in mutant mRNA levels. Thus rAAV delivered ribozymes can rescue a disease phenotype in vivo.

To test whether ribozymes targeted against wild type alleles might also create photoreceptor dysfunction, Retinitis Pigmentosa (RP)-like rod degeneration was produced in rd/+mice (Bowes et al., 1990). These mice have one mutant rd allele and one wt allele of the βPDE gene and have an apparently normal retina at all ages. In the homozygous condition, the rd/rd mouse is a classical model for recessive RP, losing all rods within 1-2 months. Ribozymes designed against the wt allele were first tested in vitro and seen to digest normal βPDE mRNA well but not rd mRNA. This ribozyme was then packaged into rAAV downstream of a proximal rod opsin promoter and injected into one eye of a series of rd/+mice. At 4 months post-injection, 50%-80% fewer rod photoreceptors were found in ribozyme treated eyes relative to PBS treated contralateral control eyes. Control eyes exhibited a normal number of photoreceptors. ERG analysis in which the inventors simultaneously measured the light evoked electrical response in ribozyme treated and PBS control eyes in each animal, confirmed that a profound functional vision deficit had been created that paralleled the loss of rod cells in the treated eye. To validate this approach further, a second heterozygous mouse with a recessive mutation in a different gene (γPDE) that also exhibits an RP-like PR dysfunction in the homozygous condition was tested using rAAV-delivered ribozymes against the wt γPDE gene (FIG. 18A and FIG. 18B). Results from these studies parallel those seen with the βPDE ribozyme (FIG. 19, FIG. 20, and FIG. 21).

In vivo screening for candidate genes of unknown retinal disease significance is accomplished through the development of a differential hybridization screening strategy to identify both PR-specific genes and genes that are abundantly expressed both in PRs and in a few other tissues. The retinal cDNA library array used encompasses 40,000 cDNA clones of a normalized directionally cloned human retinal cDNA library, available for screening on high-density filters. This array is predicted to contain the majority of genes expressed in the retina at more than a few copies/cell. It has been demonstrated that the arrayed library has been effectively normalized, contains cDNAs of known retinal genes expressed over a wide range of levels, and that the cDNA inserts are long and often full-length. The array was probed with total retinal cDNA first from normal mice and then from 5-week-old rd/rd mice that lack all PRs. Retinal cDNAs detected by the wild-type probe and not by the rd/rd probe are putatively PR-specific within the retina. Of 1596 cDNAs that were screened, 144 putative PR-specific cDNAs have been identified. To date, 130 of these have been sequenced and 28 (21%) are entirely novel, 62 (46%) are known as ESTs only (including 18 previously known retina-specific ESTs), and 40 (30%) correspond to known genes. Importantly, two of the known cDNAs are rhodopsin and arrestin, well-studied photoreceptor-specific RP-causing genes, demonstrating that the strategy indeed selects genes associated with retinal disease. Eight of these human ESTs (3 expressed in the retina only, 3 of restricted expression, 2 housekeeping genes) with predicted open reading frames are associated with human retinal disease loci and have mouse EST homologues.

These sequences were the targets for validation of the results in mice. Ribozymes against each gene were designed and tested in vitro and those showing acceptable activity and specificity are then tested in vivo as outlined above. Animals may be tested at monthly intervals for impaired visual function (by ERG) and for impaired retinal morphology by optical coherence tomography (OCT) and microscopic analysis of tissue.

5.5.1 Injection of Animals

For the following animal studies pTR-UF33-HP constructs were used.

Newborn BalbC mice were injected within 24 hours of birth. The recombinant virus was administered intravenously through the temporal vein. Five groups of animals were injected according to the following groups:

A: Control (pTR-UF5)

B: rAAV carrying ribozymes against p53, p19, p16, and Rb (the retinoblastoma gene)

C: rAAV carrying the ribozyme library

D: rAAV carrying the ribozyme library+virus carrying ribozyme against p53

E: rAAV carrying the ribozyme library+virus carrying ribozymes against p19, p16, and Rb.

Each group consisted of 5 animals. A total $5 \times 10^9$ infectious units (IU) of each virus was injected per mouse. The mice were individually marked and followed by regular weight measurements (weekly). In addition they were checked upon at least twice a week for tumors or tumor-like lesions.

Likewise, in a second set of studies adult mice were injected intramuscularly into the hamstring muscles of the hindleg. The groups were the same as described above for newborn mice, except for group C that was not performed. As in the newborn mouse study, $5 \times 10^9$ IU of each virus was injected. These animals were followed the same way as the mice that were injected as newborns.

5.5.2 In Vitro Transformation Assay

In vitro transformation of cultured cells has long been used to identify genetic changes required for the formation of tumors. Several growth indicators are accepted as signs of malignant transformation. One of those signs is the loss of contact inhibition, which leads to the formation of so-called foci. Normal cells are inhibited by contact with neighboring cells, which means cultured cells growing on a petri dish stop dividing once they cover the plate with a single layer of cells (grow to 100% confluency). If, in that monolayer, a cell becomes transformed and loses contact inhibition, it will grow and form a small "pile" of cells (focus). Those foci can be detected with the naked eye. This phenomenon/sign has been employed herein for the screening of the ribozyme library in vitro.

BalbC 3T3 cells are mouse fibroblasts that are not transformed. BalbC 3T3 cells were infected at an MOI (multiplicity of infection) of 1000 with the ribozyme library in the pTR-UF21-HP virus. The cells were kept in 15-cm dishes and the medium was changed twice a week. After 4-6 weeks, the formation of foci was observed. Compared to a control plate which was infected with pTR-UF5 (an AAV construct expressing only GFP) 8-10 fold more foci in the plates treated with AAV-ribozymes than in plates treated with the control virus (spontaneous transformation, which occurs at a low rate, will give rise to foci even in the control plate).

A total of 36 foci were picked and expanded (re-grown in fresh culture medium). Genomic DNA was isolated from each focus that was grown up. The foci were screened by PCR™ the presence of a library ribozyme. Out of 28 foci that have been screened so far 8 had a clearly positive PCR™ signal. The PCR™ fragments of 3 out of the 8 PCR™ positive foci were subcloned into an E. coli plasmid (pT7T3-19). Eight or nine individual clones from each subcloned PCR product were sequenced. The results are shown in the following table:

| Focus 1-4 | 3 different ribozymes: R1-4.1 | 6/9 clones |
| | R1-4.2 | 2/9 clones |
| | R1-4.3 | 1/9 clones |
| Focus 1-11 | 2 different ribozymes: R1-11.1 | 7/8 clones |
| | R1-11.2 (identified as CREB288 ribozyme, a likely contaminant) | 1/8 clones |
| Focus 2-2 | 4 different ribozymes: R2-2.1 | 5/9 clones |
| | R2-2.2 | 1/9 clones |
| | R2-2.3 | 1/9 clones |
| | R2-2.4 | 2/9 clones |

None of the sequences matched any known tumor suppressor genes (which would serve as an internal positive control). But these sequences may identify novel genes whose function is to control cell growth or division. These genes would fall under the heading of tumor suppressor genes.

Once the screening of the foci, and the subcloning and sequencing of all the PCR™ positive foci is completed, the isolated library ribozyme may then be recloned into pTR-UF21-HP and packaged into virus. This represents an enriched sub-library that is then used in a second in vitro transformation assay. Once the libraries and sub-libraries are narrowed down to 4-6 different ribozymes, these sequences are then used to screen cDNA libraries. The ribozyme library and sub-library are then coinfected with rAAV vectors carrying the ribozymes against the known tumor suppressor genes of mice (Rb, p53, $p19^{arf}$, $p16^{ink4a}$).

5.5.3 Construction of Retinal Disease Animal Models

Once candidate disease genes have been identified through the array expression analysis methods described herein, a study may be performed to confirm retinal disease association in large animals with more human-like eyes (pigs and monkeys). AAV-vectored ribozymes will permit the preparation of new, more relevant models of retinal disease for development of appropriate therapies. In an illustrative example, analysis of the ABCR gene has been conducted. A defect in this gene is the cause of Stargardt's Disease, a central retinal defect in humans. This is currently the best-understood genetic disease of the cone-rich central retina, the macula. Macular disease is the major cause of age-related and heritable blindness in the United States, afflicting 2-5 million people. In addition to Stargardt's Disease, the principal macular diseases are Age-Related Macular Degeneration (currently the leading cause of legal blindness in the West) and the end stages of RP when macular cones degenerate after loss of most rod cells. There is currently no cure or long-term therapy. No animal model of macular disease is currently available, primarily because any such model necessarily must affect the macula, a retinal structure present only in primates.

ABCR specific ribozymes have been constructed and tested in vitro. These ribozymes and their target sequences are shown in FIG. 28, FIG. 29, FIG. 30, FIG. 31, FIG. 32, and FIG. 33. To test the hypothesis that AAV-ribozymes against the wild type ABCR gene would provide a primate model of the Stargardt's form of macular disease, the inventors designed and tested in vitro ABCR ribozymes that target both the human and monkey ABCR gene, and have delivered the AAV-ribozyme to monkey retinas. Four rhesus macaques were subretinally injected in one eye with the relevant AAV-ribozyme, and central retinal function as an indicator of Stargardt's-like disease was followed by fundus examination and ERG recordings at 4-month intervals. These results indicated the success of AAV-delivered ribozyme methods for the creation of animal primate models of macular degeneration.

5.6 Example 6

Ribozymes Targeted to Huntingtin

Due to the apparent gain of toxic function that occurs when CAG repeats are abnormally expanded in the affected gene in Huntington's disease, reduction of expression of the resultant mutant protein specifically in the neostriatum may be beneficial in this disorder. The present example describes the creation and testing of an rAAV vector to deliver an RNA cleaving molecule that will reduce the striatal expression of huntingtin. Because reduced expression of normal huntingtin is not toxic to the host, and reduced expression of mutant huntingtin is beneficial, the method provides means for treating and/or preventing accumulation of the mutant protein in an animal, and serves as a first approach to treating the disease that results from such excess.

The relatively recent establishment of transgenic animal models and cellular models utilizing human huntingtin (htt) genes with expanded CAG repeats have suggested that mutant htt induces neuropathology through a gain of abnormal function rather than a loss of normal function of the protein. The possibility that some new function of mutant htt with expanded polyglutamine (polyQ) tracts induces cellular pathology over time raises the possibility that the reduction of the transcription of mutant htt might also reduce ongoing pathological processes. Indeed, recent data showed that using an inducible system to drive expression of mutant htt, a reversal of mutant htt expression could also lead to reversal of the motor phenotype.

Recently, viral vectors that have been conclusively demonstrated to transduce large numbers of striatal neurons for long periods of time have been described. A large percentage of striatal neurons can be transduced in a dopamine deficient transgenic mouse striatum and this can rescue the phenotype for well over one year using recombinant adeno-associated viral vectors (rAAV) to deliver L-dopa. Moreover, AAV has been demonstrated to successfully deliver both ribozymes and antisense to neural tissue in order to reduce gene expression. Therefore, the possibility currently exists to try to reverse the HD-like phenotype in R6/2 transgenic mice by reducing mutant htt expression specifically in striatum via an rAAV delivered ribozyme.

5.6.1 Experimental Methods

5.6.1.1 Construction and Testing of Functional Ribozymes

Using hammerhead ribozymes, the strategy developed was to select a region in the RNA containing the triplet GUC or, in general, NUX, where N stands for any nucleotide and X is any nucleotide except guanosine (The human Huntington's disease gene has 15 GUC sites). One then creates two stretches of antisense nucleotides 6 to 8 nucleotides long and puts the 21-nucleotide sequence forming the catalytic hammerhead ribozyme between them. The principle is the same for hairpin ribozymes, except that the catalytic core is larger (34 nucleotides) and this type of ribozyme requires more specificity in the target site. Hairpins recognize the sequence NNNBNGUCNNNNNN (SEQ ID NO:67), where N is any nucleotide and B is any nucleotide but adenosine. Four functional ribozymes were tested and then packaged in an rAAV vector to test the activity of the construct in vivo. These ribozymes (shown in FIG. 22, FIG. 23, FIG. 24, and FIG. 25) cleave the IT15 mRNA. The IT15 gene encodes a protein called huntingtin and is mutated in Huntington Disease. AAV is used to deliver these ribozymes to the striatum and cortex of mice in order to determine if reducing the expression of huntingtin leads to a disease phenotype in the tissues most affected by accumulation of the mutant protein. Germ-line knockout of this gene is lethal in embryos, and AAV-delivery of ribozymes to adult animals overcomes this embryonic lethality for the reasons described herein.

5.6.1.2 In Vitro Testing on Synthetic Targets

To be effective for gene therapy, ribozymes must pass several tests in vitro. First, ribozymes are tested under standard buffer conditions (10 mM $MgCl_2$, 40 mM Tris HCl, pH 7.4) on oligonucleotide targets (13-15 nucleotides) to be sure that they are highly active and specific. Such ribonucleotide targets may be purchased from a variety of sources, including Dharmacon, Inc. (Boulder, Colo.) and deprotected according to the manufacturer's instructions. To quantify cleavage reactions, the target oligonucleotides are labeled using polynucleotide kinase and $\gamma$-$^{32}$P-ATP. At this stage, ribozymes are rejected or redesigned if they exhibit a turnover number significantly less than naturally occurring hairpin or hammerhead ribozymes (1 $min^{-1}$). Since the rate-limiting step for ribozyme reactions is the release of products, these tests are performed under target-excess, multi-turnover conditions. Ribozymes are also rejected if they cleave imperfectly matched targets (i.e. oligonucleotides with mismatches at or near the cleavage site).

To determine if a ribozyme with good kinetic properties and adequate substrate specificity is likely to cleave full-length mRNA, ribozymes are tested on transcripts of 50-80 nucleotides in length derived from the huntingtin mRNA. These sequences are cloned by PCR from a cDNA clone of huntingtin mRNA, with the target RNA molecules being generated and labeled with $^{32}$P in vitro using T7 RNA polymerase. Targets are purified by electrophoresis on acrylamide-urea gels, and renatured by heating and gradual cooling in the presence of magnesium. If the rate of cleavage of the long target appears to be significantly less (reduced by 10 fold or more) than the rate for the oligonucleotide target, then target site may not be accessible, and the candidate ribozyme may be abandoned in favor of a ribozyme recognizing an alternative target site.

Active selective ribozymes are then tested on full-length RNA transcripts derived from cloned cDNA to be certain that the target site is accessible within the folded structure of the 9.3 kb huntingtin mRNA. Ribozymes may be excluded at this stage if a significant fraction of the huntingtin RNA remains intact. Cleavage of full-length mRNA can also be detected in tissue culture, by transfecting cells that express huntingtin with plasmid vectors that encode the ribozymes to be tested driven an appropriate promoter. For this purpose, a hybrid promoter containing the enhancer elements for the immediate early promoter of cytomegalovirus (CMV) and the proximal promoter elements of the chicken gene for $\beta$-actin may be used. Reduction in the mRNA for huntingtin will be detected by RT-PCR analysis. Ribozymes that are kinetically competent and are able to cut the full-length RNA are generally useful tools for gene therapy in suppression of gene expression is desired.

5.6.1.3 Production of rAAV-Ribo-htt

To generate recombinant virus, human 293 cells are cotransfected with ribozyme-encoding rAAV plasmids and helper plasmid pDG. This plasmid contains both the AAV rep and cap genes and the adenoviral genes needed for AAV propagation. No replication competent adenovirus is detected using this method. Large-scale DNA preparations are made using Iodixanol density gradient centrifugation and affinity chromatography on heparin-agarose columns. Routine yields of virus are currently $10^{10}$-$10^{11}$ infectious particles per ml and are free of contaminating wild-type AAV.

5.6.1.4 In Vivo Testing of rAAV-ribo-htt Function rAAV-ribo-htt is injected into the right striatum in 2 locations (2 µl each site) in 24 normal 6-8 week old CBA mice. These mice are killed 4 weeks, 8 weeks and 26 weeks after vector injections (n=6 per time period). They are decapitated and their striata rapidly dissected on dry-ice. Quantitative northern blot analysis of homogenized striatum may be used to determine if there is significant reduction of htt mRNA compared to the levels measured in non-injected striatum. If the northern blot method is not sufficiently sensitive rt-PCR normalized against mouse $\beta$-actin mRNA levels may be used to determine ribozyme-induced reduction of striatal htt mRNA levels. Samples are also saved for observing reduced htt protein levels via immunoblotting. The time-points were chosen to correspond to intervals important for the behavioral studies described herein.

5.6.1.5 Testing Long-Term Intrastriatal Ribo-htt Function

Two parallel studies may be performed to characterize the effects of an anti-htt ribozyme in normal mice. Eight, 6-week-old normal CBA mice are injected intrastriatally with rAAV-ribo-htt in 2 locations in the right striatum as above. An additional 8 mice are injected identically with an rAAV-GFP control vector. These unilateral animals are tested for asymmetric rotational behavior using a series of dopamine agonists weekly beginning 4 weeks after the vector injection. Destruction of striatal function should create an asymmetry between the 2 hemispheres, which may allow detection of ribozyme-induced dysfunction in the rotational paradigm. The second study is identical to the first except that the mice receive bilateral vector injections. These mice are then tested weekly beginning 4 weeks after the vector injections on a series of tests (e.g., beam walking, rotorod, pre-pulse inhibition of the acoustic startle response, and gait analysis of foot prints). In both studies, 5/8 of the mice are killed at the end of the experiment and processed to assess htt mRNA levels as above. The remaining 3 mice/group are perfused with 4% paraformaldehyde and processed for GFP immunohistochemistry to access transgene expression.

5.7 Example 7

Ribozymes Targeted to Superoxide Dismutase

Amyotrophic lateral sclerosis (ALS) is a degenerative disease of motor neurons in the spinal cord, brainstem and cortex. (Brown, 1997) In most cases, its cause is unknown but ALS is uniformly fatal, usually within 5 years of diagnosis. About 10% of ALS cases are inherited as an autosomal dominant trait, and are collectively described as familial ALS, or FALS. Approximately 20% of FALS cases are linked to mutations in the SOD1 gene, which encodes the cytosolic enzyme Cu/Zn superoxide dismutase (Rosen et al., 1993). This 153-amino acid protein converts the toxic superoxide anion to hydrogen peroxide and molecular oxygen. More than 26 mis-sense mutations in SOD1 have been identified as leading to FALS. Three major hypotheses have been proposed for how SOD1 mutations lead to neurodegeneration (Cleveland, 1999): (i) mutant enzyme has an altered substrate affinity that leads to an accumulation of toxic products; (ii) reduced SOD activity may permit increased oxidative stress leading to damage of particularly sensitive cells; (iii) poorly or unstably folded mutant SOD protein form aggregates that are toxic specifically to motor neurons. Several animal models exist expressing mutant forms of the human SOD1 gene (Buijn et al., 1998; Shefner et al., 1999; Azzouz et al., 1997; Browne et al., 1998; Morrison et al., 1996; Ratovitski et al., 1999; Ripps et al., 1995). These do completely discriminate between the aforementioned models but suggest that accumulation of aggregates contributes to neuropathogenesis. Furthermore, at least some of the mis-sense mutants retain catalytic function, suggesting that reduced activity is not the cause of cell death. Mice devoid of SOD1 do not develop ALS, but high expression of mutant SOD1 transgenes leads to an ALS-like disease.

Several ribozymes have been designed and tested that cleave the mRNA for human SOD1 present in the mouse models of ALS (FIG. 36A, FIG. 36B, FIG. 36C, and FIG. 36D). These ribozymes cleave both the mutant and wild-type forms of SOD1 mRNA in vitro. They have been inserted in the HindIII/NsiI sites of vector pTR-UF33HP (FIG. 2). They are also being tested in conjunction with a neural-specific enolase promoter in the same vector backbone. These ribozymes so delivered should reduce the expression of mutant Cu/Zn SOD protein in motor neurons infected with these viruses. AAV constructs such as these have been used for long-term transduction of motor neurons in the spinal cord (Peel, 1997). This approach should determine whether expression of mutant SOD1 mRNA is required for damage to motor neurons in transgenic animals. These vectors should also permit identification of the relevant cell types in which expression of SOD1 mutants leads to disease. It will also determine if reducing wild-type SOD1 expression in specific cells leads to pathogenesis. These experiments may lead to a novel therapy for FALS by reducing expression of SOD1 in affected cells.

A ribozyme (SEQ ID NO:49) has been generated and tested that cleaves a sequence region (SEQ ID NO:50) of the mRNA for mouse manganese superoxide dismutase (Mn-SOD) (FIG. 27). This enzyme is protective against oxygen toxicity and protects the optic nerve in mouse models of multiple sclerosis. This ribozyme may be used to knock down expression of this gene in mice, to determine if this gene has neuroprotective function. The ribozyme is active in vitro.

5.8 Example 8

Ribozymes Targeted to NADH-Dehydrogenase Subunits

A ribozyme to the MWFE subunit of the mouse mitochondrial enzyme NADH-dehydrogenase has been constructed and tested (FIG. 26). Mitochondrial mutations affecting this same enzyme complex are associated with Leber Hereditary Optic Neuropathy. Since it has not been possible to establish a mouse model of mitochondrial disease, this AAV-ribozyme will be used to create an animal model by infecting retinal ganglion cells. The preferred vector is pTRUF12-HP (FIG. 3), which uses the CMV-β actin promoter. Ribozymes are inserted between the unique HindIII and NsiI restriction sites. This ribozyme has been tested in vitro and has been cloned into AAV.7.

6.0 REFERENCES

The following references, to the extent that they provide exemplary procedural or other details supplementary to those set forth herein, are specifically incorporated herein by reference, each in their entirety:

U.S. Pat. No. 4,683,195, issued Jul. 28, 1987.
U.S. Pat. No. 4,683,202, issued Jul. 28, 1987.
U.S. Pat. No. 4,800,159, issued Jan. 24, 1989.
U.S. Pat. No. 4,883,750, issued Nov. 28, 1989.
U.S. Pat. No. 4,987,071, issued Jan. 22, 1991.
U.S. Pat. No. 5,297,721, issued Jan. 18, 1994.
U.S. Pat. No. 5,334,711, issued Aug. 2, 1994.
U.S. Pat. No. 5,354,855, issued Oct. 11, 1994.
U.S. Pat. No. 5,455,166, issued Oct. 3, 1995.
U.S. Pat. No. 5,631,359, issued May 20, 1997.
U.S. Pat. No. 5,648,211, issued Jul. 15, 1997.
U.S. Pat. No. 5,712,124, issued Jan. 27, 1998.
U.S. Pat. No. 5,744,311, issued Apr. 28, 1998.
Int. Pat. Appl. No. PCT/US87/00880.
Int. Pat. Appl. No. PCT/US88/10315.
Int. Pat. Appl. No. PCT/US89/01025.
Int. Pat. Appl. Publ. No. WO 89/06700.
Int. Pat. Appl. Publ. No. WO 90/07641.
Int. Pat. Appl. Publ. No. WO 91/03162.
Int. Pat. Appl. Publ. No. WO 92/07065.
Int. Pat. Appl. Publ. No. WO 93/15187.
Int. Pat. Appl. Publ. No. WO 93/23569.
Int. Pat. Appl. Publ. No. WO 94/02595.
Int. Pat. Appl. Publ. No. WO 94/13688.
Eur. Pat. Appl. Publ. No. EP 0329822.
Eur. Pat. Appl. Publ. No. EP 0360257.
Eur. Pat. Appl. Publ. No. EP 320308.
Eur. Pat. Appl. Publ. No. EP 92110298.4.
Great Britian Pat. Appl. No. 2202328.
Angel, Bauman, Stein, Dellus, Rahmsdorf and Herrlich, "12-O-tetradecanoyl-phorbol-13-acetate induction of the human collagenase gene is mediated by an inducible enhancer element located in the 5' flanking region," *Mol. Cell. Biol.*, 7:2256, 1987a.
Angel, Imagawa, Chiu, Stein, Imbra, Rahmsdorf, Jonat, Herrlich and Karin, "Phorbol ester-inducible genes contain a common cis element recognized by a TPA-modulated trans-acting factor," *Cell*, 49:729, 1987b.
Atchison and Perry, "Tandem kappa immunoglobulin promoters are equally active in the presence of the kappa enhancer: Implications for model of enhancer function," *Cell*, 46:253, 1986.

Atchison and Perry, "The role of the kappa enhancer and its binding factor NF-kappa B in the developmental regulation of kappa gene transcription," *Cell*, 48:121, 1987.

Azzouz, Leclerc, Gurney, Warter, Poindron, and Borg, "Progressive motor neuron impairment in an animal model of familial amyotrophic lateral sclerosis," *Muscle Nerve*, 20:45-51, 1997.

Baker, "GCR1 of *Saccharomyces cerevisiae* encodes a DNA binding protein whose binding is abolished by mutations in the CTTCC sequence motif," *Proc. Nat'l Acad. Sci. USA*, 88:9443-9447, 1991.

Banerji, Olson and Schaffner, "A lymphocyte-specific cellular enhancer is located downstream of the joining region in immunoglobulin heavy-chain genes," *Cell*, 35:729, 1983.

Banerji, Rusconi and Schaffner, "Expression of a beta-globin gene is enhanced by remote SV40 DNA sequences," *Cell*, 27:299, 1981.

Bartlett et al., "Long-term expression of a fluorescent reporter gene via direct injection of plasmid vector into mouse skeletal muscle: Comparison of human creatine kinase and CMV promoter expression levels in vivo," *Cell Transplant.*, 5(3):411-419, 1996.

Bennett et al., "Adenovirus-mediated delivery of rhodopsin-promeoted bcl-2 results in a delay in photoreceptor cell death in the rd/rd mouse," *Gene Ther.*, 5(9):1156-1164, 1998.

Bennett, Duan, Engelhardt and Maguire, "Real-time, non-invasive in vivo assessment of adeno-associated virus-mediated retinal transduction," *Invest. Ophthalmol. Vis. Sci.*, 38:2857-2863, 1997.

Berkhout, Silverman and Jeang, "tat trans-activates the human immunodeficiency virus through a nascent RNA target," *Cell*, 59:273, 1989.

Birikh, Heaton and Eckstein, "The structure, function and application of the hammerhead ribozyme," *Eur. J. Biochem.*, 245:1-16, 1997.

Blanar, Baldwin, Flavell and Sharp, "A gamma-interferon-induced factor that binds the interferon response sequence of the MHC Class I gene, H-2 Kb," *EMBO J.*, 8:1139, 1989.

Blendy et al., "Targeting of the CREB gene leads to up-regulation of a novel CREB mRNA isoform," *EMBO J.*, 15:1098-1106, 1996.

Bodine and Ley, "An enhancer element lies 3' to the Human A gamma globin gene," *EMBO J.*, 6:2997, 1987.

Boshart, Weber, Jahn, Dorsch-Hasler, Fleckenstein and Schaffner, "A very strong enhancer is located upstream of an immediate early gene of human cytomegalovirus," *Cell*, 41:521, 1985.

Bosze, Thiesen and Charnay, "A transcriptional enhancer with specificity for erythroid cells is located in the long terminal repeat of the friend murine leukemia virus," *EMBO J.*, 5:1615, 1986.

Bowes, Li, Danciger, Baxter, Applebury and Farber, "Retinal degeneration in the rd mouse is caused by a defect in the β subunit of rod cGMP-phosphodiesterase," *Nature*, 347: 677-680, 1990.

Braddock, Chambers, Wilson, Esnouf, Adams, Kingsman and Kingsman, "HIV-I tat activates presynthesized RNA in the nucleus," *Cell*, 58: 269, 1989.

Brown, "Amylotrophic lateral sclerosis. Insights from genetics," *Arch. Neurol.*, 54 (10): 1246-1250, 1997.

Browne, Bowling, Baik, Gurney, Brown, and Beal, "Metabolic dysfunction in familial, but not sporadic, amyotrophic lateral sclerosis," *J. Neurochem.* 71: 281-287, 1998.

Buijn et al., *Science*, 281: 1851-1853, 1998.

Bulla and Siddiqui, "The Hepatitis B virus enhancer modulates transcription of the Hepatitis B virus surface-antigen gene from an internal location," *J. Virol.*, 62: 1437, 1986.

Campbell and Villarreal, "Functional analysis of the individual enhancer core sequences of polyoma virus: cell-specific uncoupling of DNA replication from transcription," *Mol. Cell. Biol.*, 8: 1993, 1988.

Campere and Tilghman, "Postnatal repression of the α-fetoprotein gene is enhancer independent," *Genes and Dev.*, 3: 537, 1989.

Campo, Spandidos, Lang and Wilkie, "Transcriptional control signals in the genome of bovine papilloma virus Type 1," *Nature*, 303: 77, 1983.

Cech et al., "In vitro splicing of the ribosomal RNA precursor of *Tetrahymena*: Involvement of a guanosine nucleotide in the excision of the intervening sequence," *Cell*, 27 (3 Pt 2): 487-496, 1981.

Celander and Haseltine, "Glucocorticoid regulation of murine leukemia virus transcription elements is specified by determinants within the viral enhancer region," *J. Virology*, 61: 269, 1987.

Celander, Hsu and Haseltine, "Regulatory elements within the murine leukemia virus enhancer regions mediate glucocorticoid responsiveness," *J. Virology*, 62: 1314, 1988.

Chambers, Stanway, Kingsman and Kingsman, "The UAS of the yeast PGK gene is composed of multiple functional elements," *Nucleic Acids Res.*, 16: 8245-8260, 1988.

Chandler, Maler and Yamamoto, "DNA sequences bound specifically by glucocorticoid receptor in vitro render a heterlogous promoter hormone responsive in vivo," *Cell*, 33: 489, 1983.

Chang, Erwin and Lee, "Glucose-regulated protein (GRP94 and GRP78) genes share common regulatory domains and are coordinately regulated by common trans-acting factors," *Mol. Cell. Biol.*, 9: 2153, 1989.

Chang, Hao and Wong, "Apoptosis: Final common pathway of photoreceptor death in rd, rds and rhodopsin mutant mice," *Neuron*, 11: 595-605, 1993.

Chatterjee, Lee, Rentoumis and Jameson, "Negative regulation of the thyroid-stimulating hormone alpha gene by thyroid hormone: Receptor interaction adjacent to the TATA box," *Proc. Natl. Acad. Sci. U.S.A.*, 86: 9114, 1989.

Chee, Yang, Hubbell, et al., "Accessing genetic information with high-density DNA arrays," *Science*, 274: 610-614, 1996.

Chen et al., "Multitarget-ribozyme directed to cleave at up to nine highly conserved HIV-1 env RNA regions inhibits HIV-1 replication—potential effectiveness against most presently sequenced HIV-1 isolates," *Nucl. Acids Res.*, 20: 4581-4589, 1992.

Choi, Chen, Kriegler and Roninson, "An altered pattern of cross-resistance in multi-drug-resistant human cells results from spontaneous mutations in the MDR-1 (P-glycoprotein) gene," *Cell*, 53: 519, 1988.

Chowrira and Burke, "Extensive phosphorothioate substitution yields highly active and nuclease-resistant hairpin ribozymes," *Nucl. Acids Res.*, 20: 2835-2840, 1992.

Clark, Sferra and Johnson, "Recombinant adeno-associated viral vectors mediate long-term transgene expression in muscle," *Hum. Gene Ther.*, 8: 659-669, 1997. Cleveland, *Neuron*, 23: 515-520, 1999.

Clifton and Fraenkel, "The gcr (glycolysis regulation) mutation of *Saccharomyces cerevisiae*," *J. Biol. Chem.*, 256: 13074-13078, 1981.

Cohen, Walter and Levinson, "A repetitive sequence element 3' of the human c-Ha-ras1 gene has enhancer activity," *J. Cell. Physiol.*, 5: 75, 1987.

Collins and Olive, "Reaction conditions and kinetics of self-cleavage of a ribozyme derived from Neurospora VS RNA," *Biochem.*, 32 (11): 2795-2799, 1993.

Collins, Jacks and Pavletich, "The cell cycle and cancer," *Proc. Natl. Acad. Sci. USA*, 94: 2776-2778, 1997.

Costa, Lai, Grayson and Darnell, "The cell-specific enhancer of the mouse transthyretin (prealbumin) gene binds a common factor at one site and a liver-specific factor(s) at two other sites," *Mol. Cell. Biol.*, 8: 81, 1988.

Cripe, Haugen, Turk, Tabatabai, Schmid, Durst, Gissmann, Roman and Turek, "Transcriptional regulation of the human papilloma virus-16 E6-E7 promoter by a keratinocyte-dependent enhancer, and by viral E2 trans-activator and repressor gene products: Implications for cervical carcinogenesis," *EMBO J.*, 6: 3745, 1987.

Culotta and Hamer, "Fine mapping of a mouse metallothionein gene metal-response element," *Mol. Cell. Biol.*, 9: 1376, 1989.

Daiger, Rossiter, Greenberg, Christoffels and Hide, "Data services and software for identifying genes and mutations causing retinal degeneration," *Invest. Ophthalmol. Vis. Sci.*, 39: S295, 1998.

Dandolo, Blangy and Kamen, "Regulation of polyma virus transcription in murine embryonal carcinoma cells," *J. Virology*, 47: 55, 1983.

De Villiers, Schaffner, Tyndall, Lupton and Kamen, "Polyoma virus DNA replication requires an enhancer," *Nature*, 312: 242, 1984.

DeRisi, Iyer and Brown, "Exploring the metabolic and genetic control of gene expression on a genomic scale," *Science*, 278: 680-86, 1997.

Deschamps, Meijlink and Verma, "Identification of a transcriptional enhancer element upstream from the proto-oncogene Fos," *Science*, 230: 1174, 1985.

Donehower et al., "Mice deficient for p53 are developmentally normal but susceptible to spontanous tumors," *Nature*, 356: 215-221, 1992.

Drenser, Timmers, Hauswirth and Lewin, "Ribozyme-targeted destruction of RNAs associated with ADRP," *Inv. Ophth. Vis. Sci.*, 39: 681-689, 1998.

Dropulic, Lin, Martin, Jeang, "Functional characterization of a U5 ribozyme: intracellular suppression of human immunodeficiency virus type 1 expression," *J. Virol.*, 66 (3): 1432-1441, 1992.

Dryja and Berso, "Retinitis pigmentosa and allied diseases. Implications of genetic heterogeneity," *Invest. Ophthalmol. Vis. Sci.*, 36: 1197-1200, 1995.

Dudley, Gansheroff and Winston, "Specific components of the SAGA complex are required for," *Genetics*, 151: 1365-1378, 1999.

During et al., "Peroral gene therapy of lactose intolerance using an adeno-associated virus vector," *Nature Med.*, 4: 1131-1135, 1998.

Edbrooke, Burt, Cheshire and Woo, "Identification of cis-acting sequences responsible for phorbol ester induction of human serum amyloid a gene expression via a nuclear-factor-κB-like transcription factor," *Mol. Cell. Biol.*, 9: 1908, 1989.

Edlund, Walker, Barr and Rutter, "Cell-specific expression of the rat insulin gene: Evidence for role of two distinct 5' flanking elements," *Science*, 230: 912, 1985.

Eisen, Spellman, Brown and Botstein, "Cluster analysis and display of genome-wide expression patterns," *Proc. Nat'l Acad. Sci. USA*, 95: 14863-14868, 1998.

Elroy-Stein and Moss, "Cytoplasmic expression system based on constitutive synthesis of bacteriophage T7 RNA polymerase in mammalian cells," *Proc. Natl. Acad. Sci. USA*, 87: 6743-6747, 1990.

Faktorovich, Steinberg, Yasumura, Matthes and LaVail, "Photoreceptor degeneration in inherited dystrophy delayed by the basic fibroblast growth factor," *Nature*, 347: 83-86, 1990.

Fedor and Uhlenbeck, "Substrate sequence effects on 'hammerhead' RNA catalytic efficiency," *Proc. Nat'l Acad. Sci. USA*, 87: 1668-1672, 1990.

Feng and Holland, "HIV-I tat trans-activation requires the loop sequence within tar," *Nature*, 334: 6178, 1988.

Firak and Subramanian, "Minimal transcription enhancer of simian virus 40 is a 74-base-pair sequence that has interacting domains," *Mol. Cell. Biol.*, 6: 3667, 1986.

Fisher et al., "Recombinant adeno-associated virus for muscle directed gene therapy," *Nature Med.*, 3: 306-312, 1997.

Flannery, Bowes and Farber, "The rd mouse story, seventy years of research on an animal model of inherited retinal degeneration," In: *Progress in retinal research*, (Chader and Osborne, eds.), Amsterdam: Elsevier North-Holland, 1994.

Flannery, Zolotukhin, Vaquero, LaVail, Muzyczka and Hauswirth, "Efficient photoreceptor-targeted gene expression in vivo by recombinant adeno-associated virus," *Proc. Natl. Acad. Sci. USA*, 94: 6916-6921, 1997.

Flotte, "Stable in vivo expression of the cystic fibrosis transmembrane conductance regulator with an adeno-associated virus vector," *Proc. Natl. Acad. Sci. USA*, 90: 10613-10617, 1993.

Flotte, Carter, Conrad, et al., "Clinical protocol: A phase I trial of an adeno associated virus-CFTR gene vector in adult CF patients with mild lung disease," *Human Gene Therapy*, 7: 1145-1159, 1996.

Forster and Symons, "Self-cleavage of plus and minus RNAs of a virusoid and a structural model for the active sites," *Cell*, 49: 211-220, 1987.

Frohman, In: *PCR Protocols: A Guide To Methods And Applications*, Academic Press, New York, 1990.

Fujita, Shibuya, Hotta, Yamanishi and Taniguchi, "Interferon-beta gene regulation: tandemly repeated sequences of a synthetic 6-bp oligomer function as a virus-inducible enhancer," *Cell*, 49: 357, 1987.

Gao and Huang, "Cytoplasmic expression of a reporter gene by co-delivery of T7 RNA polymerase and T7 promoter sequence with cationic liposomes," *Nucl. Acids Res.*, 21: 2867-2872, 1993.

Gerlach et al., "Construction of a plant disease resistance gene from the satellite RNA of tobacco rinspot virus," *Nature*, 328: 802-805, 1987.

Gilles, Morris, Oi and Tonegawa, "A tissue-specific transcription enhancer element is lcoated in the major intron of a rearranged immunoglobulin heavy-chain gene," *Cell*, 33: 717, 1983.

Gilman, In: *Current Protocols in Molecular Biology*, Ausubel et al., Eds., John Wiley & Sons, New York, pp. 4.7.1-4.7.8, 1987.

Gloss, Bernard, Seedorf and Klock, "The upstream regulatory region of the human papilloma virus-16 contains an E2 protein-independent enhancer which is specific for cervical carcinoma cells and regulated by glucocorticoid hormones," *EMBO J.*, 6: 3735, 1987.

Godbout, Ingram and Tilghman, "Fine-structure mapping of the three mouse alpha-fetoprotein gene enhancers," *Mol. Cell. Biol.*, 8: 1169, 1988.

Golub, Slonim, Tamayo, et al., "Molecular classification of cancer: class discovery and class prediction by gene expression monitoring," *Science,* 286: 531-537, 1999.

Gonzalez et al., "A cluster of phosphorylation sites on the cyclic AMP-regulated nuclear factor CREB predicted by its sequence," *Nature,* 337: 749-752, 1989.

Goodbourn and Maniatis, "Overlapping positive and negative regulatory domains of the human β-interferon gene," *Proc. Natl. Acad. Sci. USA,* 85: 1447, 1988.

Goodbourn, Burstein and Maniatis, "The human beta-interferon gene enhancer is under negative control," *Cell,* 45: 601, 1986.

Greene, Böhnlein and Ballard, "HIV-1, and normal T-cell growth: Transcriptional strategies and surprises," *Immunology Today,* 10: 272, 1989.

Grimm, Kern, Rittner and Kleinschmidt, "Novel tools for production and purification of recombinant AAV vectors," *Hum. Gene Ther.,* 9: 2745-2760, 1998.

Grosschedl and Baltimore, "Cell-type specificity of immunoglobulin gene expression is regulated by at least three DNA sequence elements," *Cell,* 41: 885, 1985.

Guerrier-Takada, Gardiner, Marsh, pace, Altman, "The RNA moiety of ribonuclease P is the catalytic subunit of the enzyme," *Cell,* 35: 849, 1983.

Guy, Qi and Hauswirth, "Adeno-associated viral-mediated catalase expression suppresses optic neuritis in experimental allergic encephalomyelitis," *Proc. Nat'l Acad. Sci. USA,* 95: 13847-13852, 1998.

Guy, Qi, Muzyczka and Hauswirth, "Reporter expression persists 1 year after adeno-associated virus-mediated gene transfer to the optic nerve," *Arch. Ophthalmol.,* 117: 929-937, 1999.

Guzowski et al., "Antisense oligodeoxynucleotide-mediated disruption of hippocampal cAMP response element binding protein levels impairs consolidation of memory for water maze training," *Proc. Natl. Acad. Sci. USA,* 94: 2693-2698, 1997.

Hampel and Tritz, "RNA catalytic properties of the minimum (-)s TRSV sequence," *Biochem.,* 28: 4929, 1989.

Hampel, Tritz, Hicks, Cruz, "'Hairpin' catalytic RNA model: evidence for helices and sequence requirement for substrate RNA," *Nucl. Acids Res.,* 18: 299, 1990.

Harvey, Vogel, Lee, Bradley and Donehower, "Mice Deficient in p53 and Rb develop tumors primarily of endocrine origin," *Cancer Res.,* 55: 1146-1151, 1995.

Haslinger and Karin, "Upstream promoter element of the human metallothionein-II gene can act like an enhancer element," *Proc. Natl. Acad. Sci. U.S.A.,* 82: 8572, 1985.

Hauber and Cullen, "Mutational analysis of the trans-activiation-responsive region of the human immunodeficiency virus Type I long terminal repeat," *J. Virology,* 62: 673, 1988.

Hauswirth, Lewin, Zolotukhin and Muzyczka, "Production and purification of recombinant AAV vectors," In: *Vertebrate Phototransduction and the Visual Cycle. Methods in Enzymology* 316, (Palczewski (ed.)), New York, Academic Press, in press, 2000.

Hawes, Smith, Chang, et al., "Mouse fundus photography and angiography: a catalogue of normal and mutant phenotypes," *Mol. Vis.,* 5: 22, 1999.

Hen, Borrelli, Fromental, Sassone-Corsi and Chambon, "A mutated polyoma virus enhancer which is active in undifferentiated embryonal carcinoma cells is not repressed by adenovirus-2 E1A products," *Nature,* 321: 249, 1986.

Hensel, Meichle, Pfizenmaier and Kronke, "PMA-responsive 5' flanking sequences of the human TNF gene," *Lymphokine Res.,* 8: 347, 1989.

Hermonat and Muzyczka, "Use of adenoassociated virus as a mammalian DNA cloning vector: Transduction of neomycin resistance into mammalian tissue culture cells," *Proc. Natl. Acad. Sci. USA,* 81: 6466-6470, 1984.

Hernandez, Wang, Kearns, et al., "Latent adeno-associated virus infection elicits humoral but not cell-mediated immune responses in a nonhuman primate model," *J. Virol.* 73: 8549-8558, 1999.

Herr and Clarke, "The SV40 enhancer is composed of multiple functional elements that can compensate for one another," *Cell,* 45: 461, 1986.

Herruer, Mager, Woudt, et al., "Transcriptional control of yeast ribosomal protein synthesis during carbon-source upshift," *Nucleic Acids Res.,* 15: 10133-10144, 1987.

Hertel, Herschlag and Uhlenbeck, "A kinetic and thermodynamic framework for the hammerhead ribozyme reaction," *Biochemistry,* 33: 3374-3385, 1994.

Herzog, Hagstrom, Kung, Tai, Wilson, Fisher and High, "Stable gene transfer and expression of human blood coagulation factor IX after intramuscular injection of recombinant adeno-associated virus," *Proc. Natl. Acad. Sci. USA,* 94: 5804-5809, 1997.

Hirochika, Browker and Chow, "Enhancers and trans-acting E2 transcriptional factors of papilloma viruses," *J. Virol.,* 61: 2599, 1987.

Hirsch, Gaugler, Deagostini-Bauzin, Bally-Cuif and Gordis, "Identification of positive and negative regulatory elements governing cell-type-specific expression of the neural-cell-adhesion-molecule gene," *Mol. Cell. Biol.,* 10: 1959, 1990.

Holbrook, Gulino and Ruscetti, "cis-acting transcriptional regulatory sequences in the Gibbon ape leukemia virus (GALV) long terminal repeat," *Virology,* 157: 211, 1987.

Hoover et al., Eds., In: *Remington's Pharmaceutical Sciences,* 16th Edition, Mack Publishing Co., Easton, Pa., 1980.

Horlick and Benfield, "The upstream muscle-specific enhancer of the rat muscle creatine kinase gene is composed of multiple elements," *Mol. Cell. Biol.,* 9: 2396, 1989.

Huang, Ostrowski, Berard and Hagar, "Glucocorticoid regulation of the Ha-MuSV p21 gene conferred by sequences from mouse mammary tumor virus," *Cell,* 27: 245, 1981.

Huie, Scott, Drazinic, et al., "Characterization of the DNA-binding activity of GCR1: in vivo evidence for two GCR1-binding sites in the upstream activating sequence of TPI of *Saccharomyces cerevisiae,*" *Mol. Cell Biol.,* 12: 2690-2700, 1992.

Hwang, Lim and Chae, "Characterization of the s-phase-specific transcription regulatory elements in a DNA-replication-independent testis-specific H2B (TH2B) histone gene," *Mol. Cell. Biol.,* 10: 585, 1990.

Imagawa, Chiu and Karin, "Transcription factor AP-2 mediates induction by two different signal-transduction pathways: Protein kinase C and cAMP," *Cell,* 51: 251, 1987.

Imbra and Karin, "Phorbol ester induces the transcriptional stimulatory activity of the SV40 enhancer," *Nature,* 323: 555, 1986.

Imler, Lemaire, Wasvlyk and Waslyk, "Negative regulation contributes to tissue specificity of the immunoglobulin heavy-chain enhancer," *Mol. Cell. Biol.,* 7: 2558, 1987.

Imperiale and Nevins, "Adenovirus 5 E2 transcription unit: An E1A-inducible promoter with an essential element that functions independently of position or orientation," *Mol. Cell. Biol.,* 4: 875, 1984.

Iyer, Eisen, Ross, et al., "The transcriptional program in the response of human fibroblasts to serum," *Science*, 283: 83-87, 1999.

Jacks, Remington, Williams, Schmitt, Halachmi, Bronson and Weinberg, "Tumor spectrum analysis in p53-mutant mice," *Curr. Biol.*, 4: 1-7, 1994.

Jacobson, Cideciyan, Huang, Hanna, Freund, Affatigato, Carr, Zack, Stone and McInnes, "Retinal degenerations with truncation mutations in the cone-rod homeobox (CRX) gene," *Invest. Ophthalmol. Vis. Sci.*, 39: 2417-2426, 1998.

Jaeger, Turner, Zuker, "Improved predictions of secondary structures for RNA," *Proc. Natl. Acad. Sci. USA*, 86 (20): 7706-7710, 1989.

Jakobovits, Smith, Jakobovits and Capon, "A discrete element 3' of human immunodeficiency virus 1 (HIV-1) and HIV-2 mRNA initiation sites mediates transcriptional activation by an HIV trans-activator," *Mol. Cell. Biol.*, 8: 2555, 1988.

Jameel and Siddiqui, "The human Hepatitis B virus enhancer requires transacting cellular factor(s) for activity," *Mol. Cell. Biol.*, 6: 710, 1986.

Jaynes, Johnson, Buskin, Gartside and Hauschka, "The muscle creatine kinase gene is regulated by multiple upstream elements, including a muscle-specific enhancer," *Mol. Cell. Biol.*, 8: 62, 1988.

Johnson, Wold and Hauschka, "Muscle creatine kinase sequence elements regulating skeletal and cardiac muscle expression in transgenic mice," *Mol. Cell. Biol.*, 9: 3393, 1989a.

Joyce, "RNA evolution and the origins of life," *Nature*, 338: 217-244, 1989.

Kadesch and Berg, "Effects of the position of the simian virus 40 enhancer on expression of multiple transcription units in a single plasmid," *Mol. Cell. Biol.*, 6: 2593, 1986.

Kaplitt, Leone, Samulski, et al., "Long-term gene expression and phenotypic correction using adeno-associated virus vectors in the mammalian brain," *Nat. Genet.*, 8: 148-54, 1994.

Karin, Haslinger, Heguy, Dietlin and Cooke, "Metal-responsive elements act as positive modulators of human metallothionein-IIa enhancer activity," *Mol. Cell. Biol.*, 7: 606, 1987.

Kashani-Sabet et al., "Reversal of the malignant phenotype by an anti-ras ribozyme," *Antisense Res. Dev.*, 2: 3-15, 1992.

Katinka, Vasseur, Montreau, Yaniv and Blangy, "Polyoma DNA sequences involved in the control of viral gene expression in murine embryonal carcinoma cells," *Nature*, 290: 720, 1981.

Katinka, Yaniv, Vasseur and Blangy, "Expression of polyoma early functions in mouse embryonal carcinoma cells depends on sequence rearrangements in the beginning of the late region," *Cell*, 20: 393, 1980.

Kawamoto, Makino, Niw, Sugiyama, Kimura, Anemura, Nakata and Kakunaga, "Identification of the human beta-actin enhancer and its binding factor," *Mol. Cell. Biol.*, 8: 267, 1988.

Kay, Manno, Ragni, et al., "Evidence for gene transfer and expression of factor IX in haemophilia B patients treated with an AAV vector," *Nat. Genet.*, 24: 257-261, 2000.

Kearns, Afione, Fulmer, et al., "Recombinant adeno-associated virus (AAV-CFTR) vectors do not integrate in a site-specific fashion in an immortalized epithelial cell line," *Gene Ther.*, 3: 748-755, 1996.

Kessler, Podsakoff, Chen, et al., "Gene delivery to skeletal muscle results in sustained expression and systematic delivery of a therapeutic protein," *PNAS*, 93: 14082-14087, 1996.

Kief and Warner, "Coordinate control of syntheses of ribosomal ribonucleic acid and ribosomal proteins during nutritional shift-up in *Saccharomyces cerevisiae*," *Mol. Cell Biol.*, 1: 1007-1015, 1981.

Kiledjian, Su and Kadesch, "Identification and characterization of two functional domains within the murine heavy-chain enhancer," *Mol. Cell. Biol.*, 8: 145, 1988.

Kim and Cech, "Three-dimensional model of the active site of the self-splicing rRNA precursor of Tetrahymena," *Proc. Natl. Acad. Sci. USA*, 84: 8788-8792, 1987.

Kim et al., "Use of the human elongation factor 1 alpha promoter as a versatile and efficient expression system," *Gene*, 91: 217-223, 1990.

Klamut, Gangopadyhay, Worton and Ray, "Molecular and functional analysis of the muscle-specific promoter region of the Duchenne muscular dystrophy gene," *Mol. Cell. Biol.*, 10: 193, 1990.

Klein et al., "Neuron-specific transduction in the rat septo-hippocampal or nigrostriatal pathway by recombinant adeno-associated virus vectors," *Exp. Neurol.*, 150 (2): 183-194, 1998.

Knudson, "Antioncogenes and human cancer," *Proc. Natl. Acad. Sci. USA*, 90: 10914-10921, 1993.

Koch, Benoist and Mathis, "Anatomy of a new B-cell-specific enhancer," *Mol. Cell. Biol.*, 9: 303, 1989.

Koeberl, Alexander, Halbert, et al., "Persistent expression of human clotting factor IX from mouse yliver after intravenous injection of adeno-associated virus vectors," *Proc. Nat'l Acad. Sci. USA*, 94: 1426-1431, 1997.

Kotin et al., "Site-specific integration by adeno-associated virus," *Proc. Natl. Acad. Sci. USA*, 87: 2211-2215, 1990.

Kraakman, Griffioen, Zerp, et al., "Growth-related expression of ribosomal protein genes in *Saccharomyces cerevisiae*," *Mol. Gen. Genet.*, 239: 196-204, 1993.

Kriegler and Botchan, "A retrovirus LTR contains a new type of eukaryotic regulatory element," In: *Eukaryotic Viral Vectors*, Gluzman, Ed., Cold Spring Harbor, Cold Spring Harbor Laboratory, N.Y., 1982.

Kriegler and Botchan, "Enhanced transformation by a simian virus 40 recombinant virus containing a Harvey murine sarcoma virus long terminal repeat," *Mol. Cell. Biol.* 3: 325, 1983.

Kriegler, Perez and Botchan, "Promoter substitution and enhancer augmentation increases the penetrance of the SV40 a gene to levels comparable to that of the Harvey murine sarcoma virus Ras gene in morphologic transformation," In: *Gene Expression*, Hamer and Rosenberg, Eds., New York, Alan R. Liss, 1983.

Kriegler, Perez, Defay, Albert and Liu, "A novel form of TNF/cachectin is a cell-surface cytotoxix transmembrane protein: Ramifications for the complex physiology of TNF," *Cell*, 53: 45, 1988.

Kriegler, Perez, Hardy and Botchan, "Transformation mediated by the SV40 T antigens: separation of the overlapping SV40 early genes with a retroviral vector," *Cell*, 38: 483, 1984a.

Kriegler, Perez, Hardy and Botchan, "Viral integration and early gene expression both affect the efficiency of SV40 transformation of murine cells: Biochemical and biological characterization of an SV40 retrovirus," In: *Cancer Cells 2/Oncogenes and Viral Genes*, Van de Woude, Levine, Topp and Watson, Eds., Cold Spring Harbor, Cold Spring Harbor Laboratory, 1984b.

Kuhl, De La Fuenta, Chaturvedi, Parinool, Ryals, Meyer and Weissman, "Reversible silencing of enhancers by sequences derived from the human IFN-alpha promoter," *Cell*, 50: 1057, 1987.

Kumar-Singh and Farber, "Encapsidated adenovirus mini-chromosome-mediated delivery of genes to the retina: application to the rescue of photoreceptor degeneration," *Hum. Mol. Genet.*, 7: 1893-900, 1998.

Kunz, Zimmerman, Heisig and Heinrich, "Identification of the promoter sequences involved in the Interleukin-6-dependent expression of the rat alpha-2-macroglobulin gene," *Nucl. Acids Res.*, 17: 1121, 1989.

Larsen, Harney and Moore, "Repression medaites cell-type-specific expression of the rat growth hormone gene," *Proc. Natl. Acad. Sci. U.S.A.*, 83: 8283, 1986.

Laspia, Rice and Mathews, "HIV-1 tat protein increases transcriptional initiation and stabilizes elongation," *Cell*, 59: 283, 1989.

Latimer, Berger and Baumann, "Highly conserved upstream regions of the $\alpha_1$-antitrypsin gene in two mouse species govern liver-specific expression by different mechanisms," *Mol. Cell. Biol.*, 10: 760, 1990.

Lee et al., "Functional analysis of the steroid hormone control region of mouse mammary tumor virus," *Nucleic Acids Res.*, 12 (10): 4191-4206, 1984.

Lee, Mulligan, Berg and Ringold, "Glucocorticoids regulate expression of dihydrofolate reductase cDNA in mouse mammary tumor virus chimaeric plasmids," *Nature*, 294: 228, 1981.

Lem, Flannery, Li, et al., "Retinal degeneration is rescued in transgenic rd mice by expression of the cGMP phosphodiesterase beta subunit," *Proc. Nat'l Acad. Sci. USA*, 89: 4422-4426, 1992.

Levinson, Khoury, VanDeWoude and Gruss, "Activation of SV40 genome by 72-base-pair tandem repeats of Moloney sarcoma virus," *Nature*, 295: 79, 1982.

Lewin, Drenser, Hauswirth, Nishikawa, Yasumura, Flannery and LaVail, "Ribozyme rescue of photoreceptor cells in a transgenic rat model of autosomal dominant retinitis pigmentosa," *Nat. Med.*, 4: 967-971, 1998.

L'Huillier, David, Bellamy, "Cytoplasmic delivery of ribozymes leads to efficient reduction in alpha-lactalbumin mRNA levels in C1271 mouse cells," *EMBO J.*, 11 (12): 4411-4418, 1992.

Liang and Pardee, "Differential display. A general protocol," *Methods Mol. Biol.*, 85: 3-11, 1997.

Lieber, Sandig, Sommer, Bahring, Strauss, "Stable high-level gene expression in mammalian cells by T7 phage RNA polymerase," *Methods Enzymol.*, 217: 47-66, 1993.

Lin, Cross, Halden, Dragos, Toledano and Leonard, "Delineation of an enhancer like positive regulatory element in the interleukin-2 receptor $\alpha$-chain gene," *Mol. Cell. Biol.*, 10: 850, 1990.

Linden and Woo, "AAVant-garde gene therapy," *Nat. Med.*, 5: 21-22, 1999.

Lisziewicz et al., "Inhibition of human immunodeficiency virus type 1 replication by regulated expression of a polymeric Tat activation response RNA decoy as a strategy for gene therapy in AIDS," *Proc. Natl. Acad. Sci. USA*, 90: 8000-8004, 1993.

Lockhart, Dong, Byrne, et al., "Expression monitoring by hybridization to high-density oligonucleotide arrays," *Nat. Biotechnol.*, 14: 1675-1680, 1996.

Luria, Gross, Horowitz and Givol, "Promoter ehancer elements in the rearranged alpha-chain gene of the human T-cell receptor," *EMBO J.*, 6: 3307, 1987.

Lusky and Botchan, "Transient replication of bovine papilloma virus Type 1 plasmids: cis and trans requirements," *Proc. Natl. Acad. Sci. U.S.A.*, 83: 3609, 1986.

Lusky, Berg, Weiher and Botchan, "Bovine papilloma virus contains an activator of gene expression at the distal end of the early transcription unit," *Mol. Cell. Biol.* 3: 1108, 1983.

Mager and Planta, "Coordinate expression of ribosomal protein genes in yeast as a function of cellular growth rate," *Mol. Cell Biochem.*, 104: 181-187, 1991.

Majors and Varmus, "A small region of the mouse mammary tumor virus long terminal repeat confers glucocorticoid hormone regulation on a linked heterologous gene," *Proc. Natl. Acad. Sci. U.S.A.*, 80: 5866, 1983.

McNeall, Sanchez, Gray, Chesterman and Sleigh, "Hyperinducible gene expression from a metallotionein promoter containing additional metal-responsive elements," *Gene*, 76: 81, 1989.

Michel and Westhof, "Modeling of the three-dimensional architecture of group I catalytic introns based on comparative sequence analysis," *J. Mol. Biol.*, 216: 585-610, 1990.

Miksicek, Heber, Schmid, Danesch, Posseckert, Beato and Schutz, "Glucocorticoid responsiveness of the transcriptional enhancer of Moloney murine sarcoma virus," *Cell*, 46: 203, 1986.

Monahan, Samulski, Tazelaar, et al., "Direct intramuscular injection with recombinant AAV vectors results in sustained expression in a dog model of hemophilia," *Gene Ther.*, 5: 40-49, 1998.

Mordacq and Linzer, "Co-localization of elements required for phorbol ester stimulation and glucocorticoid repression of proliferin gene expression," *Genes and Dev.*, 3: 760, 1989.

Moreau, Hen, Wasylyk, Everett, Gaub and Chambon, "The SV40 base-repair repeat has a striking effect on gene expression both in SV40 and other chimeric recombinants," *Nucl. Acids Res.*, 9: 6047, 1981.

Morris et al., *Eur. J. Neurosci.*, 2: 1016, 1990.

Morris, *Learn. Motiv.*, 12: 239-260, 1981.

Morrison, Gordon, Ripps, and Morrison, "Quantitative immunocytochemical analysis of the spinal cord in G86R superoxide dismutase transgenic mice: neurochemical correlates of selective vulnerability," *J. Comp. Neurol.*, 373: 619-631, 1996.

Muesing, Smith and Capon, "Regulation of mRNA accumulation by a human immunodeficiency virus trans-activator protein," *Cell*, 48: 691, 1987.

Muzyczka and McLaughlin, "Use of adeno-associated virus as a mamalian transduction vector," In: *Current Communications in Molecular Biology: Viral Vectors*, Glzman and Hughes Eds., Cold Spring Harbor Laboratory Press, Cold Spring Harbor, N.Y., pp. 39-44, 1988.

Nakai, Herzog, Hagstrom, et al., "Adeno-associated viral vector-mediated gene transfer of human blood coagulation factor IX into mouse liver," *Blood*, 91: 4600-4607, 1998.

Nakai, Iwaki, Kay and Couto, "Isolation of recombinant adeno-associated virus vector-cellular DNA junctions from mouse liver," *J. Virol.*, 73: 5438-5447, 1999.

Nathans, Thomas and Hogness, "Molecular genetics of human color vision: the genes encoding blue, green, and red pigments," *Science*, 232: 193-202, 1986.

Ng, Gunning, Liu, Leavitt and Kedes, "Regulation of the human beta-actin promoter by upstream and intron domains," *Nuc. Acids Res.*, 17: 601, 1989.

Ohkawa, Yuyama, Taira, "Activities of HIV-RNA targeted ribozymes transcribed from a 'shot-gun' type ribozyme-trimming plasmid," *Nucl. Acids Symp. Ser.,* 27: 15-16, 1992.

Ojwang, Hampel, Looney, Wong-Staal, Rappaport, "Inhibition of human immunodeficiency virus type 1 expression by a hairpin ribozyme," *Proc. Natl. Acad. Sci. USA,* 89 (22): 10802-10806, 1992.

Ondek, Sheppard and Herr, "Discrete elements within the SV40 enhancer region display different cell-specific enhancer activities," *EMBO J.,* 6: 1017, 1987.

Ornitz, Hammer, Davison, Brinster and Palmiter, "Promoter and enhancer elements from the rat elastase I gene function independently of each other and of heterologous enhancers," *Mol. Cell. Biol.,* 7: 3466, 1987.

Palmiter, Chen and Brinster, "Differential regulation of metallothionein-thymidine kinase fusion genes in transgenic mice and their offspring," *Cell,* 29: 701, 1982.

Pech, Rao, Robbins and Aaronson, "Functional identification of regulatory elements within the promoter region of platelet-derived growth factor 2," *Mol. Cell. Biol.,* 9: 396, 1989.

Peel, Zolotukhin, Schrimsher, Muzyczka, and Reier, "Efficient transduction of green fluorescent protein in spinal cord neurons using adeno-associated virus vectors containing cell type-specific promoters," *Gene Ther.,* 4: 16-24, 1997.

Perez-Stable and Constantini, "Roles of fetal γ-globin promoter elements and the adult β-globin 3' enhancer in the stage-specific expression of globin genes," *Mol. Cell. Biol.,* 10: 1116, 1990.

Perou, Jeffrey, et al., "Distinctive gene expression patterns in human mammary epithelial cells and breast cancers," *Proc. Nat'l Acad. Sci. USA,* 96: 9212-9217, 1999.

Perreault, Wu, Cousinequ, Ogilvie, Cedergren, "Mixed deoxyribo- and ribo-oligonucleotides with catalytic activity," *Nature,* 344 (6266): 565, 1990.

Perrotta and Been, "Cleavage of oligoribonucleotides by a ribozyme derived from the hepatitis delta virus RNA sequence," *Biochem.,* 31 (1): 16, 1992.

Philip et al., "Efficient and sustained gene expression in primary T lymphocytes and primary and cultured tumor cells mediated by adeno-associated virus plasmid DNA complexed to cationic liposomes," *Mol. Cell Biol.,* 14 (4): 2411-2418, 1994.

Picard and Schaffner, "A Lymphocyte-specific enhancer in the mouse immunoglobulin kappa gene," *Nature,* 307: 83, 1984.

Pieken, Olsen, Benseler, Aurup, Eckstein, "Kinetic characterization of ribonuclease-resistant 2'-modified hammerhead ribozymes," *Science,* 253 (5017): 314, 1991.

Pinkert, Ornitz, Brinster and Palmiter, "An albumin enhancer located 10 kb upstream functions along with its promoter to direct efficient, liver-specific expression in transgenic mice," *Genes and Dev.,* 1: 268, 1987.

Polans, Baehr and Palczewski, "Turned on by Ca2+! The physiology and pathology of Ca(2+)-binding proteins in the retina," *Trends Neurosci.,* 19: 547-554, 1996.

Ponta, Kennedy, Skroch, Hynes and Groner, "Hormonal response region in the mouse mammary tumor virus long terminal repeat can be dissociated from the proviral pomoter and has enhancer properties," *Proc. Natl. Acad. Sci. U.S.A.,* 82: 1020, 1985.

Portera-Cailliau, Sung, Nathans and Adler, "Apoptotic photoreceptor cell death in mouse models of retinitis pigmentosa," *PNAS,* 91: 974-978, 1994.

Porton, Zaller, Lieberson and Eckhardt, "Immunoglobulin heavy-chain enhancer is required to maintain transfected γ2A gene expression in a pre-B-cell line," *Mol. Cell. Biol.,* 10: 1076, 1990.

Queen and Baltimore, "Immunoglobulin gene transcription is activated by downstream sequence elements," *Cell,* 35: 741, 1983.

Quinn, Farina, Gardner, Krutzsch and Levens, "Multiple components are required for sequence recognition of the AP1 site in the Gibbon ape leukemia virus enhancer," *Mol. Cell. Biol.,* 9: 4713, 1989.

Ratovitski, Corson, Strain, Wong, Cleveland, Culotta, and Borchelt, "Variation in the biochemical/biophysical properties of mutant superoxide dismutase 1 enzymes and the rate of disease progression in familial amyotrophic lateral sclerosis kindreds," *Hum. Mol. Genet.,* 8: 1451-1460, 1999.

Redondo, Hata, Brocklehurst and Krangel, "A T-cell-specific transcriptional enhancer within the human T-cell receptor δ locus, " *Science,* 247: 1225, 1990.

Reinhold-Hurek and Shub, "Self-splicing introns in tRNA genes of widely divergent bacteria," *Nature,* 357: 173-176, 1992.

Reisman and Rotter, "Induced expression from the Moloney murine leukemia virus long terminal repeat during differentiation of human myeloid cells is mediated through its transcriptional enhancer," *Mol. Cell. Biol.,* 9: 3571, 1989.

Resendez Jr., Wooden and Lee, "Identification of highly conserved regulatory domains and protein-binding sites in the promoters of the rat and human genes encoding the stress-inducible 78-kilodalton glucose-regulated protein," *Mol. Cell. Biol.,* 8: 4579, 1988.

Ridgeway, "Mammalian expression vectors," In: *Vectors: A Survey of Molecular Cloning Vectors and Their Uses,* Rodriguez and Denhardt, Eds., Stoneham: Butterworth, pp. 467-492, 1988.

Ripandelli, Coppe, Capaldo and Stirpe, "Optical coherence tomography," *Semin. Ophthalmol.,* 13: 199-202, 1998.

Ripe, Lorenzen, Brenner and Breindl, "Regulatory elements in the 5' flanking region and the first intron contribute to transcriptional control of the mouse alpha-1-type collagen gene," *Mol. Cell. Biol.,* 9: 2224, 1989.

Ripps, Huntley, Hof, Morrison, and Gordon, "Transgenic mice expressing an altered murine superoxide dismutase gene provide an animal model of amyotrophic lateral sclerosis," *Proc. Natl. Acad. Sci. USA,* 92: 689-693, 1995.

Rittling, Coutinho, Amarm and Kolbe, "AP-1/jun-binding sites mediate serum inducibility of the human vimentin promoter," *Nuc. Acids Res.,* 17: 1619, 1989.

Rivera, Ye, Courage, et al., "Long-term regulated expression of growth hormone in mice after intramuscular gene transfer," *Proc. Nat'l Acad. Sci. USA,* 96: 8657-62, 1999.

Rolling, Nong, Pisvin and Collen, "Adeno-associated virus-mediated gene transfer into rat carotid arteries," *Gene Therapy,* 4: 757-761, 1997.

Rosen et al., *Nature,* 362: 59-62, 1993. Wang et al., "Efficient CFTR expression from AAV vectors packaged with promoters—the second generation," *Gene Ther.,* 6 (4): 667-675, 1999.

Rosen, Sodroski and Haseltine, "The location of cis-acting regulatory sequences in the human T-cell lymphotropic virus type III (HTLV-111/LAV) long terminal repeat," *Cell,* 41: 813, 1988.

Rosenzweig, "Aspects of the search for neural mechanisms of memory," *Ann. Rev. Psychol.,* 47: 1-32, 1996.

Rossi, Elkins, Zaia, Sullivan, "Ribozymes as anti-HIV-1 therapeutic agents: principles, applications, and problems," *AIDS Res. Hum. Retrovir.,* 8 (2): 183, 1992.

Roth, Hughes, Estep and Church, "Finding DNA regulatory motifs within unaligned noncoding sequences clustered by whole-genome mRNA quantitation," *Nat. Biotechnol.,* 16: 939-945, 1998.

Sakai, Helms, Carlstedt-Duke, Gustafsson, Rottman and Yamamoto, "Hormone-mediated repression: A negative glucocorticoid-response element from the bovine prolactin gene," *Genes and Dev.,* 2: 1144, 1988.

Sambrook et al., *Molecular Cloning: A Laboratory Manual*, Cold Spring Harbor Laboratory, Cold Spring Harbor, N.Y., 1989.

Sarver, Cantin, Chang, Zaia, Ladne, Stephens, Rossi, "Ribozymes as a potential anti-HIV-1 therapeutic agents," *Science,* 247 (4947): 1222-1225, 1990.

Satake, Furukawa and Ito, "Biological activities of oligonucleotides spanning the F9 point mutation within the enhancer region of polyoma virus DNA," *J. Virology,* 62: 970, 1988.

Saville and Collins, "A site-specific self-cleavage reaction performed by a novel RNA in *Neurospora* mitochondria," *Cell,* 61 (4): 685-696, 1990.

Saville and Collins, "RNA-mediated ligation of self-cleavage products of a *Neurospora* mitochondrial plasmid transcript," *Proc. Natl. Acad. Sci. USA,* 88 (19): 8826-8830, 1991.

Sawicki et al., "A composite CMV-IE enhancer/beta-actin promoter is ubiquitously expressed in mouse cutaneous epithelium," *Exp. Cell Res.,* 10: 367-369, 1998.

Scanlon, Jiao, Funato, Wang, Tone, Rossi, Kashani-Sabet, "Ribozyme-mediated cleavage of c-fos mRNA reduces gene expression of DNA synthesis enzymes and metallothionein," *Proc. Natl. Acad. Sci. USA,* 88 (23): 10591-10595, 1991.

Scaringe, Francklyn, Usman, "Chemical synthesis of biologically active oligoribonucleotides using beta-cyanoethyl protected ribonucleoside phosphoramidites," *Nucl. Acids Res.,* 18 (18): 5433-5441, 1990.

Schaffner, Schirm, Muller-Baden, Wever and Schaffner, "Redundancy of information in enhancers as a principle of mammalian transcription control," *J. Mol. Biol.,* 201: 81, 1988.

Schena, Shalon, Davis and Brown, "Quantitative monitoring of gene expression patterns with a complementary DNA microarray," *Science,* 270: 467-470, 1995.

Searle, Stuart and Palmiter, "Building a metal-responsive promoter with synthetic regulatory elements," *Mol. Cell. Biol.,* 5: 1480, 1985.

Serrano, Lee, Chin, Cordon-Cardo, Beach and DePinho, "Role of the INK4a locus in tumor suppression and cell mortality," *Cell,* 85: 27-37, 1996.

Shafron, Simpkins, Jebelli, Day and Meyer, "Reduced MK801 binding in neocortical neurons after AAV-mediated transfections with NMDA-R1 antisense cDNA," *Brain Res.,* 784: 325-328, 1998.

Sharp and Marciniak, "HIV Tar: An RNA enhancer?" *Cell,* 59: 229, 1989.

Shaul and Ben-Levy, "Multiple nuclear proteins in liver cells are bound to Hepatitis B virus enhancer element and its upstream sequences," *EMBO J.,* 6: 1913, 1987.

Shaw and Lewin, "Protein-induced folding of a group I intron in cytochrome b pre-mRNA," *J. Biol. Chem.,* 270 (37): 21552-62, 1995.

Shaw, Whalen, Drenser, et al., "Ribozymes in the treatment of retinal disease," In: *Vertebrate Phototransduction and the Visual Cycle. Methods in Enzymology* 316 Palczewski, Ed., New York, Academic Press, in press, 2000.

Shefner et al., "Mice lacking cytosolic copper/zinc superoxide dismutase display a distinctive motor axonopathy," *Neurology,* 53 (6): 1239-1246, 1999.

Sherman, Basta, Moore, Brown and Ting, "Class II box consensus sequences in the HLA-DRα gene: Transcriptional function and interaction with nuclear proteins," *Mol. Cell. Biol.,* 9: 50, 1989.

Shimayama, Nishikawa and Taira, "Generality of the NUX rule: kinetic analysis of the results of systematic mutations in the trinucleotide at the cleavage site of hammerhead ribozymes," *Biochem.,* 34: 3649-3654, 1995.

Silva et al., "CREB and memory," *Ann. Rev. Neurosci.,* 21: 127-148, 1998.

Simmons et al., *J. Histochem.,* 12: 169-181, 1989.

Sleigh and Lockett, "SV40 enhancer activation during retinoic-acid-induced differentiation of F9 embryonal carcinoma cells," *J. EMBO,* 4: 3831, 1985.

Snyder, Miao, Meuse, et al., "Correction of hemophilia B in canine and murine models using recombinant adeno-associated viral vectors," *Nat. Med.,* 5: 64-70, 1999.

Snyder, Miao, Patijn, et al., "Persistent and therapeutic concentrations of human factor IX in mice after hepatic gene transfer of recombinant AAV vectors," *Nat. Genet.,* 16: 270-276, 1997.

Song et al., "Sustained secretion of human alpha-1-antitrypsin from muscle transduced with adeno-associated virus vectors," *Proc. Natl. Acad. Sci. USA,* 24: 14384-14388, 1998.

Spalholz, Yang and Howley, "Transactivation of a bovine papilloma virus transcriptional regulatory element by the E2 gene product," *Cell,* 42: 183, 1985.

Spandau and Lee, "Trans-activation of viral enhancers by the Hepatitis B virus X protein," *J. Virology,* 62: 427, 1988.

Spandidos and Wilkie, "Host-specificities of papilloma virus, Moloney murine sarcoma virus and simian virus 40 enhancer sequences," *EMBO J.,* 2: 1193, 1983.

Stephens and Hentschel, "The bovine papilloma virus genome and its uses as a eukaryotic vector," *Biochem. J.,* 248: 1, 1987.

Stuart, Searle and Palmiter, "Identification of multiple metal regulatory elements in mouse metallothionein-I promoter by assaying synthetic sequences," *Nature,* 317: 828, 1985.

Studier, Rosenberg, Dunn and Dubendorff, "Use of T7 RNA polymerase to direct expression of cloned genes," *Methods Enzymol.,* 185: 60-89, 1990.

Sullivan and Peterlin, "Transcriptional enhancers in the HLA-DQ subregion," *Mol. Cell. Biol.,* 7: 3315, 1987.

Swartzendruber and Lehman, "Neoplastic differentiation: Interaction of simian virus 40 and polyoma virus with murine teratocarcinoma cells," *J. Cell. Physiology,* 85: 179, 1975.

Taira, Nakagawa, Nishikawa, Furukawa, "Construction of a novel RNA-transcript-trimming plasmid which can be used both in vitro in place of run-off and (G)-free transcriptions and in vivo as multi-sequences transcription vectors," *Nuc. Acids Res.,* 19 (19): 5125-5130, 1991.

Takebe, Seiki, Fujisawa, Hoy, Yokota, Arai, Yoshida and Arai, "SRα promoter: An efficient and versatile mammalian cDNA expression system composed of the simian virus 40 early promoter and the R-U5 segment of human T-cell leukemia virus Type 1 long terminal repeat," *Mol. Cell. Biol.,* 8: 466, 1988.

Tamayo, Slonim, Mesirov, et al., "Interpreting patterns of gene expression with self-organizing maps: methods and application to hematopoietic differentiation," *Proc. Nat'l Acad. Sci. USA,* 96: 2907-2912, 1999.

Tavazoie, Hughes, Campbell, et al., "Systematic determination of genetic network architecture," *Nat. Genet.,* 22: 281-285, 1999.

Tavernier, Gheysen, Duerinck, Cander heyden and fiers, "Deletion mapping of the inducible promoter of human IFN-beta gene," *Nature,* 301: 634, 1983.

Taylor and Kingston, "E1a trans-activation of human HSP70 gene promoter substitution mutants is independent of the composition of upstream and TATA elements," *Mol. Cell. Biol.,* 10: 176, 1990b.

Taylor and Kingston, "Factor substitution in a human HSP70 gene promoter: TATA-dependent and TATA-independent interactions," *Mol. Cell. Biol.,* 10: 165, 1990a.

Taylor, Solomon, Weiner, Paucha, Bradley and Kingston, "Stimulation of the human heat-shock protein 70 promoter in vitro by simian virus 40 large T antigen," *J. Biol. Chem.,* 264: 15160, 1989.

Thiesen, Bosze, Henry and Charnay, "A DNA element responsible for the different tissue specificities of friend and Moloney retroviral enhancers," *J. Virology,* 62:614, 1988.

Timmers, Newton and Hauswirth, "Synthesis and stability of retinal photorecptor mRNAs are coordinately regulated during bovine fetal development," *Exp. Eye Res.,* 56:251-265, 1993.

Treisman, "identification of a protein-binding site that mediates transcriptional response to the c-fos gene to serum factors," *Cell,* 46(4):567-574, 1986.

Tronche, Rollier, Bach, Weiss and Yaniv, "The rat albumin promoter: Cooperation with upstream elements is required when binding of APF/HNF 1 to the proximal element is partially impaired by mutation or bacterial methylation," *Mol. Cell. Biol.,* 9:4759, 1989.

Tronche, Rollier, Herbomel, Bach, Cereghini, Weiss and Yaniv, "Anatomy of the rat albumin promoter," *Mol. Biol. Med.,* 7:173, 1990.

Trudel and Constantini, "A 3' enhancer contributes to the stage-specific expression of the human beta-globin gene," *Genes and Dev.,* 6:954, 1987.

Tsang, Chen, Kjeldbye, et al., "Retarding photoreceptor degeneration in Pdegtm1/Pdeg/ml mice by an apoptosis suppressor gene," *Invest. Ophthalmol. Vis. Sci.,* 38:943-950, 1997.

Turkel, Liao and Farabaugh, "GCR1-dependent transcriptional activation of yeast retrotransposon Ty2-," *Yeast,* 13:917-930, 1997.

Tyndall, La Mantia, Thacker, Favaloro and Kamen, "A region of the polyoma virus genome between the replication origin and late protein-coding sequences is required in cis for both early gene expression and viral DNA replication," *Nuc. Acids. Res.,* 9:6231, 1981.

Usman and Cedergren, "Exploiting the chemical synthesis of RNA," *Trends Biochem. Sci.,* 17(9):334, 1992.

Usman et al., *J. Am. Chem. Soc.,* 109:7845-7854, 1987.

Vannice and Levinson, "Properties of the human Hepatitis B virus enhancer: Position effects and cell-type nonspecificity," *J. Virology,* 62:1305, 1988.

Vasseur, Kress, Montreau and Blangy, "Isolation and characterization of polyoma virus mutants able to develop in multipotential murine embryonal carcinoma cells," *Proc. Natl. Acad. Sci. U.S.A.,* 77:1068, 1980.

Ventura, Wang, Ragot, Perricaudet, Saragosti, "Activation of HIV-specific ribozyme activity by self-cleavage," *Nuc. Acids Res.,* 21:3249-3255, 1993.

Vogelstein and Knizler, "The multistep nature of cancer," *Trends Genet.,* 9:138-141, 1993.

Wagner, Reynolds, Moran, et al., "Efficient and persistent gene transfer of AAV-CFTR in maxillary sinus," *Lancet,* 351:1702-1703, 1998.

Wang and Calame, "SV40 enhancer-binding factors are required at the establishment but not the maintenance step of enhancer-dependent transcriptional activation," *Cell,* 47:241, 1986.

Weber, De Villiers and Schaffner, "An SV40 'enhancer trap' incorporates exogenous enhancers or generates enhancers from its own sequences," *Cell,* 36:983, 1984.

Weerasinghe, Liem, Asad, Read, Joshi, "Resistance to human immunodeficiency virus type 1 (HIV-1) infection in human CD4+ lymphocyte-derived cell lines conferred by using retroviral vectors expression an HIV-1 RNA-specific ribozyme," *J. Virol.,* 65(10):5531-5534, 1991.

Weinberger, Jat and Sharp, "Localization of a repressive sequence contributing to B-cell specificity in the immunoglobulin heavy-chain enhancer," *Mol. Cell. Biol.,* 8:988, 1984.

Williams et al., "Cooperative tumorigenic effects of germ-line mutations in Rb and p53," *Nature Genet.,* 7:480-484, 1994.

Winoto and Baltimore, "$\alpha\beta$-lineage-specific expression of the a T-cell receptor-gene by nearby silencers," *Cell,* 59:649, 1989.

Woolf, Melton, Jennings, "Specificity of antisense oligonucleotides in vivo," *Proc. Natl. Acad. Sci. USA,* 89(16): 7305-7309, 1992.

Xiao, Berta, Lu, et al., "Adeno-associated virus as a vector for liver-directed gene therapy," *J. Virol.,* 72:10222-10226, 1998.

Xiao, Li and Samulski, "Efficient long-term transfer into muscle tissue of immunocompetent mice by adeno-associated virus vector," *J. Virol.,* 70:8098-8108, 1996.

Xiao, Li and Samulski, "Production of high-titer recombinant adeno-associated virus vectors in the absence of helper adenovirus," *J. Virol.,* 72:2224-2232, 1998.

Xiao, Li, McCown and Samulski, "Gene transfer by adeno-associated virus vectors into the central nervous system," *Exp. Neurol.,* 144:113-124, 1997.

Yan, Lewin and Hauswirth. "Selective degradation of nonsense beta-phosphodiesterase mRNA in the heterozygous rd mouse," *Invest. Ophthalmol. Vis. Sci.,* 39:2529-2536, 1998.

Yarfitz and Hurley, "Transduction mechanisms of vertebrate and invertebrate photoreceptors," *J. Biol. Chem.,* 269: 14329-14332, 1994.

Yu, Ojwang, Yamada, Hampel, Rapapport, Looney, Wong-Staal, "A hairpin ribozyme inhibits expression of diverse strains of human immunodeficiency virus type 1," *Proc. Natl. Acad. Sci. USA,* 90:6340-6344, 1993.

Yutzey, Kline and Konieczny, "An internal regulatory element controls troponin I gene expression," *Mol. Cell. Biol.,* 9:1397, 1989.

Zolotukhin, Byrne, Mason, et al., "Recombinant adeno-associated virus purification using novel methods improves infectious titer and yield," *Gene Ther.,* 6:973-985, 1999. Zhou, Giordano, Durbin, McAllister, "Synthesis of functional mRNA in mammalian cells by bacteriophage T3 RNA polymerase," *Mol. Cell Biol.,* 10(9): 4529-4537, 1990.

Zolotukhin, Potter, Hauswirth, Guy and Muzyczka, "A 'humanized' green fluorescent protein cDNA adapted for high-level expression in mammalian cells," *J. Virol.,* 70:4646-4654, 1996.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

What is claimed is:

1. An isolated ribozyme that specifically cleaves the nucleic acid sequence of SEQ ID NO:50.

2. The ribozyme of claim 1, wherein said ribozyme is a hammerhead ribozyme.

3. The ribozyme of claim 1, wherein said ribozyme specifically cleaves a polynucleotide that encodes a manganese superoxide dismutase (MnSOD) polypeptide.

4. The ribozyme of claim 1, wherein said ribozyme comprises the nucleic acid sequence of SEQ ID NO:49.

5. A vector comprising a polynucleotide encoding the ribozyme of claim 1, said polynucleotide operably linked to at least a first promoter element that directs expression of said polynucleotide in a mammalian cell.

6. The vector of claim 5, wherein said vector is a viral vector.

7. The vector of claim 6, wherein said viral vector is an adeno-associated viral vector.

8. The vector of claim 5, wherein said promoter element directs expression of said polynucleotide in a non-human mammalian cell.

9. The vector of claim 5, wherein said promoter element comprises a constitutive or an inducible promoter element.

10. A virus comprising the ribozyme of claim 1, or a polynucleotide that encodes the ribozyme of claim 1.

11. The virus of claim 10, wherein said virus is an adenovirus or an adeno-associated virus.

12. The virus of claim 11, wherein said virus is an adeno-associated virus.

13. A composition comprising: (a) the ribozyme of claim 1; (b) the vector of claim 5; or (c) the virus of claim 10.

14. The composition of claim 13, further comprising a pharmaceutical excipient.

15. The composition of claim 13, formulated for administration to a non-human mammal.

16. A kit comprising: (a) the composition of claim 13; and (b) instructions for using said kit in producing a non-human mammalian animal model of retinal disease or optic neuropathy.

* * * * *